(12) United States Patent
Franco et al.

(10) Patent No.: US 12,139,815 B2
(45) Date of Patent: Nov. 12, 2024

(54) METHODS FOR RAPID DETECTION OF IMMUNOGENIC EPITOPES IN BIOTHREAT AGENTS AND EMERGING PATHOGENS FOR PEPTIDE VACCINES AND THERAPEUTICS

(71) Applicant: Lawrence Livermore National Security, LLC, Livermore, CA (US)

(72) Inventors: Magdalena Franco, Livermore, CA (US); Nicole Collette, Livermore, CA (US); Patrik D'Haeseleer, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 5 days.

(21) Appl. No.: 17/586,687

(22) Filed: Jan. 27, 2022

(65) Prior Publication Data
US 2022/0238183 A1    Jul. 28, 2022

Related U.S. Application Data

(60) Provisional application No. 63/142,870, filed on Jan. 28, 2021.

(51) Int. Cl.
| | | |
|---|---|---|
| C40B 30/04 | (2006.01) | |
| C40B 40/10 | (2006.01) | |
| G16B 20/30 | (2019.01) | |
| G16B 40/20 | (2019.01) | |

(52) U.S. Cl.
CPC .............. *C40B 30/04* (2013.01); *C40B 40/10* (2013.01); *G16B 20/30* (2019.02); *G16B 40/20* (2019.02)

(58) Field of Classification Search
None
See application file for complete search history.

(56) References Cited

PUBLICATIONS

Frietze et al. (2017) PLoS ONE vol. 12 article e0171511 pp. 1 to 13.*
Alvarez-Castelao et al. (Apr. 1, 2019) Nature Protocols vol. 19 pp. 556 to 575.*
Al-Maleki et al., "Altered Proteome of Burkholderia pseudomallei Colony Variants Induced by Exposure to Human Lung Epithelial Cells", PLOS ONE, 2015, vol. 10(5), pp. 1-31.
Ashkenazy et al., "ConSurf 2016: an improved methodology to estimate and visualize evolutionary conservation in macromolecules", Nucleic Acids Research, 2016, vol. 44, pp. W344-W350.
Ashtekar et al., "A Mucosal Subunit Vaccine Protects against Lethal Respiratory Infection with Francisella tularensis LVS", PLOS ONE, 2012, vol. 7, Issue 11, e50460, pp. 1-14.
Bi et al., "Identification of Two Distinct Linear B Cell Epitopes of the Matrix Protein of the Newcastle Disease Virus Vaccine Strain LaSota", Viral Immunology, 2019, vol. 32, No. 5, pp. 1-9.

(Continued)

*Primary Examiner* — Christian C Boesen
(74) *Attorney, Agent, or Firm* — Foley & Lardner LLP

(57) ABSTRACT

A newly developed generalizable screening method enables efficient identification of epitopes, in the proteomes of pathogenic agent is provided. Also disclosed are systems that enable the method as well as epitopes discovered using the method.

11 Claims, 17 Drawing Sheets
Specification includes a Sequence Listing.

(56) References Cited

PUBLICATIONS

Blakeley-Ruiz et al., "Metaproteomics reveals persistent and phylum-redundant metabolic functional stability in adult human gut microbiomes of Crohn's remission patients despite temporal variations in microbial taxa, genomes, and proteomes", Microbiome, 2019, vol. 7:18, pp. 1-15.
Burtnick et al., "The Cluster 1 Type VI Secretion System Is a Major Virulence Determinant in Burkholderia pseudomallei", Infection and Immunity, 2011, vol. 79, No. 4, pp. 1512-1525.
Caron et al., "Analysis of Major Histocompatibility Complex (MHC) Immunopeptidomes Using Mass Spectrometry", Molecular & Cellular Proteomics, 2015, vol. 14(12), pp. 3105-5117.
Chaudhury et al., "Rapid Countermeasure Discovery against Francisella tularensis Based on a Metabolic Network Reconstruction", PLOS ONE, 2013, vol. 8(5), e63369, pp. 1-13.
Cheung et al., "A proteomics approach for the identification and cloning of monoclonal antibodies from serum", Nature Biotechnology, 2012, vol. 30, No. 5, pp. 447-454.
Clinton et al., "Binding and activation of host plasminogen on the surface of Francisella tularensis", BMC Microbiology, 2010, vol. 10:76, pp. 1-9.
Conlan et al., "Differential ability of novel attenuated targeted deletion mutants of Francisella tularensis subspecies tularensis strain SCHU S4 to protect mice against aerosol challenge with virulent bacteria: effects of host background and route of immunization", Vaccine, 2010, vol. 28(7) pp. 1-18.
Devi et al., "Exploring rotavirus proteome to identify potential B- and T-cell epitope using computational immunoinformatics", Heliyon, 2020, vol. 6, e05760, pp. 1-18.
Eickhoff et al., "Highly conserved influenza T cell epitopes induce broadly protective immunity", Vaccine, 2019, vol. 37, pp. 5371-5381.
Fiuza et al., "EpitoCore: Mining Conserved Epitope Vaccine Candidates in the Core Proteome of Multiple Bacteria Strains", Frontiers in Immunology, 2020, vol. 11(816), pp. 1010.
Franco et al., "Proteomic Profiling of Burkholderia thailandensis During Host Infection Using Bio-Orthogonal Noncanonical Amino Acid Tagging (BONCAT)", Frontiers in Cellular and Infection Microbiology, 2018, vol. 8(370), pp. 1-16.
Fulton et al., "Immunoproteomic analysis of the human antibody response to natural tularemia infection with Type A or Type B strains or LVS vaccination", International Journal of Medical Microbiology, 2011, vol. 301, pp. 591-601.
Gibney et al., "Reducing the melioidosis burden: public health, chronic disease prevention, or improved case management?", Lancet Infectious Diseases, 2019, vol. 19(8), pp. 800-802.
Golovliov et al., "A ∧clpB Mutant of Francisella tularensis Subspecies holarctica Strain, FSC200, Is a More Effective Live Vaccine than F. tularensis LVS in a Mouse Respiratory Challenge Model of Tularemia", PLOS ONE, 2013, vol. 8, Issue 11, e78671, pp. 1-8.
Gonzales et al., "Naturally Acquired Humoral Immunity Against Plasmodium falciparum Malaria", Frontiers in Immunology, 2020, vol. 11(594653), pp. 1-15.
Grassl et al., "Ultra-deep and quantitative saliva proteome reveals dynamics of the oral microbiome", Genome Medicine, 2016, vol. 8:44, pp. 1-13.
Hogan et al., "Antibodies are Major Drivers of Protection against Lethal Aerosol Infection with Highly Pathogenic Burkholderia spp.", mSphere, 2019, vol. 4, Issue 1, pp. 1-4.
Jaenisch et al., "High-density Peptide Arrays Help to Identify Linear Immunogenic B-cell Epitopes in Individuals Naturally Exposed to Malaria Infection", Molecular & Cellular Proteomics, 2019, vol. 18, pp. 642-656.
Jespersen et al., "BepiPred-2.0: improving sequence-based B-cell epitope prediction using conformational epitopes", Nucleic Acids Research, 2017, vol. 45, pp. W24-W29.

Khakhum et al., "Burkholderia pseudomallei ∧tonB ∧hcp1 Live Attenuated Vaccine Strain Elicits Full Protective Immunity against Aerosolized Melioidosis Infection", mSphere, 2019, vol. 4, Issue 1, pp. 1-13.
Khambhati et al., "Exploring the Potential of Cell-Free Protein Synthesis for Extending the Abilities of Biological Systems", Frontiers in Bioengineering and Biotechnology, 2019, vol. 7(248), pp. 1-16.
Kilmury et al., "The Francisella tularensis proteome and its recognition by antibodies", Frontiers in Microbiology, 2011, vol. 1, pp. 1-22.
Kringelum et al., "Reliable B Cell Epitope Predictions: Impacts of Method Development and Improved Benchmarking", PLoS Comput Biol, 2012, vol. 8(12), e1002829, pp. 1-10.
Li et al., "Latently and uninfected healthcare workers exposed to TB make protective antibodies against Mycobacterium tuberculosis", PNAS, 2017, vol. 114, No. 19. pp. 5023-5028.
Li et al., "Peptide Vaccine: Progress and Challenges", Vaccines, 2014, vol. 2, pp. 515-536.
Lindgren et al., "Identification of Mechanisms for Attenuation of the FSC043 Mutant of Francisella tularensis SCHU S4", Infection and Immunity, vol. 82, No. 9, pp. 3622-3635.
Liu et al., "Deep learning methods improve linear B-cell epitope prediction", BioData Mining, 2020, vol. 13:1, pp. 1-13.
Long et al., "Metaproteomics characterizes human gut microbiome function in colorectal cancer", npj Biofilms and Microbiomes, 2020, vol. 6:14, pp. 1-10.
Lu et al., "B-Cell Epitopes in GroEL of Francisella tularensis", PLOS ONE, 2014, vol. 9, Issue 6, e99847, pp. 1-20.
Mahdavi et al., "Identification of secreted bacterial proteins by noncanonical amino acid tagging", PNAS, 2014, vol. 111, No. 1, pp. 433-438.
Malonis et al., "Peptide-Based Vaccines: Current Progress and Future Challenges", Chem. Rev., 2020, vol. 120, pp. 3210-3229.
Manavalan et al., "iBCe-eL: A New ensemble Learning Framework for Improved Linear B-Cell epitope Prediction", Frontiers in Immunology, 2018, vol. 9(1695), pp. 1-11.
Mara-Koosham et al., "Antibodies Contribute to Effective Vaccination against Respiratory Infection by Type A Francisella tularensis Strains", Infection and Immunity, 2011, vol. 79, No. 4, pp. 1770-1778.
Moise et al., "iVAX: An integrated toolkit for the selection and optimization of antigens and the design of epitope-driven vaccines", Human Vaccines & Immunotherapeutics, 2015, vol. 11:9, pp. 2312-2321.
Nakajima et al., "Towards Development of Improved Serodiagnostics for Tularemia by Use of Francisella tularensis Proteome Microarrays", Journal of Clinical Microbiology, 2016, vol. 54, No. 7, pp. 1755-1765.
Ndam et al., "Protective Antibodies against Placental Malaria and Poor Outcomes during Pregnancy, Benin", Emerging Infectious Diseases, 2015, vol. 21, No. 5, pp. 813-823.
Noah et al., "GroEL and Lipopolysaccharide from Francisella tularensis Live Vaccine Strain Synergistically Activate Human Macrophages", Infection and Immunity, 2010, vol. 78, No. 4, pp. 1797-1806.
Norris et al., "Stable, Site-Specific Fluorescent Tagging Constructs Optimized for Burkholderia Species", Applied and Environmental Microbiology, 2010, vol. 76, No. 22, pp. 7635-7640.
Park et al., "ComPIL 2.0: An Updated Comprehensive Metaproteomics Database", J Proteome Res., 2019, vol. 18(2), pp. 616-622.
Peng et al., "Elevated AIM2-mediated pyroptosis triggered by hypercytotoxic Francisella mutant strains is attributed to increased intracellular bacteriolysis", Cell Microbiol., 2011, vol. 13(10), pp. 1586-1600.
Perez-Riverol et al., "The PRIDE database and related tools and resources in 2019: improving support for quantification data", Nucleic Acids Research, 2019, vol. 47, pp. D442-D450.
Propst et al., "A Burkholderia pseudomallei ∧purM Mutant Is Avirulent in Immunocompetent and Immunodeficient Animals: Candidate Strain for Exclusion from Select-Agent Lists", Infection and Immunity, 2010, vol. 78, No. 7, pp. 3136-3143.

(56) References Cited

PUBLICATIONS

Safavi et al., "Exploring the out of sight antigens of SARS-COV-2 to design a candidate multi-epitope vaccine by utilizing immunoinformatics approaches", Vaccine, 2020, vol. 38, pp. 7612-7628.
Shams et al., "Fructose-1,6-bisphosphate aldolase (FBA)—a conserved glycolytic enzyme with virulence functions in bacteria: 'ill met by moonlight'", Biochemical Society Transactions, 2014, vol. 42, part 6, pp. 1792-1795.
Sharma et al., "Rapid selection and identification of functional CD8 T cell epitopes from large peptide-coding libraries", Nature Communications, 2019, vol. 10:4553, pp. 1-13.
Sharma et al., "T-cell epitope discovery technologies", Human Immunology, 2014, vol. 75, pp. 514-519.
Singh et al., "Improved Method for Linear B-Cell Epitope Prediction Using Antigen's Primary Sequence", PLoS ONE, 2013, vol. 8(5), e62216, pp. 1-8.
Skwarczynski et al., "Peptide-based synthetic vaccines", Chem. Sci., 2016, vol. 7, pp. 842-854.
Su et al., "Characterization of stable, constitutively expressed, chromosomal green and red fluorescent transcriptional fusions in the select agent bacterium, Francisella tularensis Schu S4 and the surrogate type B live vaccine strain (LVS)", Appl Microbiol Biotechnol, 2013, vol. 97, pp. 9029-9041.
Sun et al., "Bioinformatics Resources and Tools for Conformational B-Cell Epitope Prediction", Computational and Mathematical Methods in Medicine, 2013, Vo. 2013, pp. 1-11.
Sun et al., "Thermal stability of self-assembled peptide vaccine materials", Acta Biomaterialia, 2016, vol. 30, pp. 62-71.
Twine et al., "BALB/c mice, but not C57BL/6 mice immunized with a ∆clpB mutant of Francisella tularensis subspecies tularensis are protected against respiratory challenge with wild-type bacteria: Association of protection with post-vaccination and post-challenge immune responses", Vaccine, 2012, vol. 30, pp. 3634-3645.
Valentino et al., "Identification of T-cell epitopes in Francisella tularensis using an ordered protein array of serological targets", Immunology, 2011, vol. 132, pp. 348-360.
Varga et al., "Distinct human antibody response to the biological warfare agent Burkholderia mallei", Virulence, 2012, vol. 3:6, pp. 510-514.
Vita et al., "The Immune Epitope Database (IEDB): 2018 update", Nucleic Acids Research, 2019, vol. 47, pp. D339-D343.
Wang et al., "Mapping the B cell epitopes within the major capsid protein L1 of human papillomavirus type 16", International Journal of Biological Macromolecules, 2018, vol. 118, pp. 1354-1361.
Wang et al., "Mapping the B cell epitopes within the major capsid protein L1 of human papillomavirus type 16", International Journal of Biological Macromolecules, vol. 118, pp. 1354-1361.
Whitlock et al., "Protective response to subunit vaccination against intranasal Burkholderia mallei and B. pseudomallei challenge", Procedia Vaccinol., 2010, vol. 2(1), pp. 1-9.
Wier et al., "New Method for the Orthogonal Labeling and Purification of Toxoplasma gondii Proteins While Inside the Host Cell", mBio, 2015, vol. 6, Issue 2, e01628-14, pp. 1-12.
Wiersinga et al., "Melioidosis", The New England Journal of Medicine, 2012, vol. 367, pp. 1035-1044.
Yi et al., "Caprine humoral response to Burkholderia pseudomallei antigens during acute melioidosis from aerosol exposure", PLoS Negl Trop Dis, 2019, vol. 13(2), pp. 1-25.
Zhang et al., "Deep Metaproteomics Approach for the Study of Human Microbiomes", Anal. Chem., 2017, vol. 89, pp. 9407-9415.
Zhao et al., "Screening and identification of B-cell epitopes within envelope protein of tembusu virus", Virology Journal, 2018, vol. 15:142, pp. 1-8.

\* cited by examiner

FIG. 7

| Protein name | Gene | Notes |
|---|---|---|
| Aminotransferase | aspC1 | |
| Glutamate dehydrogenase | gdh | Known antigen |
| Pyruvate dehydrogenase acetyltransferase unit | aceF | Known antigen |
| 60 kDa chaperonin | groL | Known antigen |
| Chaperone protein DnaK | dnaK | Known antigen |
| Chaperone protein DnaK | dnaK | Known antigen |
| 60 kDa chaperonin | groL | Known antigen |
| 60 kDa chaperonin | groL | Known antigen |
| Catalase-peroxidase | katG | Known antigen |
| Malate dehydrogenase | mdh | Known antigen |
| Outer membrane protein 26 | omp26 | OuterMembrane |
| Succinate dehydrogenase flavoprotein subunit | sdhA | Known antigen |
| ATP synthase subunit alpha | atpA | Known antigen |
| Elongation factor Ts | tsf | Known antigen |
| Elongation factor Ts | tsf | Known antigen |
| Chaperone protein DnaK | dnaK | Known antigen |
| Cell division protein FtsZ | ftsZ | Known antigen |
| Trigger factor | tig | |
| ATP synthase subunit alpha | atpA | Known antigen |
| Catalase-peroxidase | katG | Known antigen |
| Isocitrate dehydrogenase [NADP] | idh | Known antigen |
| Fructose-1,6-bisphosphate aldolase | fbaB | Known antigen |
| Glutamate dehydrogenase | gdh | Known antigen |
| Succinate--CoA ligase [ADP-forming] subunit beta | sucC | Known antigen |
| Chaperone protein DnaK | dnaK | Known antigen |
| Malonyl CoA-acyl carrier protein transacylase | | Known antigen |
| Peroxiredoxin | | Known antigen |
| Chaperone protein DnaK | dnaK | Known antigen |
| Conserved hypothetical lipoprotein | lpnA | Known antigen |
| Elongation factor Tu | tuf | Known antigen |
| Succinate--CoA ligase [ADP-forming] subunit beta | sucC | Known antigen |
| 30S ribosomal protein S1 | rpsA | Known antigen |
| Elongation factor Tu | tuf | Known antigen |
| Transcription elongation factor GreA | greA | Known antigen |
| 60 kDa chaperonin | groL | Known antigen |
| Aconitate hydratase | acnA | Known antigen |
| Chaperone protein DnaK | dnaK | Known antigen |
| Chaperone protein DnaK | dnaK | Known antigen |
| Outer membrane protein 26 | omp26 | |
| 3-oxoacyl-[Acyl-carrier-protein] reductase | fabG | |
| Chaperone protein DnaK | dnaK | Known antigen |
| Enoyl-[acyl-carrier-protein] reductase [NADH] | fabI | |
| Aconitate hydratase | acnA | Known antigen |
| Elongation factor Ts | tsf | Known antigen |

FIG. 8

| Protein name | Gene | Notes |
|---|---|---|
| Aspartate--tRNA(Asp/Asn) ligase | aspS | |
| Adenylosuccinate synthetase | purA | |
| Dihydrolipoyl dehydrogenase | odhL | |
| Ankyrin repeat-containing protein | | |
| Phosphoribosylformylglycinamidine synthase | purL | |
| DNA-directed RNA polymerase subunit beta | rpoB | |
| 50S ribosomal protein L6 | rplF | |
| DNA-directed RNA polymerase subunit beta' | rpoC | |
| Enolase | eno | |
| Uncharacterized protein | | |
| DNA gyrase subunit A | gyrA | |
| Aspartate-semialdehyde dehydrogenase | asd | |
| Malic enzyme | | |
| 50S ribosomal protein L10 | rplJ | |
| 50S ribosomal protein L6 | rplF | |
| Glutamine synthetase | glnA | |
| Nucleoside diphosphate kinase | ndk | Extracellular |
| Antioxidant protein LsfA | | |
| UDP-glucose 4-epimerase | | |
| Enolase | eno | |
| Acetyl-CoA acetyltransferase | | |
| Adenosylhomocysteinase | ahcY | |
| KHG/KDPG aldolase | eda | |
| 10 kDa chaperonin | groES | Known antigen |
| Saccharopine dehydrogenase | | |
| Citrate synthase | gltA | |
| Aspartate--tRNA(Asp/Asn) ligase | aspS | |
| Gamma-aminobutyraldehyde dehydrogenase | | |
| Peptide chain release factor 2 | prfB | |
| Polyketide non-ribosomal peptide synthase | | |
| Transcription termination/antitermination protein | nusG | |
| Beta sliding clamp | dnaN | |
| Malate synthase | aceB | |
| PTS system, EIIA component | | |
| Phosphoenolpyruvate synthase | ppsA | |
| Thiol:disulfide interchange protein | dsbA | |
| RND family efflux transporter MFP subunit | bpeA | |
| Inosine-5'-monophosphate dehydrogenase | guaB | |
| Periplasmic maltose-binding protein | malE | |
| Putative extracellular ligand binding protein | | |
| Acid phosphatase | acpA | Extracellular |
| NADH-quinone oxidoreductase subunit F | nuoF | |
| Type VI secretion system | hcp-1 | Extracellular |
| 50S ribosomal protein L23 | rplW | |
| 50S ribosomal protein L6 | rplF | |
| 50S ribosomal protein L17 | rplQ | |
| Aconitate hydratase | | |

FIG. 9A

| Protein name | Gene | Accession | Peptide | AAACS | Conserv | iBCE-EL | Bepipred | Notes | Scores |
|---|---|---|---|---|---|---|---|---|---|
| Aminotransferase | aspC1 | Q5NGG1 | LPIDDAEK | -0.18 | 16/17 | 1.03 | 0.49 | | |
| Glutamate dehydrogenase | gdh | Q5NHR7 | FHPSVYSGIIK | -0.50 | 17/17 | 0.81 | 0.42 | Known antigen | |
| Pyruvate dehydrogenase acetyltransferase unit | aceF | Q5NEX3 | VSQGSLILK | 0.13 | 17/17 | 0.52 | 0.55 | Known antigen | |
| 60 kDa chaperonin | groL | Q5NE91 | DRVDDALHATR | -0.55 | 16/17 | 1.08 | 0.40 | Known antigen | |
| Chaperone protein DnaK | dnaK | Q5NFG7 | NTADNLIHSSR | 0.24 | 17/17 | 0.68 | 0.48 | Known antigen | |
| Chaperone protein DnaK | dnaK | Q5NFG7 | SSSGLSEEDIEK | -0.14 | 17/17 | 0.45 | 0.59 | Known antigen | |
| 60 kDa chaperonin | groL | Q5NE91 | DNTTIIDGAGEK | 0.22 | 16/17 | 0.64 | 0.52 | Known antigen | |
| 60 kDa chaperonin | groL | Q5NE91 | EGVITVEEGK | -0.63 | 16/17 | 0.25 | 0.49 | Known antigen | |
| Catalase-peroxidase | katG | Q5NGV7 | AVAQVYAENGNEQK | 0.02 | 17/17 | 0.33 | 0.49 | Known antigen | |
| Malate dehydrogenase | mdh | Q5NHC8 | FSGVPDNK | 0.50 | 17/17 | 1.06 | 0.48 | Known antigen | |
| Outer membrane protein 26 | omp26 | Q5NES2 | EIPADQLGTIK | 0.00 | 17/17 | 0.47 | 0.53 | OuterMembrane | |
| Succinate dehydrogenase flavoprotein subunit | sdhA | Q5NIJ3 | ITILATGGAGR | -0.58 | 17/17 | 0.65 | 0.36 | Known antigen | |
| ATP synthase subunit alpha | atpA | Q5NIK5 | GEVATDLTSPIEK | 0.96 | 16/17 | 0.48 | 0.58 | Known antigen | |
| Elongation factor Ts | tsf | Q5NHX9 | ESGKPAEIIEK | -0.32 | 17/17 | 0.54 | 0.53 | Known antigen | |
| Elongation factor Ts | tsf | Q5NHX9 | TVEAETLGAYIHGSK | 0.50 | 17/17 | 0.11 | 0.47 | Known antigen | |

FIG. 9B

| Protein | Gene | ID | Peptide | Value | Ratio | Val1 | Val2 | Status |
|---|---|---|---|---|---|---|---|---|
| Chaperone protein DnaK | dnaK | Q5NFG7 | IAGLEVK | -0.61 | 17/17 | 0.32 | 0.43 | Known antigen |
| Cell division protein FtsZ | ftsZ | Q5NI93 | KETEVVTGASNAPK | 1.32 | 17/17 | 0.44 | 0.65 | Known antigen |
| Trigger factor | tig | Q5NH48 | GGVDTFENEIK | 0.23 | 16/17 | 0.76 | 0.53 | |
| ATP synthase subunit alpha | atpA | Q5NIK5 | SVDQALQTGIK | -0.40 | 16/17 | 0.44 | 0.54 | Known antigen |
| Catalase-peroxidase | katG | Q5NGV7 | NDNLSPQSVDLSPLR | -0.16 | 17/17 | 0.21 | 0.55 | Known antigen |
| Isocitrate dehydrogenase [NADP] | idh | Q5NET6 | VADIELETK | 0.56 | 17/17 | 0.83 | 0.49 | Known antigen |
| Fructose-1,6-bisphosphate aldolase | fbaB | Q5NF78 | KINIDTDLR | -0.91 | 17/17 | 0.96 | 0.35 | Known antigen |
| Glutamate dehydrogenase | gdh | Q5NHR7 | GFVHDPEGITTDEK | 0.23 | 17/17 | 0.96 | 0.50 | Known antigen |
| Succinate–CoA ligase [ADP-forming] subunit beta | sucC | Q5NHF3 | PANFLDVGGGATK | -0.83 | 17/17 | 0.30 | 0.50 | Known antigen |
| Chaperone protein DnaK | dnaK | Q5NFG7 | KVPYAVIK | 0.67 | 17/17 | 0.27 | 0.50 | Known antigen |
| Malonyl CoA-acyl carrier protein transacylase | | Q5NF69 | EPTTAVVQNFDAK | 0.19 | 16/17 | 0.36 | 0.45 | Known antigen |
| Peroxiredoxin | | Q5NHA9 | KVPNVTFK | 0.04 | 17/17 | 0.80 | 0.48 | Known antigen |
| Chaperone protein DnaK | dnaK | Q5NFG7 | IINEPTAAALAYGVDSK | -0.80 | 17/17 | 1.23 | 0.38 | Known antigen |
| Conserved hypothetical lipoprotein | lpnA | Q5NGE4 | ATVYTTYNNNPQGSVR | -0.68 | 11/17 | 1.26 | 0.50 | Known antigen |
| Elongation factor Tu | tuf | Q5NID9 | TTVTGVEMFR | -0.24 | 17/17 | 0.45 | 0.45 | Known antigen |
| Succinate–CoA ligase [ADP- | sucC | Q5NHF3 | EVAESLIGK | 0.82 | 17/17 | 0.98 | 0.51 | Known antigen |

FIG. 9C

| Protein | Gene | UniProt | Peptide | AAACS | Conserv | iBCE-EL | Bepipred | Known antigen | | | | | |
|---|---|---|---|---|---|---|---|---|---|---|---|---|---|
| forming] subunit beta | | | | | | | | | 1 | | | | |
| 30S ribosomal protein S1 | rpsA | Q5NI98 | KIELWDR | 0.73 | 16/17 | 1.12 | 0.58 | Known antigen | | | | | |
| Elongation factor Tu | tuf | Q5NID9 | HYAHVDCPGHADYVK | -0.73 | 17/17 | 0.28 | 0.39 | Known antigen | | | | | |
| Transcription elongation factor GreA | greA | Q5NFC6 | IVGEDEADIDNQK | 0.08 | 17/17 | 0.70 | 0.53 | Known antigen | | | | | |
| 60 kDa chaperonin | groL | Q5NE91 | SFGTPTITK | -0.05 | 8/17 | 1.17 | 0.48 | Known antigen | | | | | 1 |
| Aconitate hydratase | acnA | Q5NII1 | GIPLVILAGK | -0.14 | 14/17 | 0.25 | 0.38 | Known antigen | 1 | | | | |
| Chaperone protein DnaK | dnaK | Q5NFG7 | AYAEQAQAAVAQGGAK | 2.21 | 11/17 | 0.23 | 0.36 | Known antigen | | | | 1 | |
| Chaperone protein DnaK | dnaK | Q5NFG7 | FHDLVTAR | 0.36 | 17/17 | 0.58 | 0.54 | Known antigen | | | | 1 | |
| Outer membrane protein 26 | omp26 | Q5NES2 | DGSVGWVK | -0.34 | 17/17 | 0.43 | 0.53 | | | | | | 1 |
| 3-oxoacyl-(Acyl-carrier-protein) reductase | fabG | Q5NF68 | VALVTGASR | -0.74 | 15/17 | 1.09 | 0.38 | | | | | | 2 |
| Chaperone protein DnaK | dnaK | Q5NFG7 | ALEDAGLSK | 0.30 | 17/17 | 0.79 | 0.48 | Known antigen | | | | | 2 |
| Enoyl-[acyl-carrier-protein] reductase [NADH] | fabI | Q5NGQ3 | TLAASGISNFK | -0.41 | 16/17 | 0.26 | 0.50 | | | | | | 2 |
| Aconitate hydratase | acnA | Q5NII1 | TAHTTTFEALAR | 0.95 | 16/17 | 0.63 | 0.46 | Known antigen | | | | | 2 |
| Elongation factor Ts | tsf | Q5NHX9 | LDVGEGIEK | -0.78 | 17/17 | 0.51 | 0.55 | Known antigen | | | | 2 | |

Shade: experiment>control. Numbers (1 and 2): experiment<control. Dark shade and number 2 indicate >2-fold difference. Proteins with multiple top scoring peptides are highlighted in bold. AAACS (average amino acid conservation score) values indicate the degree of conservation of a given peptide sequence with negative values corresponding to higher conservation. Conserv: conservation of the peptide in 17 F. tularensis strains with complete sequenced genomes. iBCE-EL: linear B-cell epitope prediction score by the iBCE-EL web server (score > 0.3 indicates a predicted B-cell epitope). Bepipred: linear B-cell epitope prediction score by the Bepipred 2.0 web server (score > 0.5 indicates a predicted B-cell epitope)

FIG. 10A

| Protein name | Gene | Accession | Peptide | AAACS | Conserv | iBCE-EL | Bepipred | Notes | Scores |
|---|---|---|---|---|---|---|---|---|---|
| Aspartate--tRNA(Asp/Asn) ligase | aspS | A0A0H3HT48 | TGAQDGDIFFAADR | 0.41 | 110/110 | 0.17 | 0.52 | | |
| Adenylosuccinate synthetase | purA | A0A0H3HJJ2 | QDQIGITLANVGK | 0.32 | 109/110 | 0.32 | 0.51 | | 1 |
| Dihydrolipoyl dehydrogenase | odhL | A0A0H3HQK7 | FPFSINGR | -0.57 | 110/110 | 1.14 | 0.31 | | 1 |
| Ankyrin repeat-containing protein | | A0A0H3HJC7 | IGDAPAPNAQK | 0.38 | 109/110 | 1.19 | 0.35 | | |
| Phosphoribosylformylglycinamidine synthase | purL | A0A0H3HPH9 | GATETFVVLPR | 0.94 | 108/110 | 0.54 | 0.40 | | |
| DNA-directed RNA polymerase subunit beta | rpoB | A0A0H3HT47 | STGPYSLVTQQPLGGK | -0.91 | 110/110 | 1.27 | 0.60 | | 1 |
| 50S ribosomal protein L6 | rplF | A0A0H3HQ22 | GYRPPEPYK | -0.35 | 109/110 | 1.41 | 0.58 | | |
| DNA-directed RNA polymerase subunit beta' | rpoC | A0A0H3HP07 | ISLYATTVGR | 0.48 | 110/110 | 0.50 | 0.57 | | |
| Enolase | eno | A0A0H3HLA6 | GIANSILIK | -0.30 | 110/110 | 0.46 | 0.40 | | 1 |
| Uncharacterized protein | | A0A0H3HWA2 | IDCLTNAYTAR | -0.09 | 103/110 | 0.68 | 0.46 | | 1 |
| DNA gyrase subunit A | gyrA | A0A0H3HKL0 | INVVLPVR | 0.07 | 19/110 | 0.57 | 0.36 | | |
| Aspartate-semialdehyde dehydrogenase | asd | A0A0H3HW74 | VTGTLSVPVGR | -0.36 | 110/110 | 0.50 | 0.41 | | |
| Malic enzyme | | A0A0H3HP28 | AALLSNSNFGSAPSASSR | 0.20 | 106/110 | 0.79 | 0.48 | | |
| 50S ribosomal protein L10 | rplJ | A0A0H3HUR4 | AQTVVLAEYR | -0.08 | 110/110 | 0.76 | 0.40 | | 1 |
| 50S ribosomal protein L6 | rplF | A0A0H3HQ22 | AHANAVHGVTK | -0.18 | 109/110 | 0.47 | 0.37 | | 1 |
| Glutamine synthetase | glnA | A0A0H3HL61 | ALNAITNPTTNSYK | -0.68 | 110/110 | 1.12 | 0.38 | | 1 |
| Nucleoside diphosphate kinase | ndk | A0A0H3HJK0 | NVIGQFYSR | 0.04 | 110/110 | 1.07 | 0.47 | Extracellular | 1 |

FIG. 10B

| | | | | | | | | | | | | | |
|---|---|---|---|---|---|---|---|---|---|---|---|---|---|
| Antioxidant protein LsfA | | A0A0H3HGZ9 | LIITYPASTGR | -0.55 | 110/110 | 0.51 | 0.55 | | | | | | |
| UDP-glucose 4-epimerase | | A0A0H3HFV2 | GYSVLEVVR | -0.23 | 107/110 | 0.53 | 0.45 | | | | | | |
| Enolase | eno | A0A0H3HLA6 | SAIVDIIGR | 0.40 | 110/110 | 0.53 | 0.38 | | | | | | |
| Acetyl-CoA acetyltransferase | | A0A0H3HTT4 | LPLSVGCTTINK | 0.12 | 109/110 | 0.22 | 0.42 | | | | | | |
| Adenosylhomocysteinase | ahcY | A0A0H3HP60 | SKFDNLYGCR | -0.70 | 110/110 | 0.82 | 0.42 | | | | | | |
| KHG/KDPG aldolase | eda | A0A0H3HGE0 | FGVSPGLTR | -0.35 | 110/110 | 0.38 | 0.43 | | | | | | |
| 10 kDa chaperonin | groES | A0A0H3HH83 | TASGIVIPDAAAEKPDQGEVLAIGPGKR | -0.24 | 109/110 | 0.62 | 0.49 | Known antigen | | | | | |
| Saccharopine dehydrogenase | | A0A0H3HIF5 | HGQLVQDVFTR | 0.21 | 110/110 | 0.79 | 0.47 | | | | | | |
| Citrate synthase | gltA | A0A0H3HYU5 | YSIGQPFVYPR | 0.28 | 110/110 | 1.27 | 0.54 | | | | | | |
| Aspartate--tRNA(Asp/Asn) ligase | aspS | A0A0H3HT48 | YVAAHHPFTSPK | -0.33 | 110/110 | 1.09 | 0.54 | | | | | | |
| Gamma-aminobutyraldehyde dehydrogenase | | A0A0H3HQU5 | SVLAAAAGNLK | 0.27 | 71/110 | 0.76 | 0.40 | | | | | | |
| Peptide chain release factor 2 | prfB | A0A0H3HL96 | SYVLDQSR | -0.31 | 109/110 | 0.72 | 0.61 | | | | | | |
| Polyketide non-ribosomal peptide synthase | | A0A0H3HWL5 | AWFIPLSAR | -0.12 | 100/110 | 0.85 | 0.35 | | | | | | |
| Transcription termination/antitermination protein | nusG | A0A0H3HPU8 | VTGFVGGAR | -0.36 | 110/110 | 0.61 | 0.43 | | | | | | |
| Beta sliding clamp | dnaN | A0A0H3HFM1 | FTFGQVELVSK | 0.15 | 110/110 | 0.51 | 0.41 | | | | | | |
| Malate synthase | aceB | A0A0H3HIT5 | IATLIVRPK | -0.55 | 110/110 | 0.61 | 0.36 | | | | | | |
| PTS system, EIIA component | | A0A0H3HRL4 | ISGHHLEVTPAIR | -0.41 | 110/110 | 0.78 | 0.47 | | | | | | |
| Phosphoenolpyruvate synthase | ppsA | A0A0H3HJ13 | IFILQARPETVK | -0.67 | 109/110 | 0.31 | 0.50 | | | | | | |
| Thiol:disulfide interchange protein | dsbA | A0A0H3HTS6 | NYNIDGVPTIVVQGK | -0.52 | 110/110 | 0.30 | 0.46 | | | | | | |

FIG. 10C

| Protein | Gene | UniProt | Peptide | AAACS | Conserv | iBCE-EL | Bepipred | Location | | | | | |
|---|---|---|---|---|---|---|---|---|---|---|---|---|---|
| RND family efflux transporter MFP subunit | bpeA | A0A0H3HQZ3 | AQANLATQNAL VAR | 0.04 | 109/110 | 0.34 | 0.53 | | | | | | |
| Inosine-5'-monophosphate dehydrogenase | guaB | A0A0H3HJ23 | LVGIVTNR | -0.57 | 100/110 | 0.59 | 0.37 | | | | | | |
| Periplasmic maltose-binding protein | malE | A0A0H3HG39 | VNWLYINK | -0.59 | 110/110 | 1.13 | 0.36 | | | | | | |
| Putative extracellular ligand binding protein | | A0A0H3HWC6 | VVATDAQQGPA LADYAK | -0.16 | 110/110 | 1.27 | 0.41 | | | | | | |
| Acid phosphatase | acpA | A0A0H3HV11 | NIVVIYAENR | -0.78 | 110/110 | 0.67 | 0.34 | Extracellular | | | | 1 | |
| NADH-quinone oxidoreductase subunit F | nuoF | A0A0H3HPW5 | EGTGWLYR | -0.09 | 110/110 | 0.36 | 0.43 | | | | | | |
| Type VI secretion system | hcp-1 | A0A0H3HE88 | IGGNQGGNTQG AWSLTK | 0.19 | 110/110 | 1.33 | 0.58 | Extracellular | | | | | |
| 50S ribosomal protein L23 | rplW | A0A0H3HT35 | AAVELLFK | -0.06 | 110/110 | 0.23 | 0.45 | | | | | | |
| 50S ribosomal protein L6 | rplF | A0A0H3HQ22 | LTLVGVGYR | -0.73 | 105/110 | 0.70 | 0.44 | | | | | | |
| 50S ribosomal protein L17 | rplQ | A0A0H3HPQ2 | LFDVLGPR | -0.01 | 110/110 | 0.44 | 0.44 | | | | | | |
| Aconitate hydratase | | A0A0H3HVV9 | IVLESVLR | -0.62 | 110/110 | 0.36 | 0.31 | | | | | | |

Shade: experimental sample>control. Numbers (1 and 2): experimental sample>control. Dark shade and number 2 indicate >2-fold difference. Proteins with multiple top scoring peptides are highlighted in bold. AAACS (average amino acid conservation score) values indicate the degree of conservation of a given peptide sequence with negative values corresponding to higher conservation. Conserv: conservation of the peptide in 110 B. pseudomallei strains with complete sequenced genomes. iBCE-EL: linear B-cell epitope prediction score by the iBCE-EL web server (score > 0.3 indicates a predicted B-cell epitope). Bepipred: linear B-cell epitope prediction score by the Bepipred 2.0 web server (score > 0.5 indicates a predicted B-cell epitope).

SEQUENCE LISTING

```
<160> NUMBER OF SEQ ID NOS: 101

<210> SEQ ID NO 1
<211> LENGTH: 8
<212> TYPE: PRT
<213> ORGANISM: Francisella tularensis

<400> SEQUENCE: 1

Leu Pro Ile Asp Asp Ala Glu Lys
1               5

<210> SEQ ID NO 2
<211> LENGTH: 11
<212> TYPE: PRT
<213> ORGANISM: Francisella tularensis

<400> SEQUENCE: 2

Phe His Pro Ser Val Tyr Ser Gly Ile Ile Lys
1               5                   10

<210> SEQ ID NO 3
<211> LENGTH: 9
<212> TYPE: PRT
<213> ORGANISM: Francisella tularensis

<400> SEQUENCE: 3

Val Ser Gln Gly Ser Leu Ile Leu Lys
1               5

<210> SEQ ID NO 4
<211> LENGTH: 11
<212> TYPE: PRT
<213> ORGANISM: Francisella tularensis
```

<400> SEQUENCE: 4

Asp Arg Val Asp Ala Leu His Ala Thr Arg
1               5                   10

<210> SEQ ID NO 5
<211> LENGTH: 11
<212> TYPE: PRT
<213> ORGANISM: Francisella tularensis

<400> SEQUENCE: 5

Asn Thr Ala Asp Asn Leu Ile His Ser Ser Arg
1               5                   10

<210> SEQ ID NO 6
<211> LENGTH: 12
<212> TYPE: PRT
<213> ORGANISM: Francisella tularensis

<400> SEQUENCE: 6

Ser Ser Ser Gly Leu Ser Glu Glu Asp Ile Glu Lys
1               5                   10

<210> SEQ ID NO 7
<211> LENGTH: 12
<212> TYPE: PRT
<213> ORGANISM: Francisella tularensis

<400> SEQUENCE: 7

Asp Asn Thr Thr Ile Ile Asp Gly Ala Gly Glu Lys
1               5                   10

<210> SEQ ID NO 8
<211> LENGTH: 10
<212> TYPE: PRT
<213> ORGANISM: Francisella tularensis

<400> SEQUENCE: 8

Glu Gly Val Ile Thr Val Glu Glu Gly Lys
1               5                   10

<210> SEQ ID NO 9
<211> LENGTH: 14
<212> TYPE: PRT
<213> ORGANISM: Francisella tularensis

<400> SEQUENCE: 9

Ala Val Ala Gln Val Tyr Ala Glu Asn Gly Asn Glu Gln Lys
1               5                   10

<210> SEQ ID NO 10
<211> LENGTH: 8
<212> TYPE: PRT
<213> ORGANISM: Francisella tularensis

<400> SEQUENCE: 10

Phe Ser Gly Val Pro Asp Asn Lys
1               5

<210> SEQ ID NO 11
<211> LENGTH: 11
<212> TYPE: PRT
<213> ORGANISM: Francisella tularensis

<400> SEQUENCE: 11

```
Glu Ile Pro Ala Asp Gln Leu Gly Thr Ile Lys
1               5                   10

<210> SEQ ID NO 12
<211> LENGTH: 11
<212> TYPE: PRT
<213> ORGANISM: Francisella tularensis

<400> SEQUENCE: 12

Ile Thr Ile Leu Ala Thr Gly Gly Ala Gly Arg
1               5                   10

<210> SEQ ID NO 13
<211> LENGTH: 13
<212> TYPE: PRT
<213> ORGANISM: Francisella tularensis

<400> SEQUENCE: 13

Gly Glu Val Ala Thr Asp Leu Thr Ser Pro Ile Glu Lys
1               5                   10

<210> SEQ ID NO 14
<211> LENGTH: 11
<212> TYPE: PRT
<213> ORGANISM: Francisella tularensis

<400> SEQUENCE: 14

Glu Ser Gly Lys Pro Ala Glu Ile Ile Glu Lys
1               5                   10

<210> SEQ ID NO 15
<211> LENGTH: 15
<212> TYPE: PRT
<213> ORGANISM: Francisella tularensis

<400> SEQUENCE: 15

Thr Val Glu Ala Glu Thr Leu Gly Ala Tyr Ile His Gly Ser Lys
1               5                   10                  15

<210> SEQ ID NO 16
<211> LENGTH: 7
<212> TYPE: PRT
<213> ORGANISM: Francisella tularensis

<400> SEQUENCE: 16

Ile Ala Gly Leu Glu Val Lys
1               5

<210> SEQ ID NO 17
<211> LENGTH: 14
<212> TYPE: PRT
<213> ORGANISM: Francisella tularensis

<400> SEQUENCE: 17

Lys Glu Thr Glu Val Val Thr Gly Ala Ser Asn Ala Pro Lys
1               5                   10

<210> SEQ ID NO 18
<211> LENGTH: 11
<212> TYPE: PRT
<213> ORGANISM: Francisella tularensis

<400> SEQUENCE: 18

Gly Gly Val Asp Thr Phe Glu Asn Glu Ile Lys
```

```
1               5                   10
```

```
<210> SEQ ID NO 19
<211> LENGTH: 11
<212> TYPE: PRT
<213> ORGANISM: Francisella tularensis

<400> SEQUENCE: 19

Ser Val Asp Gln Ala Leu Gln Thr Gly Ile Lys
1               5                   10

<210> SEQ ID NO 20
<211> LENGTH: 15
<212> TYPE: PRT
<213> ORGANISM: Francisella tularensis

<400> SEQUENCE: 20

Asn Asp Asn Leu Ser Pro Gln Ser Val Asp Leu Ser Pro Leu Arg
1               5                   10                  15

<210> SEQ ID NO 21
<211> LENGTH: 9
<212> TYPE: PRT
<213> ORGANISM: Francisella tularensis

<400> SEQUENCE: 21

Val Ala Asp Ile Glu Leu Glu Thr Lys
1               5

<210> SEQ ID NO 22
<211> LENGTH: 9
<212> TYPE: PRT
<213> ORGANISM: Francisella tularensis

<400> SEQUENCE: 22

Lys Ile Asn Ile Asp Thr Asp Leu Arg
1               5

<210> SEQ ID NO 23
<211> LENGTH: 14
<212> TYPE: PRT
<213> ORGANISM: Francisella tularensis

<400> SEQUENCE: 23

Gly Phe Val His Asp Pro Glu Gly Ile Thr Thr Asp Glu Lys
1               5                   10

<210> SEQ ID NO 24
<211> LENGTH: 13
<212> TYPE: PRT
<213> ORGANISM: Francisella tularensis

<400> SEQUENCE: 24

Pro Ala Asn Phe Leu Asp Val Gly Gly Gly Ala Thr Lys
1               5                   10

<210> SEQ ID NO 25
<211> LENGTH: 8
<212> TYPE: PRT
<213> ORGANISM: Francisella tularensis

<400> SEQUENCE: 25

Lys Val Pro Tyr Ala Val Ile Lys
1               5
```

```
<210> SEQ ID NO 26
<211> LENGTH: 13
<212> TYPE: PRT
<213> ORGANISM: Francisella tularensis

<400> SEQUENCE: 26

Glu Pro Thr Thr Ala Val Val Gln Asn Phe Asp Ala Lys
1               5                   10

<210> SEQ ID NO 27
<211> LENGTH: 8
<212> TYPE: PRT
<213> ORGANISM: Francisella tularensis

<400> SEQUENCE: 27

Lys Val Pro Asn Val Thr Phe Lys
1               5

<210> SEQ ID NO 28
<211> LENGTH: 17
<212> TYPE: PRT
<213> ORGANISM: Francisella tularensis

<400> SEQUENCE: 28

Ile Ile Asn Glu Pro Thr Ala Ala Ala Leu Ala Tyr Gly Val Asp Ser
1               5                   10                  15

Lys

<210> SEQ ID NO 29
<211> LENGTH: 16
<212> TYPE: PRT
<213> ORGANISM: Francisella tularensis

<400> SEQUENCE: 29

Ala Thr Val Tyr Thr Thr Tyr Asn Asn Asn Pro Gln Gly Ser Val Arg
1               5                   10                  15

<210> SEQ ID NO 30
<211> LENGTH: 10
<212> TYPE: PRT
<213> ORGANISM: Francisella tularensis

<400> SEQUENCE: 30

Thr Thr Val Thr Gly Val Glu Met Phe Arg
1               5                   10

<210> SEQ ID NO 31
<211> LENGTH: 9
<212> TYPE: PRT
<213> ORGANISM: Francisella tularensis

<400> SEQUENCE: 31

Glu Val Ala Glu Ser Leu Ile Gly Lys
1               5

<210> SEQ ID NO 32
<211> LENGTH: 7
<212> TYPE: PRT
<213> ORGANISM: Francisella tularensis

<400> SEQUENCE: 32

Lys Ile Glu Leu Trp Asp Arg
1               5
```

```
<210> SEQ ID NO 33
<211> LENGTH: 15
<212> TYPE: PRT
<213> ORGANISM: Francisella tularensis

<400> SEQUENCE: 33

His Tyr Ala His Val Asp Cys Pro Gly His Ala Asp Tyr Val Lys
1               5                   10                  15

<210> SEQ ID NO 34
<211> LENGTH: 13
<212> TYPE: PRT
<213> ORGANISM: Francisella tularensis

<400> SEQUENCE: 34

Ile Val Gly Glu Asp Glu Ala Asp Ile Asp Asn Gln Lys
1               5                   10

<210> SEQ ID NO 35
<211> LENGTH: 9
<212> TYPE: PRT
<213> ORGANISM: Francisella tularensis

<400> SEQUENCE: 35

Ser Phe Gly Thr Pro Thr Ile Thr Lys
1               5

<210> SEQ ID NO 36
<211> LENGTH: 10
<212> TYPE: PRT
<213> ORGANISM: Francisella tularensis

<400> SEQUENCE: 36

Gly Ile Pro Leu Val Ile Leu Ala Gly Lys
1               5                   10

<210> SEQ ID NO 37
<211> LENGTH: 16
<212> TYPE: PRT
<213> ORGANISM: Francisella tularensis

<400> SEQUENCE: 37

Ala Tyr Ala Glu Gln Ala Gln Ala Ala Val Ala Gln Gly Gly Ala Lys
1               5                   10                  15

<210> SEQ ID NO 38
<211> LENGTH: 8
<212> TYPE: PRT
<213> ORGANISM: Francisella tularensis

<400> SEQUENCE: 38

Phe His Asp Leu Val Thr Ala Arg
1               5

<210> SEQ ID NO 39
<211> LENGTH: 8
<212> TYPE: PRT
<213> ORGANISM: Francisella tularensis

<400> SEQUENCE: 39

Asp Gly Ser Val Gly Trp Val Lys
1               5

<210> SEQ ID NO 40
```

```
<211> LENGTH: 9
<212> TYPE: PRT
<213> ORGANISM: Francisella tularensis

<400> SEQUENCE: 40

Val Ala Leu Val Thr Gly Ala Ser Arg
1               5

<210> SEQ ID NO 41
<211> LENGTH: 9
<212> TYPE: PRT
<213> ORGANISM: Francisella tularensis

<400> SEQUENCE: 41

Ala Leu Glu Asp Ala Gly Leu Ser Lys
1               5

<210> SEQ ID NO 42
<211> LENGTH: 11
<212> TYPE: PRT
<213> ORGANISM: Francisella tularensis

<400> SEQUENCE: 42

Thr Leu Ala Ala Ser Gly Ile Ser Asn Phe Lys
1               5                   10

<210> SEQ ID NO 43
<211> LENGTH: 12
<212> TYPE: PRT
<213> ORGANISM: Francisella tularensis

<400> SEQUENCE: 43

Thr Ala His Thr Thr Thr Phe Glu Ala Leu Ala Arg
1               5                   10

<210> SEQ ID NO 44
<211> LENGTH: 9
<212> TYPE: PRT
<213> ORGANISM: Francisella tularensis

<400> SEQUENCE: 44

Leu Asp Val Gly Glu Gly Ile Glu Lys
1               5

<210> SEQ ID NO 45
<211> LENGTH: 15
<212> TYPE: PRT
<213> ORGANISM: Burkholderia pseudomallei

<400> SEQUENCE: 45

Thr Gly Ala Gln Asp Gly Asp Ile Ile Phe Phe Ala Ala Asp Arg
1               5                   10                  15

<210> SEQ ID NO 46
<211> LENGTH: 13
<212> TYPE: PRT
<213> ORGANISM: Burkholderia pseudomallei

<400> SEQUENCE: 46

Gln Asp Gln Ile Gly Ile Thr Leu Ala Asn Val Gly Lys
1               5                   10

<210> SEQ ID NO 47
<211> LENGTH: 8
<212> TYPE: PRT
```

<213> ORGANISM: Burkholderia pseudomallei

<400> SEQUENCE: 47

Phe Pro Phe Ser Ile Asn Gly Arg
1               5

<210> SEQ ID NO 48
<211> LENGTH: 11
<212> TYPE: PRT
<213> ORGANISM: Burkholderia pseudomallei

<400> SEQUENCE: 48

Ile Gly Asp Ala Pro Ala Pro Asn Ala Gln Lys
1               5                   10

<210> SEQ ID NO 49
<211> LENGTH: 11
<212> TYPE: PRT
<213> ORGANISM: Burkholderia pseudomallei

<400> SEQUENCE: 49

Gly Ala Thr Glu Thr Phe Val Val Leu Pro Arg
1               5                   10

<210> SEQ ID NO 50
<211> LENGTH: 16
<212> TYPE: PRT
<213> ORGANISM: Burkholderia pseudomallei

<400> SEQUENCE: 50

Ser Thr Gly Pro Tyr Ser Leu Val Thr Gln Gln Pro Leu Gly Gly Lys
1               5                   10                  15

<210> SEQ ID NO 51
<211> LENGTH: 9
<212> TYPE: PRT
<213> ORGANISM: Burkholderia pseudomallei

<400> SEQUENCE: 51

Gly Tyr Arg Pro Pro Glu Pro Tyr Lys
1               5

<210> SEQ ID NO 52
<211> LENGTH: 10
<212> TYPE: PRT
<213> ORGANISM: Burkholderia pseudomallei

<400> SEQUENCE: 52

Ile Ser Leu Tyr Ala Thr Thr Val Gly Arg
1               5                   10

<210> SEQ ID NO 53
<211> LENGTH: 9
<212> TYPE: PRT
<213> ORGANISM: Burkholderia pseudomallei

<400> SEQUENCE: 53

Gly Ile Ala Asn Ser Ile Leu Ile Lys
1               5

<210> SEQ ID NO 54
<211> LENGTH: 11
<212> TYPE: PRT
<213> ORGANISM: Burkholderia pseudomallei

<400> SEQUENCE: 54

Ile Asp Cys Leu Thr Asn Ala Tyr Thr Ala Arg
1               5                   10

<210> SEQ ID NO 55
<211> LENGTH: 8
<212> TYPE: PRT
<213> ORGANISM: Burkholderia pseudomallei

<400> SEQUENCE: 55

Ile Asn Val Val Leu Pro Val Arg
1               5

<210> SEQ ID NO 56
<211> LENGTH: 11
<212> TYPE: PRT
<213> ORGANISM: Burkholderia pseudomallei

<400> SEQUENCE: 56

Val Thr Gly Thr Leu Ser Val Pro Val Gly Arg
1               5                   10

<210> SEQ ID NO 57
<211> LENGTH: 18
<212> TYPE: PRT
<213> ORGANISM: Burkholderia pseudomallei

<400> SEQUENCE: 57

Ala Ala Leu Leu Ser Asn Ser Asn Phe Gly Ser Ala Pro Ser Ala Ser
1               5                   10                  15

Ser Arg

<210> SEQ ID NO 58
<211> LENGTH: 10
<212> TYPE: PRT
<213> ORGANISM: Burkholderia pseudomallei

<400> SEQUENCE: 58

Ala Gln Thr Val Val Leu Ala Glu Tyr Arg
1               5                   10

<210> SEQ ID NO 59
<211> LENGTH: 12
<212> TYPE: PRT
<213> ORGANISM: Burkholderia pseudomallei

<400> SEQUENCE: 59

Ala Ile Ile Ala Asn Ala Val His Gly Val Thr Lys
1               5                   10

<210> SEQ ID NO 60
<211> LENGTH: 14
<212> TYPE: PRT
<213> ORGANISM: Burkholderia pseudomallei

<400> SEQUENCE: 60

Ala Leu Asn Ala Ile Thr Asn Pro Thr Thr Asn Ser Tyr Lys
1               5                   10

<210> SEQ ID NO 61
<211> LENGTH: 9
<212> TYPE: PRT
<213> ORGANISM: Burkholderia pseudomallei

```
<400> SEQUENCE: 61

Asn Val Ile Gly Gln Ile Tyr Ser Arg
1               5

<210> SEQ ID NO 62
<211> LENGTH: 11
<212> TYPE: PRT
<213> ORGANISM: Burkholderia pseudomallei

<400> SEQUENCE: 62

Leu Ile Ile Thr Tyr Pro Ala Ser Thr Gly Arg
1               5                   10

<210> SEQ ID NO 63
<211> LENGTH: 9
<212> TYPE: PRT
<213> ORGANISM: Burkholderia pseudomallei

<400> SEQUENCE: 63

Gly Tyr Ser Val Leu Glu Val Val Arg
1               5

<210> SEQ ID NO 64
<211> LENGTH: 9
<212> TYPE: PRT
<213> ORGANISM: Burkholderia pseudomallei

<400> SEQUENCE: 64

Ser Ala Ile Val Asp Ile Ile Gly Arg
1               5

<210> SEQ ID NO 65
<211> LENGTH: 12
<212> TYPE: PRT
<213> ORGANISM: Burkholderia pseudomallei

<400> SEQUENCE: 65

Leu Pro Leu Ser Val Gly Cys Thr Thr Ile Asn Lys
1               5                   10

<210> SEQ ID NO 66
<211> LENGTH: 10
<212> TYPE: PRT
<213> ORGANISM: Burkholderia pseudomallei

<400> SEQUENCE: 66

Ser Lys Phe Asp Asn Leu Tyr Gly Cys Arg
1               5                   10

<210> SEQ ID NO 67
<211> LENGTH: 9
<212> TYPE: PRT
<213> ORGANISM: Burkholderia pseudomallei

<400> SEQUENCE: 67

Phe Gly Val Ser Pro Gly Leu Thr Arg
1               5

<210> SEQ ID NO 68
<211> LENGTH: 28
<212> TYPE: PRT
<213> ORGANISM: Burkholderia pseudomallei

<400> SEQUENCE: 68
```

```
Thr Ala Ser Gly Ile Val Ile Pro Asp Ala Ala Glu Lys Pro Asp
1               5                   10                  15

Gln Gly Glu Val Leu Ala Ile Gly Pro Gly Lys Arg
            20                  25
```

<210> SEQ ID NO 69
<211> LENGTH: 11
<212> TYPE: PRT
<213> ORGANISM: Burkholderia pseudomallei

<400> SEQUENCE: 69

```
His Gly Gln Leu Val Gln Asp Val Phe Thr Arg
1               5                   10
```

<210> SEQ ID NO 70
<211> LENGTH: 11
<212> TYPE: PRT
<213> ORGANISM: Burkholderia pseudomallei

<400> SEQUENCE: 70

```
Tyr Ser Ile Gly Gln Pro Phe Val Tyr Pro Arg
1               5                   10
```

<210> SEQ ID NO 71
<211> LENGTH: 12
<212> TYPE: PRT
<213> ORGANISM: Burkholderia pseudomallei

<400> SEQUENCE: 71

```
Tyr Val Ala Ala His His Pro Phe Thr Ser Pro Lys
1               5                   10
```

<210> SEQ ID NO 72
<211> LENGTH: 11
<212> TYPE: PRT
<213> ORGANISM: Burkholderia pseudomallei

<400> SEQUENCE: 72

```
Ser Val Leu Ala Ala Ala Ala Gly Asn Leu Lys
1               5                   10
```

<210> SEQ ID NO 73
<211> LENGTH: 8
<212> TYPE: PRT
<213> ORGANISM: Burkholderia pseudomallei

<400> SEQUENCE: 73

```
Ser Tyr Val Leu Asp Gln Ser Arg
1               5
```

<210> SEQ ID NO 74
<211> LENGTH: 9
<212> TYPE: PRT
<213> ORGANISM: Burkholderia pseudomallei

<400> SEQUENCE: 74

```
Ala Trp Phe Ile Pro Leu Ser Ala Arg
1               5
```

<210> SEQ ID NO 75
<211> LENGTH: 9
<212> TYPE: PRT
<213> ORGANISM: Burkholderia pseudomallei

<400> SEQUENCE: 75

Val Thr Gly Phe Val Gly Gly Ala Arg
1               5

<210> SEQ ID NO 76
<211> LENGTH: 11
<212> TYPE: PRT
<213> ORGANISM: Burkholderia pseudomallei

<400> SEQUENCE: 76

Phe Thr Phe Gly Gln Val Glu Leu Val Ser Lys
1               5                   10

<210> SEQ ID NO 77
<211> LENGTH: 9
<212> TYPE: PRT
<213> ORGANISM: Burkholderia pseudomallei

<400> SEQUENCE: 77

Ile Ala Thr Leu Ile Val Arg Pro Arg
1               5

<210> SEQ ID NO 78
<211> LENGTH: 13
<212> TYPE: PRT
<213> ORGANISM: Burkholderia pseudomallei

<400> SEQUENCE: 78

Ile Ser Gly His His Leu Glu Val Thr Pro Ala Ile Arg
1               5                   10

<210> SEQ ID NO 79
<211> LENGTH: 12
<212> TYPE: PRT
<213> ORGANISM: Burkholderia pseudomallei

<400> SEQUENCE: 79

Ile Phe Ile Leu Gln Ala Arg Pro Glu Thr Val Lys
1               5                   10

<210> SEQ ID NO 80
<211> LENGTH: 15
<212> TYPE: PRT
<213> ORGANISM: Burkholderia pseudomallei

<400> SEQUENCE: 80

Asn Tyr Asn Ile Asp Gly Val Pro Thr Ile Val Val Gln Gly Lys
1               5                   10                  15

<210> SEQ ID NO 81
<211> LENGTH: 14
<212> TYPE: PRT
<213> ORGANISM: Burkholderia pseudomallei

<400> SEQUENCE: 81

Ala Gln Ala Asn Leu Ala Thr Gln Asn Ala Leu Val Ala Arg
1               5                   10

<210> SEQ ID NO 82
<211> LENGTH: 8
<212> TYPE: PRT
<213> ORGANISM: Burkholderia pseudomallei

<400> SEQUENCE: 82

Leu Val Gly Ile Val Thr Asn Arg
1               5

```
<210> SEQ ID NO 83
<211> LENGTH: 8
<212> TYPE: PRT
<213> ORGANISM: Burkholderia pseudomallei

<400> SEQUENCE: 83

Val Asn Trp Leu Tyr Ile Asn Lys
1               5

<210> SEQ ID NO 84
<211> LENGTH: 17
<212> TYPE: PRT
<213> ORGANISM: Burkholderia pseudomallei

<400> SEQUENCE: 84

Val Val Ala Thr Asp Ala Gln Gln Gly Pro Ala Leu Ala Asp Tyr Ala
1               5                   10                  15

Lys

<210> SEQ ID NO 85
<211> LENGTH: 10
<212> TYPE: PRT
<213> ORGANISM: Burkholderia pseudomallei

<400> SEQUENCE: 85

Asn Ile Val Val Ile Tyr Ala Glu Asn Arg
1               5                   10

<210> SEQ ID NO 86
<211> LENGTH: 8
<212> TYPE: PRT
<213> ORGANISM: Burkholderia pseudomallei

<400> SEQUENCE: 86

Glu Gly Thr Gly Trp Leu Tyr Arg
1               5

<210> SEQ ID NO 87
<211> LENGTH: 17
<212> TYPE: PRT
<213> ORGANISM: Burkholderia pseudomallei

<400> SEQUENCE: 87

Ile Gly Gly Asn Gln Gly Gly Asn Thr Gln Gly Ala Trp Ser Leu Thr
1               5                   10                  15

Lys

<210> SEQ ID NO 88
<211> LENGTH: 8
<212> TYPE: PRT
<213> ORGANISM: Burkholderia pseudomallei

<400> SEQUENCE: 88

Ala Ala Val Glu Leu Leu Phe Lys
1               5

<210> SEQ ID NO 89
<211> LENGTH: 9
<212> TYPE: PRT
<213> ORGANISM: Burkholderia pseudomallei

<400> SEQUENCE: 89
```

```
Leu Thr Leu Val Gly Val Gly Tyr Arg
1               5
```

<210> SEQ ID NO 90
<211> LENGTH: 8
<212> TYPE: PRT
<213> ORGANISM: Burkholderia pseudomallei

<400> SEQUENCE: 90

```
Leu Phe Asp Val Leu Gly Pro Arg
1               5
```

<210> SEQ ID NO 91
<211> LENGTH: 8
<212> TYPE: PRT
<213> ORGANISM: Burkholderia pseudomallei

<400> SEQUENCE: 91

```
Ile Val Leu Glu Ser Val Leu Arg
1               5
```

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Gly Pro Ser Leu Lys Leu
1               5
```

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Gly Pro Ser Leu
1
```

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

```
Pro Ser Leu Lys
1
```

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

```
Gly Pro Ser Leu Lys
1               5

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Leu Lys Leu
1

<210> SEQ ID NO 97
<211> LENGTH: 22
<212> TYPE: PRT
<213> ORGANISM: Francisella tularensis

<400> SEQUENCE: 97

Asn Thr Thr Ile Ile Asp Gly Ala Gly Glu Lys Glu Ala Ile Ala Lys
1               5                   10                  15

Arg Ile Asn Val Ile Lys
            20

<210> SEQ ID NO 98
<211> LENGTH: 13
<212> TYPE: PRT
<213> ORGANISM: Francisella tularensis

<400> SEQUENCE: 98

Ser Glu Asp Leu Ser Met Lys Leu Glu Glu Thr Asn Met
1               5                   10

<210> SEQ ID NO 99
<211> LENGTH: 15
<212> TYPE: PRT
<213> ORGANISM: Francisella tularensis

<400> SEQUENCE: 99

Asn Thr Thr Ile Ile Asp Gly Ala Gly Glu Lys Glu Ala Ile Ala
1               5                   10                  15

<210> SEQ ID NO 100
<211> LENGTH: 5
<212> TYPE: PRT
<213> ORGANISM: Francisella tularensis

<400> SEQUENCE: 100

Phe Glu Asp Glu Leu
1               5

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
```

```
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 101

Xaa Cys Cys Xaa Pro Ala Cys Gly Xaa Xaa Xaa Xaa Cys Xaa
1               5                   10
```

METHODS FOR RAPID DETECTION OF IMMUNOGENIC EPITOPES IN BIOTHREAT AGENTS AND EMERGING PATHOGENS FOR PEPTIDE VACCINES AND THERAPEUTICS

BACKGROUND

The following description of the background of the present technology is provided simply as an aid in understanding the present technology and is not admitted to describe or constitute prior art to the present technology.

Peptide-based vaccines represent the next generation of vaccines, with great potential for providing rapid protection against biothreats and emerging pathogens. Peptide vaccine formulations consist of multiple synthetic linear epitopes that together trigger immune responses resulting in robust immune memory. This multi-epitope approach can be broadly protective across divergent strains. Due to their simple structure, peptides can be easily synthesized, multiplexed into vaccine formulations, and efficiently screened for efficacy. Consequently, peptide-based vaccines represent promising candidates for rapid response countermeasures. The first universal influenza vaccine to enter phase III clinical trials is a peptide vaccine. In addition, the multi-epitope approach can be effective for pathogens with complex life cycles, such as *Plasmodium falciparum*. Indeed, several malaria peptide vaccines are currently in clinical trials (Li et al. 2014, Malonis, Lai, and Vergnolle 2020, Skwarczynski and Toth 2016).

Current strategies for epitope identification depend upon detection of epitopes within an individual full-length protein, a low-throughput approach that requires prior knowledge of the antigenic protein and its sequence. Technologies to screen for epitopes at the whole proteome level have been developed such as proteomic microarrays, phage and yeast display. However, these technologies require extensive use of synthetic biology and other time-consuming methodologies such as library construction, peptide/protein array preparation, heterologous protein expression. (Dudek et al. 2010, Skwarczynski and Toth 2016, Wang et al. 2018, Zhao et al. 2018, Bi et al. 2019, Jaenisch et al. 2019). Another major disadvantage of display technologies and use of non-native expression systems is that these methods do not reliably replicate the native properties of the antigenic proteins, including their post-translational modifications, which can lead to inaccurate results.

Development of an effective vaccine against a biothreat agent or emerging pathogen is a costly and cumbersome process that can take years to decades to complete. The identification of antigens that stimulate protective immunity against a pathogen can represent a significant bottleneck in the typical vaccine development process known to the art, especially for bacterial or fungal pathogens, eukaryotic parasites, or even large DNA viruses, which can contain hundreds to thousands of potential antigens. Accordingly, there is a need for a rapid, an accelerated and efficient process for identifying immunoreactive peptides for the development of peptide vaccines and therapeutics. The present disclosure addresses that need by providing a novel and unique high-throughput platform for rapid and efficient identification of immunoreactive peptides that could be utilized as candidates for the development of peptide-based vaccines.

SUMMARY OF THE DISCLOSURE

The present disclosure provides a newly developed generalizable screening method that enables efficient identification of epitopes, e.g., B cell epitopes in the proteomes of pathogenic agent. In one aspect, the present disclosure is based, in part, on the discovery of a proteome-wide screening method for identifying immunoreactive peptides using native proteomes isolated from pathogens of interest that were screened against convalescent sera from animals immunized with said pathogens. This strategy has several advantages over currently available methods for epitope discovery. First, this novel process does not require prior knowledge of antigenicity or antigen structure. Second, this novel process is quick and efficient and obviates the need for complex and laborious experimental techniques such as preparation of display libraries and heterologous protein expression.

The novel process of the present disclosure is designed to enable the efficient identification of the protein antigen and, importantly, the antigenic regions (epitopes) within identified antigens, such that these short linear peptides can be immediately synthesized and used in peptide vaccine formulations and therapeutics.

In one aspect, a method of identifying an immunogenic peptide is provided, comprising: (a) identifying an interactive peptide by contacting a peptide library generated from a pathogenic agent with purified peptide-specific immunoglobulins under conditions to form peptide-immunoglobulin complexes between the interactive peptides and the specific immunoglobulins and identifying one or more interactive peptides bound to the peptide-immunoglobulin complexes; and (b) comparing the identified interactive peptides of step (a) to peptides bound to control immunoglobulins, and selecting at least one identified peptide of step (a) that does not bind to the control immunoglobulins or is enriched in the interactive peptides of step (a) as compared to the peptide bound to control immunoglobulins, thereby identifying an immunogenic peptide.

In one aspect, the interactive peptides of step (a) are obtained from one or more of convalescent sera or from sera or plasma collected from a subject who was immunized with or exposed to the pathogen. In another aspect, the control immunoglobulins are obtained from sera or plasma from a subject who was not exposed to or immunized with the pathogenic agent. In a yet further aspect, the pathogenic agent is selected from a bacterium, a fungus, a DNA virus, an RNA virus, an arenavirus, a bunyavirus, an hantavirus, a flavirus, a parasitic worm, a filovirus, a protozoa, a virulent strain or an attenuated strain of the pathogenic agent.

In some embodiments, the pathogenic agent is selected from: *Bacillus anthracis, Clostridium botulinum, Yersinia pestis, Variola major* and other pox viruses, *Francisella tularensis*, human papilloma virus, West Nile virus, *Burkholderia pseudomallei, Mycobacterium tuberculosis, Toxoplasma gondii, Plasmodium falciparum* LCM, Junin virus, Machupo virus, Guanarito virus, Lassa Fever, Rift Valley Fever virus, Dengue, Ebola virus, Marburg virus, *Coxiella burnetii* (Q fever), *Brucella* species (brucellosis), *Burkholderia mallei* (glanders), Ricin toxin (from *Ricinus communis*), Epsilon toxin of *Clostridium perfringens, Staphylococcus* enterotoxin B, Typhus fever, *Rickettsia prowazekii*, Diarrheagenic *Escherichia coli*, Pathogenic Vibrios, *Shigella* species, *Salmonella, Listeria monocytogenes, Campylobacter jejuni, Yersinia enterocolitica*, Caliciviruses, Hepatitis A virus, *Cryptosporidium parvum, Cyclospora cayatanensis, Giardia lamblia, Entamoeba histolytica, Toxoplasma*, Microsporidid, Nipah virus, Tick borne hemorrhagic fever viruses, Crimean-Congo Hemorrhagic fever virus, Tick-borne encephalitis viruses, Yellow fever, Multi-drug resistant TB, Influenza, Rickettsias, Rabies, Middle East respiratory syndrome coronavirus (MERS-COV), Severe acute respiratory syndrome-associated coronavirus 1 (SARS-CoV1) or SARS-CoV2. In some embodiments, the pathogenic agent is selected from vaccinia, *Francisella tularensis*, human papilloma virus, West Nile virus, *Burkholderia pseudomallei*, *Yersinia pestis*, *Mycobacterium tuberculosis*, *Toxoplasma gondii*, or *Plasmodium falciparum*. In some embodiments, the pathogenic agent is *Francisella tularensis* or *Burkholderia pseudomallei*.

Also provided are isolated peptides comprising, or consisting essentially of, or consisting of an amino acid sequence set forth in SEQ ID NOs: 1-91. In some embodiments, the peptide comprises, or consists of an sequence set forth as SEQ ID NOs: 4-8, 16, 25, 28, 35, 37, 38, 41, or 68. In some embodiments, the peptide comprises an amino acid sequence set forth as SEQ ID NOs: 1, 11, 39, 40, or 41. In a further embodiment, the isolated peptide comprises, consists essentially of, or yet further consists of, a peptide selected from: A0A0H3HE88, A0A0H3HFM1, A0A0H3HFV2, A0A0H3HG39, A0A0H3HGE0, A0A0H3HGZ9, A0A0H3HH83, A0A0H3HIF5, A0A0H3HIT5, A0A0H3HJ13, A0A0H3HJ23, A0A0H3HJC7, A0A0H3HJJ2, A0A0H3HJK0, A0A0H3HKL0, A0A0H3HL61, A0A0H3HL96, A0A0H3HLA6, A0A0H3HP07, A0A0H3HP28, A0A0H3HP60, A0A0H3HPH9, A0A0H3HPQ2, A0A0H3HPU8, A0A0H3HPW5, A0A0H3HQ22, A0A0H3HQK7, A0A0H3HQU5, A0A0H3HQZ3, A0A0H3HRL4, A0A0H3HT35, A0A0H3HT47, A0A0H3HT48, A0A0H3HTS6, A0A0H3HTT4, A0A0H3HUR4, A0A0H3HV11, A0A0H3HVV9, A0A0H3HW74, A0A0H3HWA2, A0A0H3HWC6, A0A0H3HWL5, A0A0H3HYU5, Q5NEE1, Q5NES2, Q5NET6, Q5NEX3, Q5NF68, Q5NF69, Q5NF78, Q5NFC6, Q5NFG7, Q5NGE4, Q5NGG1, Q5NGQ3, Q5NGV7, Q5NH48, Q5NHA9, Q5NHC8, Q5NHF3, Q5NHR7, Q5NHX9, Q5NI93, Q5N198, Q5NID9, Q5NII1, Q5NIJ3, or Q5NIK5.

In some embodiments, the immunogenic composition is for use in a method of eliciting an immune response in a subject, comprising, or consisting essentially of, or yet further consisting of administering to the subject an effective amount of the composition, thereby eliciting an immune response in the subject. In some embodiments, the immune response comprises a CD4+ T cell response, a CD8+ T cell response, a humoral response, or a combination thereof. In some embodiments, the immune response is cellular immunity, humoral immunity, or a combination thereof. In some embodiments, the peptide of the immunogenic composition comprises an amino acid sequence set forth as SEQ ID NOs: 4-8, 16, 25, 28, 35, 37, 38, 41, or 68. In some embodiments, the peptide comprises an amino acid sequence set forth as SEQ ID NOs: 1, 11, 39, 40, or 41. In some embodiments, the peptide comprises an amino acid sequence set forth as SEQ ID NOs: 1-44, or 45-91. In a further aspect, a composition is provided comprising the immunogenic peptides as disclosed herein or combinations thereof, e.g., wherein the composition comprises at least five non-identical overlapping peptides from a protein selected from accession numbers A0A0H3HE88, A0A0H3HFM1, A0A0H3HFV2, A0A0H3HG39, A0A0H3HGE0, A0A0H3HGZ9, A0A0H3HH83, A0A0H3HIF5, A0A0H3HIT5, A0A0H3HJ13, A0A0H3HJ23, A0A0H3HJC7, A0A0H3HJJ2, A0A0H3HJK0, A0A0H3HKL0, A0A0H3HL61, A0A0H3HL96, A0A0H3HLA6, A0A0H3HP07, A0A03HP28, A0A03HP60, A0A0H3HPH9, A0A0H3HPQ2, A0A0H3HPU8, A0A0H3HPW5, A0A0H3HQ22, A0A0H3HQK7, A0A0H3HQU5, A0A0H3HQZ3, A0A0H3HRL4, A0A0H3HT35, A0A0H3HT47, A0A0H3HT48, A0A0H3HTS6, A0A0H3HTT4, A0A0H3HUR4, A0A0H3HV11, A0A0H3HVV9, A0A0H3HW74, A0A0H3HWA2, A0A0H3HWC6, A0A0H3HWL5, A0A0H3HYU5, Q5NEE1, Q5NES2, Q5NET6, Q5NEX3, Q5NF68, Q5NF69, Q5NF78, Q5NFC6, Q5NFG7, Q5NGE4, Q5NGG1, Q5NGQ3, Q5NGV7, Q5NH48, Q5NHA9, Q5NHC8, Q5NHF3, Q5NHR7, Q5NHX9, Q5NI93, Q5N198, Q5NID9, Q5NII1, Q5NIJ3, or Q5NIK5.

In one aspect, the present disclosure provides a computational method of analyzing a dataset comprising: (a) generating a plurality of control-experiment pairs of datasets, each pair comprising: (i) a control dataset comprising experimental peptides purified based on immunoglobulins from a first subject that is not immunized to a pathogenic agent, and (ii) a corresponding experiment dataset comprising control peptides purified based on immunoglobulins from a second subject that is immunized to the pathogenic agent; (b) applying an epitope model to the pairs of datasets to identify, based on which peptides are more abundant in each experimental dataset than in the corresponding control dataset, a set of one or more candidate epitopes; and (c) formulating a vaccine or a cellular therapy for the pathogenic agent based on the set of candidate epitopes.

Also provided is a non-transitory computer-readable storage medium comprising instructions which, when executed by a processor of a system, cause the system to: (a) generate a plurality of control-experiment pairs of datasets, each pair comprising: (i) a control dataset comprising experimental peptides purified based on immunoglobulins from a first subject that is not immunized to a pathogenic agent, and (ii) a corresponding experiment dataset comprising control peptides purified based on immunoglobulins from a second subject that is immunized to the pathogenic agent; and (b) apply an epitope model to the pairs of datasets to identify, based on which peptides are more abundant in each experimental dataset than in the corresponding control dataset, a set of one or more candidate epitopes, wherein applying the epitope model comprises generating a frequency for peptides occurring more abundantly in the experiment datasets relative to the corresponding control datasets.

In another aspect, the disclosure provides a system a processor and a non-transitory storage medium comprising instructions which, when executed by the processor, cause the system to: (a) generate a plurality of control-experiment pairs of datasets, each pair comprising: (i) a control dataset comprising experimental peptides purified based on immunoglobulins from a first subject that is not immunized to a pathogenic agent, and (ii) a corresponding experiment dataset comprising control peptides purified based on immunoglobulins from a second subject that is immunized to the pathogenic agent; and (b) apply an epitope model to the pairs of datasets to identify, based on which peptides are more abundant in each experimental dataset than in the corresponding control dataset, a set of one or more candidate epitopes, wherein applying the epitope model comprises generating a frequency for peptides occurring more abundantly in the experiment datasets relative to the corresponding control datasets.

BRIEF DESCRIPTION OF THE DRAWINGS

FIG. 2D; 2) when compared with non-immunized mice (PBS-treated mice, 1). Seroreactivity of mice sera to microwells coated with corresponding pathogen lysate was assessed using protein-A/G-HRP and measuring sample absorbance (optical density). Sera of some mice immunized with Ft did not yield positive results because Ft infection led to lethal outcome and mice had to be euthanized during the course of immunization. Graphs represent two replicates for sera collected from each mouse. Antibodies from sera with the strongest Western blot and ELISA signals were purified in this study and used to screen for immunogenic peptides.

FIG. 4A shows a western blot analysis using streptavidin-HRP illustrating the incorporation of Anl in Bt-MetRS$^{NLL}$ proteins from lysates of Bt or Bt-MetRS$^{NLL}$ that were cultured in media with or without Anl and subjected to a click reaction using biotin-alkyne. Biotinylated proteins were detected using streptavidin-HRP. Primary goat anti-*Burkholderia* antibodies and secondary donkey anti-goat antibodies conjugated to HRP were used as a loading control. FIG. 4B shows a western blot analysis illustrating the relative protein quantity in lysates from FIG. 4A, which was assessed by loading the same amounts of lysates onto SDS-PAGE gel and detecting total protein using Sypro Ruby stain.

FIG. 4C shows a western blot analysis illustrating that Anl-labeling of Bt-MetRS$^{NLL}$ during infection is bacteria-specific. Human epithelial cells (A549) were infected at MOI 100 and cultured for 18 hrs in DMEM media supplemented with or without 1 mM Anl. Lysates from infected and uninfected monolayers were subjected to click chemistry using alkyne conjugated to biotin. Biotin-tagged proteins in cell lysates were detected by Western blotting with streptavidin-HRP. As a loading control, human GAPDH was detected using primary rabbit anti-GAPDH antibodies and secondary goat anti-rabbit antibodies conjugated to HRP.

FIG. 4D shows an immunofluorescence image illustrating the in-situ fluorescent detection of host-associated bacteria. A549 cells were infected at an MOI of 100 with Bt-MetRS$^{NLL}$ bacteria and grown in media supplemented with 1 mM Anl for 6 hrs. Infected cells were fixed and stained with Alexa Fluor 594-wheat germ agglutinin (WGA) conjugate to visualize host cell membranes (red). Cells were subjected to click chemistry using Alexa Fluor 488 conjugated to alkyne to tag Anl-labeled proteins (green). Host cell nuclei were stained using 6-diamidino-2-phenylindole (DAPI). White arrow indicates bacteria. Fluorescent signal was visualized using fluorescence microscopy; 100× magnification was used for all images. Scale bars indicate the distance of 10 μm. FIGS. 4A-D were previously published as FIGS. 2 and 3 in Franco et al. (2018). FIG. 4E shows a western blot analysis illustrating the presence of biotinylated proteins in a whole cell lystates of *E. coli* cell expressing a variant tRNA methionine synthase (MetRS$^{NLL}$) grown in media with or without azidonorleucine (Anl); Anl labeling was detected by adding alkyne-biotin tag to the whole cell lysate. L indicates protein ladder.

FIG. 7 shows Table 1, which discloses a list of top scoring immunoreactive peptides identified in *Francisella tularensis*. Shade means experiment>control. Numbers (1 and 2) mean experiment<control. Dark shade and number 2 indicate >2-fold difference in relative abundance. Proteins with multiple top scoring peptides are highlighted in bold.

FIG. 8 shows Table 2, which discloses a list of top scoring immunoreactive peptides identified for *Burkholderia pseudomallei*. Shade means experimental sample>control. Numbers (1 and 2) mean experimental sample<control. Dark shade and number 2 indicate >2-fold difference in relative abundance. Proteins with multiple top scoring peptides are highlighted in bold FIGS. 9A-C show Table 3, which discloses a list of top scoring immunoreactive peptides identified for *Francisella tularensis*.

FIGS. 10A-C show Table 4, which discloses a list of top scoring immunoreactive peptides identified for *Burkholderia pseudomallei*.

DETAILED DESCRIPTION

Figure 1:
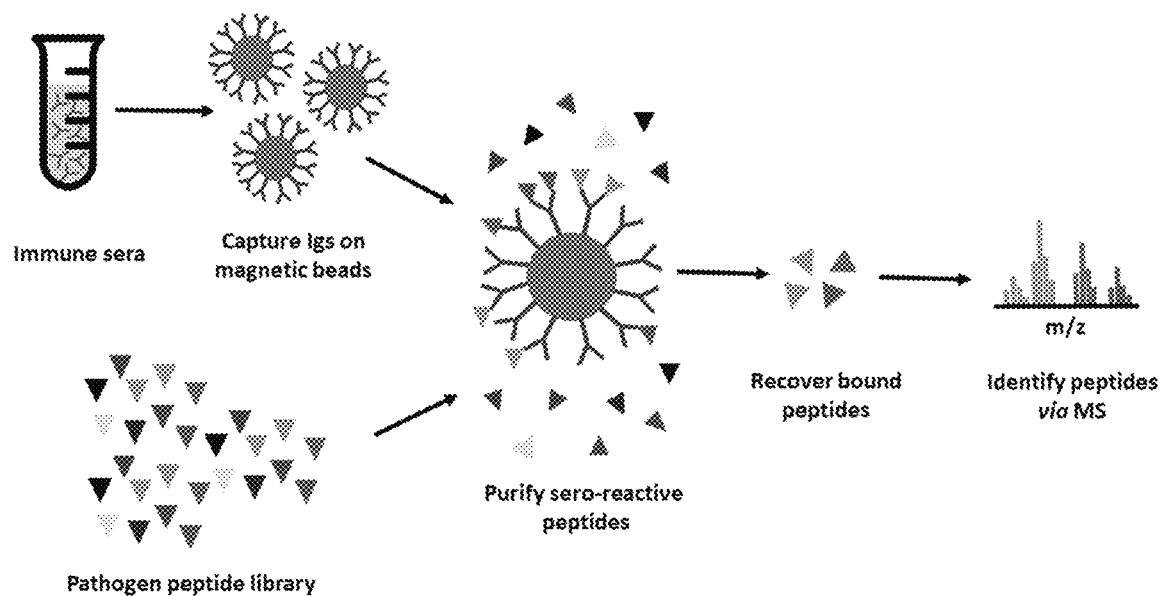
FIG. 1 shows a schematic overview illustrating the high throughput approach (immunoproteome screening workflow) for the identification of seroreactive peptides in the proteomes of pathogens.
Figure 2A:
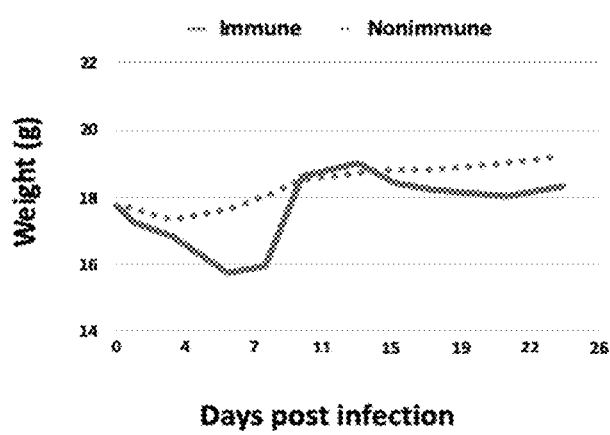
FIG. 2A shows a graph illustrating a representative course of mouse infection for obtaining immune sera. Mice were infected with a sublethal dose of *B. pseudomallei* (Bp) and their weight monitored. Weight was monitored throughout the course of infection and the degree of weight loss correlated to the amount of antibodies detected in the sera.
Figure 2B:
FIG. 2B shows a representative western blot analysis of sera from infected vs uninfected mice illustrating the absence and presence of Bp proteins in immune and non-immune sera. Bp protein lysates were analyzed by western blotting using sera from immune and nonimmune mice (Mouse 1-3) and bound antibodies detected using anti-mouse HRP. Antibodies from sera with the strongest signal were purified and used to screen for immunogenic peptides.
Figure 2C:
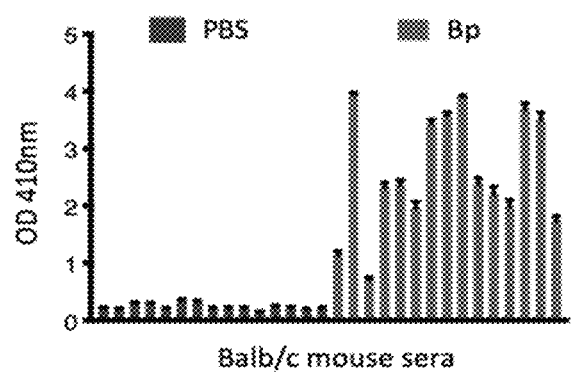
FIGS. 2C-D show bar graphs illustrating representative ELISA results obtained from mice immunized with Bp (FIG. 2C) and *Francisella tularensis* (Ft.
Figure 2D:
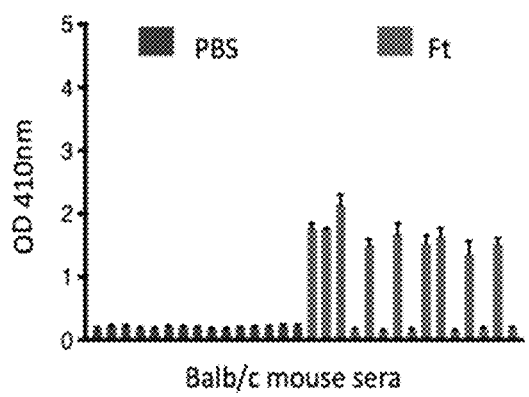

High-throughput technologies to screen for epitopes at the whole proteome level, such as proteomic arrays and phage or yeast display Methods are known in the art. However, these methods require prior knowledge of antigenicity or involve time-consuming experimentation (e.g. library construction and expression of proteins using non-native expression systems). Methods for epitope detection of currently used in the art involve studying the antigenic profiles on a single protein level, which are low throughput (one protein at a time) methods and require initial knowledge of the antigen. The approach described herein combines the reliability of in vivo experimentation with the high throughput nature of mass spectrometry and bioinformatics for identification of candidate immunogenic epitopes for development of effective and safe vaccine formulations.

One of the greatest disadvantages of non-native expression systems is that they do not reliably replicate the native conformations of proteins and their post-translational modifications. The high-throughput proteome-wide screen disclosed herein is more efficient than currently available methods for epitope discovery as it does not require prior knowledge of antigenicity and does not involve cumbersome techniques including library construction, the use of non-native expression systems, phage/yeast display technologies, peptide array preparation or other currently employed techniques. The methods of the present disclosure achieve proteome-wide screening for linear B cell epitopes using sera from immunized or convalescent mice and native proteomes isolated from a pathogenic agent of interest. This strategy holds several advantages over the currently available methods for epitope discovery. This novel strategy does not require prior knowledge of antigenicity or antigen structure, and it obviates need for complex and laborious experimental techniques such as preparation of display libraries and heterologous protein expression. Methods for epitope discovery from serum known in the art may be less well suited for pathogens for which natural infection does not confer immunity, such as HIV, Malaria and TB, although even in those cases protective antibodies may be found in some subsets of patients or animal models.

The novel approach disclosed herein was designed to enable identification of the protein antigen and, importantly, the antigenic regions within the identified antigen, such that these short linear peptides can be immediately synthesized and tested for efficacy in vaccine formulations. While several strategies have been previously developed for the identification of T-cell peptide epitopes, including techniques similar to the methods disclosed herein herein involving purification of MHC-bound peptides and their subsequent identification via LC/MS/MS, the methods disclosed herein is a great improvement over the art.

In one aspect, the present disclosure relied on the combination of bioscience experimentation and high-performance computing to provide new potential solutions to emerging disease outbreaks. As an exemplification of such approach, two intracellular bacterial pathogens, *Francisella tularensis* (Ft) and *Burkholderia pseudomallei* (Bp), novel peptides that may be used for peptide-based vaccine were identified. These two organisms represented an exemplification for this disclosure because they pose a high risk for misuse as bioweapons and therefore are considered Tier 1 Select Agents by the US Centers for Disease Control and Prevention. The mortality rates of both pathogens are high and there is currently no licensed vaccine available for either agent (Dienst 1963, Fulton et al. 2011, Gibney and Cheng 2019).

Humoral immunity plays an important role in developing immune protection to both of these intracellular pathogens making them good model organisms. In addition, the immunoproteome of Ft has been thoroughly characterized, such that previously published data could be compared to the generated datasets. A merged dataset of 164 previously identified antigens, which makes up ~10% of Ft proteome (with 1667 total proteins in Ft proteome) was leveraged. The Bp immunoproteome is not as well characterized compared to that of Ft, the referenced dataset contained only 67 previously identified seroreactive proteins (Felgner et al., 2009) in the Bp proteome of 6203 proteins (~1% of all Bp proteins were identified as antigens). Consequently, the dataset resulting from the Bp screen has revealed many proteins that have not been previously categorized as antigens.

In addition, to the best of Applicant's knowledge, the high-performance computing methods disclosed herein are novel and have not previously been used in the art. The standard analytical method used in the art required performing a T-test to find peptides that have a significantly higher average abundance in experiment vs control. However, applying this conventional method only yielded a very small number of significant peptides, likely because the response across experimental animals was highly variable. In contrast, Applicant used a novel high-performance computing analytical method to analyze high throughput data when, as presented here, a response across experimental animals is highly variable. Thus a novel and unique aspect of the present disclosure comprises the analytical process described herein, which provided highly significant and unexpected peptides for use in peptide-based vaccines.

A variety of computational B-cell epitope prediction tools to identify epitopes in antigens are known in the art. However accurate computational prediction of B-cell epitopes still poses a major challenge, with sensitivity or specificity typically below 60%, leading some recent in-silico multi-epitope vaccine design efforts to look at the consensus of up to 8 or 9 B-cell epitope prediction tools simultaneously. The recent development of prediction tools using state-of-the-art machine learning models that claim significantly higher performance on large benchmarking datasets seems promising. Applicant compared the performance of Bepipred 2.0 (35), one of the most widely used B-cell prediction tools, and iBCE-EL; and found no significant correlation between the peptides experimentally identified using the method described herein and computationally predicted linear B-cell epitope scores generated by Bepipred 2.0 and iBCE-EL, even for those antibody-binding peptides belonging to known Ft or Bp antigens, nor do they find any significant correlation between the Bepipred 2.0 and iBCE-EL scores themselves. The methods disclosed herein and the exemplified embodiments shown in Examples 1-9 below highlight the value and novelty of the unbiased experimental methods for screening for antibody targets disclosed herein.

The methods disclosed herein identified peptides that are immunoreactive, that is, they interact with antibodies in serum from previously infected individuals. These peptides stimulate antibody production themselves (i.e., immunogenic) and to protect against infection or disease after immunization (i.e., protectivity). Thus, also provided herein are provides novel immunoproteomic methods as new tools for precise mapping of linear B cell epitopes. The generation of such immunogenic profiles for pathogens using the methods disclosed herein provide an ample pool of novel candidates for efficient vaccine development. The methods disclosed herein accelerate the discovery of B cell epitopes in the proteomes of pathogens and help fuel the development of peptide-based vaccines that have the potential to provide rapid solutions to biothreat agents and other emerging pathogens.

It is to be appreciated that certain aspects, modes, embodiments, variations and features of the present methods are described below in various levels of detail in order to provide a substantial understanding of the present technology.

Definitions

Unless defined otherwise, all technical and scientific terms used herein generally have the same meaning as commonly understood by one of ordinary skill in the art to which this technology belongs. As used in this specification and the appended claims, the singular forms “a”, “an” and “the” include plural references unless the context clearly dictates otherwise. For example, reference to “a cell” includes a combination of two or more cells, and mixtures thereof. Generally, the nomenclature used herein and the laboratory procedures in cell culture, molecular genetics, organic chemistry, analytical chemistry and nucleic acid chemistry and hybridization described below are those well-known and commonly employed in the art.

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior disclosure.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term “about”. It also is to be understood, although not always explicitly stated, that the reagents described herein are merely exemplary and that equivalents of such are known in the art.

As used herein, the term “comprising” is intended to mean that the compositions and methods include the recited elements, but do not exclude others. “Consisting essentially of” when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives (e.g., sodium benzoate, potassium sorbate, and methyl hydroxybenzoate), and the like. “Consisting of” shall mean excluding more than trace elements of other ingredients and substantial method steps for administering the compositions disclosed herein. Embodiments defined by each of these transition terms are within the scope of this disclosure.

As used herein, the term “recognize or bind” intends that the binding agent, e.g., a antibody, antigen binding fragment or a Fab (fragment antigen binding) is more likely than not to bind to its intended target or binding partner.

As used herein, a “subject” of diagnosis or treatment is a cell or an animal such as a mammal, or a human. A subject is not limited to a specific species and includes non-human animals subject to diagnosis or treatment and are those subject to infections or animal models, for example, simians, murines, such as, rats, mice, chinchilla, canine, such as dogs, leporids, such as rabbits, livestock, sport animals, and pets. Human patients are included within the term as well.

The term “protein,” “peptide,” and “polypeptide” are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein’s or peptide’s sequence. As used herein the term “amino acid” refers to either natural and/or unnatural or synthetic amino acids, including glycine and both the D and L optical isomers, amino acid analogs and peptidomimetics.

The terms “polynucleotide” and “oligonucleotide” are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or a gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide or Fab (fragment antigen binding) intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity can determined by incorporating them into clustalW (available at the web address: genome.jp/tools/clustalw/, last accessed on Jan. 13, 2017).

As used herein, "homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure. In some embodiments, "homology" or "identity" or "similarity" can also refer to two nucleic acid molecules that hybridize under stringent conditions.

As used herein, "hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C. . . . ; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

As used herein, the term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," and "treatment" are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder. Methods to determine if treatment has occurred are known in the art and briefly described herein.

To prevent intends to prevent a disorder or effect in vitro or in vivo in a system or subject that is predisposed to the disorder or effect. An example of such is preventing an infection in a system that is infected with an organism known to produce one.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

The term "pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, microspheres, microparticles, or nanoparticles (comprising e.g., biodegradable polymers such as Poly (Lactic Acid-co-Glycolic Acid)), and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

A "biologically active agent" or an active agent disclosed herein intends one or more of an isolated or recombinant polypeptide, an isolated or recombinant polynucleotide, a vector, an isolated host cell, or an antibody, as well as compositions comprising one or more of same.

"Administration" or "delivery" of a therapeutic or other agent can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application. Administration can be for use in industrial as well as therapeutic applications.

As used herein, the term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, species, and tolerance to pharmaceutical compositions. In the context of this disclosure, in some embodiments the effective amount is the amount sufficient to treat or prevent an infection with the agent. In other embodiments, the effective amount of an agent or an immunogenic composition is the amount sufficient to result in antibody generation against the antigen. In some embodiments, the effective amount is the amount required to confer passive immunity on a subject in need thereof. With respect to compositions, in some embodiments the effective amount will depend on the intended use, the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

"Liposomes" are microscopic vesicles consisting of concentric lipid bilayers. A liposome is an example of a carrier, e.g., a pharmaceutically acceptable carrier. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, distearoylphosphatidylethan-olamine (DSPE), dioleoylphosphatidylcholine (DOPC), dipalmitoylphosphatidylcholine (DPPC), palmitoyloteoylphosphatidylcholine (POPC), palmitoyloleoylphosphatidylethanolamine (POPE) and dioleoylphosphatidylethanolamine 4-(N-maleimido-triethyl) cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioteoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs). The biological active agents can be encapsulated in such for administration in accordance with the methods described herein.

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody, antigen binding fragment, vaccine, or composition described herein to facilitate efficient delivery to the target cell or tissue.

As used herein, the phrase "pharmaceutically acceptable polymer" refers to the group of compounds which can be conjugated to one or more polypeptides or antibodies described here. It is contemplated that the conjugation of a polymer to the polypeptide or antibody is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

As used herein, a "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

As used herein, a "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106 (15): 6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5 (7): 823-827. In aspects where gene transfer is mediated by a retroviral vector, a vector construct refers to the polynucleotide comprising the retroviral genome or part thereof, and a therapeutic gene. Further details as to modern methods of vectors for use in gene transfer may be found in, for example, Kotterman et al. (2015) Viral Vectors for Gene Therapy: Translational and Clinical Outlook Annual Review of Biomedical Engineering 17.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. Ads do not require integration into the host cell genome. Recombinant Ad derived vectors, particularly those that reduce the potential for recombination and generation of wild-type virus, have also been constructed. Such vectors are commercially available from sources such as Takara Bio USA (Mountain View, CA), Vector Biolabs (Philadelphia, PA), and Creative Biogene (Shirley, NY). Wild-type AAV has high infectivity and specificity integrating into the host cell's genome. See, Wold and Toth (2013) Curr. Gene. Ther. 13 (6): 421-433, Hermonat & Muzyczka (1984) Proc. Natl. Acad. Sci. USA 81:6466-6470, and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the terms "antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', $F(ab)_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, species-ized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues.

The antibodies can be polyclonal, monoclonal, multispecific (e.g., bispecific antibodies), a diabody, and antibody fragments, so long as they exhibit the desired biological activity. Antibodies can be isolated from any suitable biological source, e.g., a human, a murine, rat, sheep and canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like and can be used, therapeutically, diagnostically or to isolate a polypeptide.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

As used herein, the term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, CL, CH domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin. Additional non-limiting examples of linker polypeptides are provided herein.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

As used herein, a "human monoclonal antibody" refers to antibodies displaying a single binding specificity which have variable and constant regions derived from human germline immunoglobulin sequences. The term also intends recombinant human antibodies.

As used herein, the term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalaninetyrosine, lysine-arginine, alanine-valine, serine-threonine and asparagine-glutamine. The term "species-ized" refers to antibodies that have been modified in the same or a similar manner for a non-human species.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope. In some embodiments, the antibody or antigen binding fragment is not a polyclonal antibody.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof. This disclosure also provided antibody derivatives of the antibody fragments, e.g., the polypeptides conjugaged to another molecule, e.g., PEG or further modified by acylation.

As used herein, the term "immunoconjugate" comprises an antibody, an antibody fragment or a antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody. This disclosure provides immunoconjugates comprising as one component, an antibody or Fab fragment and the second agent.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}Sn$, $^{117}Sn$ and $^{119}Sn$, a non-radioactive isotopes such as $^{13}C$ and $^{15}N$, polynucleotide or protein such as an antibody so as to generate a "labeled" composition. The term also includes sequences conjugated to a polynucleotide that will provide a signal upon expression of the inserted sequences, such as green fluorescent protein (GFP) and the like. The term also includes purification tags or labels that aid in the isolation of biological materials from mixed populations. While the term "label" generally intends compositions covalently attached to the composition to be detected, in one aspect it specifically excludes naturally occurring nucleosides and amino acids that are known to fluoresce under certain conditions (e.g., temperature, pH, etc.) when positioned within the polynucleotide or protein in its native environment and generally any natural fluorescence that may be present in the composition to be detected. The label may be detectable by itself (e.g., radioisotope labels or fluorescent labels) or, in the case of an enzymatic label, may catalyze chemical alteration of a substrate compound or composition that is detectable. The labels can be suitable for small-scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, CASCADE BLUE™, and Texas Red.

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" are cells that usually lack a nucleus or any other membrane-bound organelles and are divided into two domains, bacteria and archaca. In addition to chromosomal DNA, these cells can also contain genetic information in a circular loop called on episome. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to Bacillus bacteria, E. coli bacterium, and Salmonella bacterium.

As used herein, a "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances that are immunogenic, i.e., immunogens, as well as substances which induce immunological unresponsiveness, or anergy, i.e., anergens.

As used herein, "immune response" broadly refers to the antigen-specific responses of lymphocytes to foreign substances. The terms "immunogen" and "immunogenic" refer to molecules with the capacity to elicit an immune response. All immunogens are antigens; however, not all antigens are immunogenic. An immune response disclosed herein can be humoral (via antibody activity) or cell-mediated (via T cell activation). The response may occur in vivo, ex vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

As used herein, the term "passive immunity" refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

As used herein, the term "inducing an immune response in a subject" is a term well understood in the art and intends that an increase of at least about 2-fold, at least about 5-fold, at least about 10-fold, at least about 100-fold, at least about 500-fold, or at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., ChemPep, Inc., etc.), PolyHIPE resins, which is a copolymer based on polystyrene with grafted polydimethylacrylamide; HIPE=high internal phase emulsionpolyamide resin (obtained from Sigma-Aldrich, St. Louis, MO), polystyrene resin grafted with polyethylene glycol (TentaGel®, Rapp Polymere, Tubingen, Germany) or polydimethylacrylamide resin (obtained fromSigma-Aldrich, St. Louis, MO).

An example of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

As used herein, a "model" generally comprises an approach to generating and analyzing particular data using particular techniques to obtain a particular desired result, and may employ various supervised and unsupervised machine learning and artificial intelligence techniques, statistical analyses, etc. The data may comprise specific data in particular formats and structures, and application of the model may include implementing a specific combination of techniques and analyses to obtain, for example, a particular solution, and/or a classifier capable of receiving certain inputs and providing certain outputs, etc. The model may be multi-stage, such that first-stage input data may be generated and processed to obtain a first-stage result that in turn is used to generate second-stage input data (or the first-stage result may itself be the second-stage input data) that is analyzed to obtain a second-stage result, which may itself be a final desired result or may be subjected to further analysis or processing to obtain the final desired result. Datasets may include, for example, training datasets used to train classifiers, and other datasets that may serve as inputs to trained classifiers to obtain desired outputs.

As used herein, a "system" means one or more computing devices capable of receiving data inputs, executing computing code, and generating data outputs, and may be part of a network of co-located and/or remote computing devices capable of transmitting and receiving data via wired or wireless communication protocols. The system may include a server system that can operate in response to requests received via a network interface that can connect multiple server systems or other computing devices to each other, providing scalable systems capable of managing high volumes of activity. Techniques for managing server systems and server farms (collections of server systems that cooperate) can be used, including dynamic resource allocation and reallocation. Network interfaces can provide a connection to the network, such as a wide area network (e.g., the Internet) to which a network interface of server system 1100 is also connected. Network interfaces can include a wired interface (e.g., Ethernet) and/or a wireless interface implementing various RF data communication standards such as Wi-Fi, Bluetooth, or cellular data network standards (e.g., 3G, 4G, LTE, 5G, etc.). Server systems can interact with various user-owned or user-operated devices via a wide-area network such as the Internet. Client computing systems can be implemented, for example, as a consumer device such as a smartphone, other mobile phone, tablet computer, wearable computing device (e.g., smart watch, eyeglasses), desktop computer, laptop computer, and so on. Client computing systems can communicate via network interfaces and can include computer components such as processors, storage media, network interfaces, user input devices, and user output devices. Suitable devices can be selected based on the demands to be placed on client computing system; for example, client computing system can be implemented as a "thin" client with limited processing capability or as a high-powered computing device. Client computing system can be provisioned with program code executable by processors to enable various interactions with server system of a message management service such as accessing messages, performing actions on messages, and other interactions described herein. Some client computing systems can also interact with a messaging service independently of the message management service.

As used herein, a "processor" or "processing unit" may comprise a single processor, which can have one or more cores, or multiple processors. Processors can include one or more general-purpose primary processor as well as one or more special-purpose co-processors such as graphics processors, digital signal processors, or the like. Some or all processors may be implemented using customized circuits, such as application specific integrated circuits (ASICs) or field programmable gate arrays (FPGAs). In some embodiments, such integrated circuits execute instructions that are stored on the circuit itself. In other embodiments, processors can execute instructions stored in local or remote computing storage devices.

As used herein, a "storage medium" can include any combination of volatile storage media (e.g., dynamic random-access memory (DRAM), static random-access memory (SRAM), synchronous DRAM (SDRAM), or the like) and/or non-volatile storage media (e.g., magnetic or optical disk, flash memory, or the like). Storage media can be fixed, removable, or upgradeable as desired. Storage media can be physically or logically divided into various subunits such as a system memory, a read-only memory (ROM), and a permanent storage device. The memory of a system can be a read-and-write memory device or a volatile read-and-write memory, such as dynamic random-access memory. The system memory can store some or all of the instructions and data that a system's processors need at runtime. The ROM can store static data and instructions that are needed by the processors. The permanent storage device can be a non-volatile read-and-write memory device that can store instructions and data even when the memory device is powered down. The term "non-transitory storage medium" as used herein includes any medium in which data can be stored indefinitely (subject to overwriting, electrical disturbance, power loss, or the like) and does not include carrier waves and transitory electronic signals propagating wirelessly or over wired connections. Local storage media may be intended to provide working memory for processors, providing fast access to programs and/or data to be processed while reducing traffic on the network. Storage for larger quantities of data can be provided on the network by one or more mass storage subsystems that can be interconnected to one or more computing devices. Mass storage subsystem can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystems. In some embodiments, additional data storage resources may be accessible via the network (potentially with increased latency).

Some embodiments include electronic components, such as microprocessors, storage and memory that store computer program instructions in a computer readable storage medium. Many of the features described in this specification can be implemented as processes that are specified as a set of program instructions encoded on a computer readable storage medium. When these program instructions are executed by one or more processing units, they cause the processing units to perform various operations indicated in the program instructions. Examples of program instructions or computer code include machine code, such as is produced by a compiler, and files including higher-level code that are executed by a computer, an electronic component, or a microprocessor using an interpreter. Through suitable programming, processing units can provide various functionality for server system and client computing system, including any of the functionality described herein as being performed by a server or client, or other functionality associated with message management services.

Modes for Carrying Out the Disclosure

Methods for Identifying Peptides for Peptide-Based Vaccines

Many of today's most successful vaccines are based on administering live attenuated or inactivated organisms to raise protective immunity against a given pathogen. Unfortunately, this approach carries limitations that have confounded development of effective vaccines against numerous pathogenic organisms. The creation of protective immunity against a pathogen typically depends upon recognition of only a few antigenic epitopes constituting a small fraction of the antigenic load present within the entire organism (Li et al., 2014). Vaccines formulated with whole organisms therefore include large amounts of antigens that not only fail to contribute to protective immunity but often deter the immune system from creating protective immune memory of the organisms. Examples of the latter phenomenon have been observed in recent studies where nonprotective immunodominant epitopes expressed by the pathogen masked antigens that do stimulate protective immunity (Novotny et al., 2003; Guo et al., 2008). Another complication that arises with introducing high antigenic loads is the potential for allergenicity (Li et al., 2014). Accordingly, efforts have shifted toward peptide vaccines, which also are safer and more costeffective than attenuated and inactivated vaccines (Li et al., 2014; Sesardic, 1993; World health Organization (WHO), 2014). Peptide vaccine formulations are comprised exclusively of epitopes that stimulate immunity, and therefore get around the many disadvantages stated above. However, efficient identification of protective epitopes remains a formidable challenge (Li et al., 2014).

The present disclosure provides a newly developed generalizable screening method that enables efficient identification of B cell or T cell epitopes in the proteomes of pathogens or other pathogenic agents. The novel process of the present disclosure is easily adaptable to detecting peptide targets relevant to the immune systems of other mammalian species, including humans (depending upon the availability of convalescent sera from patients) and could aid in accelerating the discovery of B cell or T cell epitopes and development of vaccines to counter emerging biological threats.

Thus, in one aspect provided herein is a method of identifying an immunogenic peptide comprising: (a) identifying an interactive peptide by contacting a peptide library generated from a pathogenic agent with purified peptide-specific immunoglobulins under conditions to form peptide-immunoglobulin complexes between the interactive peptides and the specific immunoglobulins and identifying one or more interactive peptides bound to the peptide-targeted immunoglobulin complexes; and (b) comparing the identified interactive peptides of step (a) to peptides bound to control immunoglobulins, and selecting at least one identified peptide of step (a) that does not bind to the control immunoglobulins or is enriched in the interactive peptides of step (a) as compared to the peptide bound to control immunoglobulins, thereby identifying an immunogenic peptide. In one aspect, the interactive peptides of step (a) are obtained from one or more of convalescent sera or from sera or plasma collected from a subject who was immunized with or exposed to the pathogenic agent. In another aspect, the control immunoglobulins are obtained from sera or plasma from a subject who was not exposed to or immunized with the pathogenic agent.

In a further aspect, the immunoglobulins are obtained from sera or plasma purified by a method comprising one or more of: affinity purification involving magnetic beads, agarose beads, affinity columns, protein G, anti-IgG antibodies, or any other methods to capture immunoglobulins.

In one embodiment, the peptide library is generated by one or more of: chemical synthesis or alternative peptide expression such as cell-free expression; by digesting a protein library produced by alternative protein expression such as cell-free expression; or by digesting a protein library extracted from a lysate of the pathogenic agent by a method comprising culturing the pathogenic agent and purifying the proteins from the lysate of the cultured pathogenic agent. In one aspect, digesting the protein library comprises contacting the proteins with one or more proteases using methods known in the art and described herein. Non-limiting examples of proteases include one or more of trypsin, chymotrypsin, elastase, proteinase K, ulilysin, thermolysin, pepsin, AspN, GluC, LysC, LysN, ArgC, Sap9, or OmpT, applied sequentially or simultaneously.

In one embodiment, the peptides of the peptide library are labeled with azidonorleucine (ANL) or azidohomoalanine (AHA). In some embodiments, proteins in the pathogenic agent are labeled with azidonorleucine. Azidonorleucine is a noncanonical amino acids that can be incorporated into cellular proteins by an engineered aminoacyl-tRNA synthetase (MetRS). Wild-type MetRS cannot incorporate Azidonorleucine into cellular proteins. Metabolic labeling of proteins with the methionine surrogate azidonorleucine is exclusively targeted to specified cells by expressing one or more mutant methionyl-tRNA synthetases (MetRS). In complex cellular mixtures, such as host cell and pathogenic agent, proteins made in a pathogenic agent that expresses the mutant MetRS is tagged with affinity reagents for detection or enrichment or fluorescent dyes for imaging. Proteins made in the host cells that do not express the mutant synthetase are neither labeled nor detected. In some embodiments, the variant MetRS that preferentially incorporates the methionine (Met) surrogate azidonorleucine (Anl) into bacterial proteins is MetRS$^{NLL}$, MetRS$^{PLL}$, MetRS$^{SLL}$, MetRS$^{CLL}$, MetRS$^{PLI}$, or MetRS$^{PIL}$.

In another aspect, selecting the peptide library comprises a bioinformatics analysis to include peptides that are predicted to be B-cell epitopes, deeply evolutionary conserved, conserved across the majority of sequenced pathogenic strains, surface exposed, part of membrane proteins, or any combination thereof.

In one specific embodiment, the method is useful where the pathogenic agent is selected from a bacterium, a fungus, a DNA virus, an RNA virus, an arenavirus, a bunyavirus, an hantavirus, a flavirus, a parasitic worm, a filovirus, a protozoa, a virulent strain or an attenuated strain of the pathogenic agent. In some embodiments, the pathogenic agent is selected from: *Bacillus anthracis, Clostridium botulinum, Yersinia pestis, Variola major* and other pox viruses, *Francisella tularensis*, human papilloma virus, West Nile virus, *Burkholderia pseudomallei, Mycobacterium tuberculosis, Toxoplasma gondii*, and *Plasmodium falciparum* LCM, Junin virus, Machupo virus, Guanarito virus, Lassa Fever, Rift Valley Fever virus, Dengue, Ebola virus, Marburg virus, *Burkholderia pseudomallei, Coxiella burnetii* (Q fever), *Brucella* species (brucellosis), *Burkholderia mallei* (glanders), Ricin toxin (from *Ricinus communis*), Epsilon toxin of *Clostridium perfringens, Staphylococcus* enterotoxin B, Typhus fever, *Rickettsia prowazekii*, Diarrheagenic *E. coli*, Pathogenic Vibrios, *Shigella* species, *Salmonella, Listeria monocytogenes, Campylobacter jejuni, Yersinia enterocolitica*, Caliciviruses, Hepatitis A virus, *Cryptosporidium parvum, Cyclospora cayatanensis, Giardia lamblia, Entamoeba histolytica, Toxoplasma*, Microsporidia, Nipah virus, Tick borne hemorrhagic fever viruses, Crimean-Congo Hemorrhagic fever virus, Tick borne encephalitis viruses, Yellow fever, Multi-drug resistant TB, Influenza, Rickettsias, Rabies, Middle East respiratory syndrome coronavirus (MERS-COV), Severe acute respiratory syndrome-associated coronavirus 1 (SARS-CoV1) or SARS-CoV2. In one aspect, the pathogenic agent is selected from vaccinia, *Francisella tularensis*, human papilloma virus, West Nile virus. *Burkholderia pseudomallei, Yersinia pestis, Mycobacterium tuberculosis. Toxoplasma gondii*, and *Plasmodium falciparum*. In a further aspect, the pathogenic agent is *Francisella tularensis* or *Burkholderia pseudomallei*. In a further aspect, the pathogenic agent comprises a pathogenic bacterium. In a yet further aspect, the pathogenic agent is genetically engineered to express a modified tRNA methionine synthase (metRS).

As used herein, the term "interactive peptide" means a peptide from a peptide library that is generated from a pathogenic agent and that interacts or binds to one or more immunoglobulins purified from sera from one or more of convalescent subject or a subject who was immunized with a pathogenic agent. In some embodiments, the peptide library is generated by culturing a pathogenic agent and producing a lysate. The proteins of the pathogenic agent are extracted using method known to one skilled in the art. In particular, the proteins from the pathogenic agent lysate are precipitated and digested using the methods disclosed in the Examples herein. Digested proteins are then filtered and stored. In some embodiments, the filtered digested protein is a peptide library of the present disclosure.

As used herein the term "immunogenic peptide" means a short fragment of a protein that is capable of eliciting an immune response. An immune response is a response of a cell of the immune system, such as a B cell, T cell, monocyte, macrophage, dendritic cell or natural killer cell to a stimulus. In one embodiment, the response is an adaptive immune response, which means a specific response to a particular antigen (i.e. "antigen-specific response"). In some embodiments, the adaptive immune response is a T cell response, such as a CD4+ response and/or a CD8+ response. In some embodiments, the adaptive immune response is a B cell response, and results in the production of specific antibodies. In some embodiments, an immunogenic peptide is a peptide that comprises an allele-specific motif or other sequence, that allows the peptide to bind to a major major histocompatibility complexes (MHC) to induce a cytotoxic T lymphocyte (CTL) response, or a B cell response (e.g. antibody production) against the protein from which the immunogenic peptide is derived. In some embodiments, immunogenic peptide means a peptide epitope, a CD8+ T cell epitope, HLA class I and class II peptide epitopes, CD4+ T cell epitope, B cell epitopes, or a combination thereof.

In one aspect, of the disclosure, the peptide library is generated from lysate of the pathogen and the library is produced by a method comprising culturing the pathogen to a concentration of at least about $10^6$-$10^{10}$ CFU/ml and ranges there between, and purifying the peptides from the lysate of the cultured pathogenic bacteria or by a method comprising generating a proteome, optionally by alternative protein expression such as cell-free expression. Cell-free protein synthesis system is an in vitro protein synthesis is a key tool that can work without the use of living cells. (Khambhati et al., 2019). In a cell-free, components from crude cellular lysates of eukaryotes (e.g., vertebrates, plants, insects, fungi), or prokaryotes (e.g., *Escherichia coli, Vibrio natriegens, Bacillus subtilis*) are used for sourcing energy and protein synthesis. Commonly used crude extracts are either of *E. coli*, rabbit reticulocytes, wheat germ (WGE), or insect cells. In a cell-free system, the cells of interest are grown overnight, diluted, and grown further until a desired optical density is reached (i.e. 0.8 to 1.0) after which cells are harvested and sonicated to extract the cell lysate. The cell lysate is them mixed with a buffer mixture comprising all the necessary cofactors, energy sources, nucleotides, substrates, amino acids, and tRNAs. The resulting mixture is called a cell-free system contemplated by the present invention. In some embodiments, the cell-free system is prepared from purified components or semi-processed cellular extracts. In some embodiments, the cell free system is made sterile via simple filtration.

In a further aspect, the lysate comprises at least about 20%, at least about 30%, at least about 40%, at least about 50%, at least about 60%, at least about 70%, at least about 80%, at least about 90%, at least about 95%, at least about 98%, at least about 99%, at least about 100% of the pathogenic agent proteome.

In an alternative aspect of this disclosure, the contacting step (a) comprises a method of contacting host cells transfected with the pathogenic agent and cultured in a media supplied with an azide-bearing methionine analog that labels pathogenic agent peptides, with the peptide library of step (a). In one aspect, the azide-bearing methionine analog is azidoporleucine (ANL) or azidohomoalanine (AHA). In a further aspect, the method comprises assaying the peptide for a broad spectrum immunity against all variants of the same pathogenic agent.

In one embodiment of the method, peptides can be selected by: (a) generating a plurality of control and identified pairs of datasets, each pair comprising (i) an identified dataset comprising the identified peptides, and (ii) a corresponding control dataset comprising control peptides purified based on immunoglobulins; and (b) identifying the peptides that are more abundant in each identified dataset as compared to the corresponding control dataset. In one embodiment of this method, the method further comprises identifying a set of one or more candidate epitopes. For example, the immunogenic peptide is identified by a method comprising liquid chromatography and/or mass spectrometry, liquid chromatography-mass spectrometry, or liquid chromatography with tandem mass spectrometry. In another aspect, the method further comprises applying Total Ion Current analysis to mass spectrometry data. In one embodiment of the method, identifying or selecting the peptides that are more abundant comprises generating a frequency for peptides occurring more abundantly in the identified dataset relative to the corresponding control dataset.

In one embodiment of the method, the method further comprises generating a matrix that scores each peptide based on whether identified peptide level was greater than, equal to, or lower than control peptide level in each pair.

In one embodiment of the method, the selecting at least one peptide does not include determining an average log fold change in abundance. In another aspect, the selecting at least one peptide does not employ a t-test to identify peptides with a significantly higher average abundance in experimental datasets as compared to control datasets.

In another aspect of this method, the method further comprises generating a plurality of input datasets corresponding to the plurality of control and identified pairs of datasets, each input dataset comprising the peptides in the peptide library. In another aspect of the method, the method further comprises the normalizing input datasets against each other based on median ratios for peptides occurring in every input dataset. In one embodiment of the method, the method further comprises normalizing the identified and control datasets against their respective input datasets based on the median ratios. In one embodiment of the method, the method further comprises performing evolutionary conservation analysis on the identified and control peptides to identify candidate epitopes. In one aspect, the evolutionary conservation analysis includes generating an average amino acid conservation score.

Immunogenic Peptides, Polynucleotides, and Cells

This disclosure also provides immunogenic peptides identified or selected by these methods. Monomeric peptide are often poorly immunogenic when compared to the entire protein. To improve immunogenicity, a peptide is linked to a virus-like particle (VLP) or nanoparticle to allow ordered, multivalent epitope presentation that can more efficiently cross-link BCRs. Accordingly, in some embodiments, the immungogenic peptides can be detectably labeled or conjugated to a dendritic cell binding protein or other antigen presenting cell peptide. In some embodiments, the immunogenic peptide is conjugated to a VLP or nanoparticle. In some embodiments, the immunogenic peptide is conjugated to bacterial toxins, anthrax toxin, or *Staphylococcus aureus* enterotoxin B, a tetanus toxoid, a diphtheria toxoid, a polysaccharide, a lipoprotein, or any combination thereof. In some embodiments, the bacterial toxin is a fragment or inactive variants. In some embodiments, the immunogenic peptide is conjugated to a dendritic cell (DC) binding peptide or an antigen presenting cell (APC)-binding peptide. In some embodiments, the immunogenic peptide is conjugated to a virus-like particle, nanoparticle, a tetanus toxoid, a diphtheria toxoid, a polysaccharide, a lipoprotein, a dendritic cell (DC) binding peptide, an antigen presenting cell (APC)-binding peptide, or any combination thereof. In some embodiments, the immunogenic peptide is encapsulated in nanoparticles. In some embodiments, the immunogenic peptide is linked to charged polymers to enhance the encapsulation of the antigens and surface decoration of the particles with RGD peptide or lectins. In some embodiments, the immunopeptide is delivered to a dendritic cell by linking to a natural polymer (i.e. chitosan). Chitosan is a naturally occurring ideal polymer because of its nontoxic nature, biocompatibility and biodegradability. In some embodiments, the immunogenic peptide is linked to carbon nanotubes, silicon dioxide nanoparticles, dendrimers, ferritin nanoparticles, peptide nanocarriers, gold nanoparticles, liposome-polycation-DNA (LPD) complex, oligosaccharide ester derivatives (OEDs) microparticles and combination systems, e.g., liposomes and w/o emulsion.

As used herein, dendritic cells are the principle professional antigen presenting cells involved in primary immune responses. Dendritic cells are potent activators of T helper cell responses because as part of their composition, they express co-stimulatory molecules on their cell surface. The major function of dendritic cells is to obtain antigen in tissues, migrate to lymphoid organs and present the antigen in order to activate T cells. Immature dendritic cells originate in the bone marrow and reside in the periphery as immature cells. Dendritic cell sub-types include plasmacytoid dendritic cells and myeloid dendritic cells. In some embodiments, immunogenic peptides are loaded onto antigen presenting cells (APC), such as dendritic cells.

In some embodiments, the immunogenic peptide(s) can be delivered to the dendritic cells or to dendritic cell precursors via any method known in the art, including, but not limited to, pulsing dendritic cells directly with the peptide, or utilizing a broad variety of peptide delivery vehicles, such as, for example, liposomes, or other vectors known to deliver antigen to cells. In some embodiments, APCs loaded immunogenic peptides can be generated by pulsing or co-incubating APCs with the immunogenic peptides. In some embodiments, APCs can be transduced with a vector encoding the immunogenic peptides. The immunogenic peptide will then be expressed and processed by the APC for presentation on the APC surface. In some embodiments, the APCs loaded with the immunogenic peptide will process and display the peptide in complex with MCH.

In some embodiments, the immunogenic peptide is a peptide mimetope that is selected by phage display using the peptide library generated herein. The mimetope can be a structural epitope whose binding to an antibody is conformation-dependent. In some embodiments, the peptides disclosed herein are rigidified to peptide epitope conformations so that they most closely match the epitope structure when bound to the antibody.

In one embodiment of the one or more peptides identified by the methods disclosed herein generate a broad spectrum immunity against all variants of the same pathogenic agent. Non-limiting examples of the peptides of this disclosure include peptides that comprise, or consist essentially of, or yet further consist of, an amino acid sequence set forth in SEQ ID NOS: 1-91.

In one aspect, the peptide comprises an amino acid sequence having at least one modification, but no more than five modifications in the amino acid sequence. In another aspect, the peptide comprises an amino acid sequence having at least 80%, at least 90%, at least 95%, or at least 98% identity to the amino acid sequence of SEQ ID NOs: 1-91.

Epitope enhancement is a modification of the amino acid sequence of epitope to improve the efficacy of vaccines. Epitope enhancement is improves immunogenicity and stability by: (1) increasing affinity of peptide for MHC molecules; (2) increasing T cell receptor (TCR) triggering; or (3) inhibiting proteolysis of the peptide by serum peptidases. Moreover, peptide epitopes that are enhanced can bypass self-tolerance because peptides do not generally induce tolerance but they can be made more immunogenic by epitope enhancement.

Accordingly, in an alternate aspect, provided herein is a fusion protein comprising a first peptide comprising or consisting essentially of an amino acid sequence selected from SEQ ID NOs: 1-91, or an amino acid sequence having at least 80%, at least 90%, at least 95%, or at least 98% identity to the amino acid sequence of SEQ ID NOs: 1-91, and optionally a second peptide comprising a T-cell stimulating epitope selected from the pathogenic agent, a tetanus toxoid, a diphtheria toxoid, a polysaccharide, a lipoprotein, or any combination thereof; a dendritic cell (DC) binding peptide or an antigen presenting cell (APC)-binding peptide. In one aspect, the peptides of the fusion peptide are separated by linker sequences with an extended conformation, or flexible linker sequences such as those with a high content of glycine residues. Also provided herein are polynucleotides encoding the peptides, including the fusion peptides as described herein, and equivalents thereof.

Further provided herein are isolated polynucleotides encoding the antibodies or antigen binding fragments thereof, or the CDRs of the antigen binding fragments or antibodies, as well as the polypeptides of this disclosure, or an equivalent of each thereof, that are optionally operatively linked to a promoter and/or enhancer element. The polynucleotides can be detectably labeled and/or comprise a detectable label and/or a purification marker. The polynucleotides can further comprise a signal peptide polynucleotide sequence located upstream of the immunoglobulin variable domain of the antibody. They can be contained within a vector and/or a host cell. Thus, further provided is a vector comprising, or alternatively consisting essentially of, or yet further consisting of one or more of the isolated polynucleotides as disclosed herein. Such vector may be a plasmid or a viral vector, optionally selected from a group consisting of a retroviral vector, a lentiviral vector, an adenoviral vector, and an adeno-associated viral vector. Also provided is a host cell comprising one or more of the polynucleotides and/or the vectors as disclosed herein.

In one embodiment of the method the amino acid sequence comprises at least two, at least three, at least four immunogenic peptides derived from a pathogenic agent. In one aspect, the amino acid sequence comprises at least five non-overlapping peptides derived from the same protein. In a further aspect, the peptide or composition comprises at least five non-identical overlapping peptides from a protein selected from the group of accession numbers A0A0H3HE88, A0A0H3HFM1, A0A0H3HFV2, A0A0H3HG39, A0A0H3HGE0, A0A0H3HGZ9, A0A0H3HH83, A0A0H3HIF5, A0A0H3HIT5, A0A0H3HJ13, A0A0H3HJ23, A0A0H3HJC7, A0A0H3HJJ2, A0A0H3HJK0, A0A0H3HKL0, A0A0H3HL61, A0A0H3HL96, A0A0H3HLA6, A0A0H3HP07, A0A0H3HP28, A0A0H3HP60, A0A0H3HPH9, A0A0H3HPQ2, A0A0H3HPU5, A0A0H3HPW5, A0A0H3HQ22, A0A0H3HQK7, A0A0H3HQU5, A0A0H3HQZ3, A0A0H3HRL4, A0A0H3HT35, A0A0H3HT47, A0A0H3HT48, A0A0H3HTS6, A0A0H3HTT4, A0A0H3HUR4, A0A0H3HV11, A0A0H3HVV9, A0A0H3HW74, A0A0H3HWA2, A0A0H3HWC6, A0A0H3HWL5, A0A0H3HYU5, Q5NEE1, Q5NES2, Q5NET6, Q5NEX3, Q5NF68, Q5NF69, Q5NF78, Q5NFC6, Q5NFG7, Q5NGE4, Q5NGG1, Q5NGQ3, Q5NGV7, Q5NH48, Q5NHA9, Q5NHC8, Q5NHF3, Q5NHR7, Q5NHX9, Q5NI93, Q5NI98, Q5NID9, Q5NIII, Q5NIJ3, or Q5NIK5.

Also provided herein, is a composition comprising a peptide, a fusion peptide or combination of peptides as described herein and one or more of a pharmaceutically acceptable carrier, an adjuvant, a preservative or a stabilizer. In some embodiments, the compositions comprise APCs loaded with the one or more immunogenic peptides. In some embodiments, the APC is a dendritic cell. In some embodiments, the APCs are autologous cells or allegeneic cells. In some embodiments, the APC is loaded using methods known in the art as described herein.

In some embodiments, a therapeutically effective amount of the APCs loaded with immunogenic peptide is administered to a subject. In some embodiments, the therapeutically effective amount of the APC composition comprises about at least about $1\times10^6$ to about $30\times10^6$ viable APCs, such as about $5\times10^6$ to about $25\times10^6$ viable APCs, or about $10\times10^6$ to about $20\times10^6$ viable APCs. In non-limiting examples, the therapeutically effective amount of the composition comprises about $1\times10^6$, $2\times10^6$, $3\times10^6$, $4\times10^6$, $5\times10^6$, $6\times10^6$, $7\times10^6$, $8\times10^6$, $9\times10^6$, $10\times10^6$, $15\times10^6$, $20\times10^6$, $25\times10^6$, or $30\times10^6$ viable APCs.

In some embodiments, multiple immunogenic peptides are administered to a subject using APCs. In those cases individual pools of cells are each pulsed with one peptide and subsequently pooled together for administration. The pooled APCs is then administered in a single injection, or in multiple injections, such as in two injections. In some embodiments, the peptide-loaded APCs are administered intradermally, but can be administered using any suitable route for generating an immune response, such as subcutaneously, intravenously or intramuscularly.

Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

This disclosure also provides isolated or recombinant polypeptides comprising or alternatively consisting essentially of, or yet further consisting of, two or more, or three or more, four or more, five or more, six or more, seven or more, eight or more, nine or more, ten or more, eleven or more, twelve or more, thirteen or more of all fourteen of the isolated polypeptides or a fragment or an equivalent of each thereof.

In any of the above embodiments, a peptide linker can be added to the N-terminus or C-terminus of the polypeptide. A "linker" or "peptide linker" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. An example of a peptide linker is Gly-Pro-Ser-Leu-Lys-Leu (SEQ ID NO: 92). Other examples include Gly-Gly-Gly; Gly-Pro-Ser-Leu (SEQ ID NO: 93); Gly-Pro-Ser; Pro-Ser-Leu-Lys (SEQ ID NO: 94); Gly-Pro-Ser-Leu-Lys (SEQ ID NO: 95); and Ser-Leu-Lys-Leu (SEQ ID NO: 96). The isolated polypeptides disclosed herein are intended to include recombinantly produced polypeptides and proteins from prokaryotic and eukaryotic host cells, as well as muteins, analogs and fragments thereof, examples of such cells are described above. It is understood that functional equivalents or variants of the wild type polypeptide or protein also are within the scope of this disclosure, for example, those having conservative amino acid substitutions of the amino acids.

In a further aspect, the polypeptides are conjugated or linked to a detectable label or an agent to increase the half-life of the polypeptide, e.g., PEGylation a PEG mimetic, polysialyation, HESylation or glycosylation. Suitable labels are known in the art and described herein.

In a yet further aspect, the polypeptides with or without a detectable label can be contained or expressed on the surface of a host prokaryotic or eukaryotic host cell, such as a dendritic cell or antigen presenting cell. Further provided are the cells expressing the peptides.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this disclosure also provides a process for chemically synthesizing the proteins disclosed herein by providing the sequence of the protein and reagents, such as amino acids and enzymes and linking together the amino acids in the proper orientation and linear sequence. Alternatively, the proteins and polypeptides can be obtained by well-known recombinant methods as described, for example, in Sambrook et al. (1989) supra, using a host cell and vector systems described herein.

Also provided by this application are the polypeptides described herein conjugated to a detectable agent for use in the diagnostic methods. For example, detectably labeled polypeptides can be bound to a column and used for the detection and purification of antibodies. They also are useful as immunogens for the production of antibodies. The polypeptides disclosed herein are useful in an in vitro assay system to screen for agents or drugs, which modulate cellular processes.

It is well known to those skilled in the art that modifications can be made to the peptides disclosed herein to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides disclosed herein can be modified to include unnatural amino acids. Thus, the peptides may comprise D-amino acids, a combination of and L-amino acids, and various "designer" amino acids (e.g., beta-methyl amino acids, C-alpha-methyl amino acids, and N-alpha-methyl amino acids, etc.) to convey special properties to peptides. Additionally, by assigning specific amino acids at specific coupling steps, peptides with alpha-helices, beta turns, beta sheets, gamma-turns, and cyclic peptides can be generated. Generally, it is believed that alpha-helical secondary structure or random secondary structure may be of particular use.

The polypeptides disclosed herein also can be combined with various solid phase carriers, such as an implant, a stent, a paste, a gel, a dental implant, or a medical implant or liquid phase carriers, such as beads, sterile or aqueous solutions, pharmaceutically acceptable carriers, pharmaceutically acceptable polymers, liposomes, micelles, suspensions and emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of E. coli, mutant derivatives of cholera toxin, CPG oligonucleotides, and adjuvants derived from squalene.

This disclosure also provides a pharmaceutical composition comprising or alternatively consisting essentially of, or yet further consisting of, any of a polypeptide, polypeptide analog, mutein, or fragment disclosed herein, alone or in combination with each other or other agents, such an antibiotic and an acceptable carrier or solid support. These compositions are useful for various diagnostic and therapeutic methods as described herein.

The disclosure further provides the isolated or recombinant polynucleotide encoding the peptides as well as the complements of the polynucleotides. In one aspect, the polynucleotides are operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides disclosed herein encode polypeptides or proteins having diagnostic and therapeutic utilities as described herein as well as probes to identify transcripts of the protein that may or may not be present. These nucleic acid fragments can by prepared, for example, by restriction enzyme digestion of larger polynucleotides and then labeled with a detectable marker. Alternatively, random fragments can be generated using nick translation of the molecule. For methodology for the preparation and labeling of such fragments, see, Sambrook et al. (1989) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using known methods. See, Sambrook et al. (1989) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Sambrook et al. (1989) supra, for methodology. Thus, this disclosure also provides a host cell, e.g., a mammalian cell, an animal cell (rat or mouse), a human cell, or a prokaryotic cell such as a bacterial cell, containing a polynucleotide encoding a protein or polypeptide.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

When the vectors are used in an method as disclosed herein as gene therapy in vivo or ex vivo, a pharmaceutically acceptable vector, such as a replication-incompetent retroviral or adenoviral vector, are exemplary (but non-limiting) and may be of particular use. Pharmaceutically acceptable vectors containing the nucleic acids disclosed herein can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) BioTechniques 7:980-990). The methodology of using replication-incompetent retroviruses for retroviral-mediated gene transfer of gene markers has been established. See e.g., Bordignon (1989) PNAS USA 86:8912-8952; Culver (1991) PNAS USA 88:3155; and Rill (1991) Blood 79 (10): 2694-2700).

This disclosure also provides genetically modified cells that contain and/or express the polynucleotides disclosed herein. The genetically modified cells can be produced by insertion of upstream regulatory sequences such as promoters or gene activators (see, U.S. Pat. No. 5,733,761). In one embodiment, the modified cells are eukaryotic cells or prokaryotic cells.

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide disclosed herein under conditions permitting hybridization (optionally moderately stringent hybridization conditions) of complementary single-stranded polynucleotides, or optionally, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Sambrook et al. (1989) supra.

The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

The polynucleotides disclosed herein can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (199.4)) or MacPherson et al. (1991) and (1995) supra, and references cited therein. Alternatively, one of skill in the art can use the sequences provided herein and a commercial DNA synthesizer to replicate the DNA. Accordingly, this disclosure also provides a process for obtaining the polynucleotides disclosed herein by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the poly-nucleotide into a suitable replication vector and insert the vector into a suitable host cell (prokaryotic or eukaryotic) for replication and amplification. The DNA so amplified can be isolated from the cell by methods known to those of skill in the art. A process for obtaining polynucleotides by this method is further provided herein as well as the polynucleotides so obtained.

RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Sambrook et al. (1989) supra. For instance, mRNA can be isolated using various lytic enzymes or chemical solutions according to the procedures set forth in Sambrook et al. (1989) supra, or extracted by nucleic-acid-binding resins following the accompanying instructions provided by manufactures.

Polynucleotides exhibiting sequence complementarity or homology to a polynucleotide disclosed herein are useful as hybridization probes or as an equivalent of the specific polynucleotides identified herein. Since the full coding sequence of the transcript is known, any portion of this sequence or homologous sequences can be used in the methods disclosed herein.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. In some embodiments, a probe useful for detecting the aforementioned mRNA is at least about 80% identical to the homologous region. In some embodiments, the probe is 85% identical to the corresponding gene sequence after alignment of the homologous region; in some embodiments, it exhibits 90% identity.

These probes can be used in radioassays (e.g., Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide disclosed herein. Accordingly, this disclosure also provides a probe comprising or corresponding to a polynucleotide disclosed herein, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least about 5 to about 10; at least about 10 to about 20; at least about 20 to about 50; at least about 50 to about 100 nucleotides, or even full length according to the complementary sequences one wishes to detect.

Nucleotide probes having complementary sequences over stretches greater than 5 to 10 nucleotides in length are generally well suited, so as to increase stability and selectivity of the hybrid, and thereby improving the specificity of particular hybrid molecules obtained. In certain embodiments, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of *E. coli* DNA polymerase, and reverse transcriptase. For illustration purposes only, a primer is the same length as that identified for probes.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively, expression of the encoded polypeptide can be detected by various methods. In particular, it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

Immunogenic Compositions

Another aspect of the present disclosure provides compositions comprising the immunogenic peptides disclosed herein. In some aspect the present disclosure provides an an immunogenic composition comprising or consisting essentially of a peptide comprising, consisting essentially of, or consisting of an amino acid sequence of set forth in SEQ ID NO: 1-91. In some embodiments, the immunogenic composition comprising a fusion protein comprising, consisting essentially of, or consisting of an amino acid sequence set for in SEQ ID NO: 1-91. In some embodiments, the immunogenic composition comprises, consists essentially of, or consists of a peptide or peptide fusion comprising, consisting essentially of, or consisting of an amino acid sequence having at least 80%, at least 90%, at least 95%, or at least 98%, at least 99% identity to an amino acid sequence set for in SEQ ID NO: 1-91. In some embodiments, the immunogenic composition a broad spectrum immunity against all variants of the same pathogenic agent. In some embodiments, the immunogenic composition provides an immunogenicity against and/or prevents infectivity against a pathogenic agent.

In some embodiments, the immunogenic composition comprises, consists essentially of, or consists of a fusion protein comprising a first peptide comprising or consisting essentially of an amino acid sequence selected from SEQ ID NOs: 1-91, or an amino acid sequence having at least 80%, at least 90%, at least 95%, or at least 98% identity to the amino acid sequence of SEQ ID NOs: 1-91, and optionally a second peptide comprising a T-cell stimulating epitope selected from the pathogenic agent, a tetanus toxoid, a diphtheria toxoid, a polysaccharide, a lipoprotein, or any combination thereof; a dendritic cell (DC) binding peptide or an antigen presenting cell (APC)-binding peptide.

In some embodiments, the immunogenic composition comprises, consists essentially of, or consists of a fusion protein comprising a first peptide comprising or consisting essentially of an amino acid sequence selected from SEQ ID NOs: 1-91, or an amino acid sequence having at least 80%, at least 90%, at least 95%, or at least 98% identity to the amino acid sequence of SEQ ID NOs: 1-91, and a second peptide comprising a T-cell stimulating epitope selected from the pathogenic agent, a tetanus toxoid, a diphtheria toxoid, a polysaccharide, a lipoprotein, or any combination thereof; a dendritic cell (DC) binding peptide or an antigen presenting cell (APC)-binding peptide. In some embodiments, the immunogenic composition comprises a fusion protein having an amino acid sequence comprising at least two, at least three, or at least four immunogenic peptides derived from a pathogenic agent. In some embodiments, the amino acid sequence comprises at least five non-overlapping peptides derived from the same protein. In some embodiments, the immunogenic composition comprises one or more peptides that are separated by linker sequences with an extended conformation, or flexible linker sequences such as those with a high content of glycine residues.

In some embodiments, the immunogenic composition comprises, consists essentially of, or consists of, at least five non-identical overlapping peptides from a protein selected from accession number A0A0H3HE88, A0A0H3HFM1, A0A0H3HFV2, A0A0H3HG39, A0A0H3HGE0, A0A0H3HGZ9, A0A0H3HH83, A0A0H3HIF5, A0A0H3HIT5, A0A0H3HJ13, A0A0H3HJ23, A0A0H3HJC7, A0A0H3HJ2, A0A0H3HJK0, A0A0H3HKL0, A0A0H3HL61, A0A0H3HL96, A0A0H3HLA6, A0A0H3HP07, A0A0H3HP28, A0A0H3HP60, A0A0H3HPH9, A0A0H3HPQ2, A0A0H3HPU8, A0A0H3HPW5, A0A0H3HQ22, A0A0H3HQK7, A0A0H3HQU5, A0A0H3HQZ3, A0A0H3HRL4, A0A0H3HT35, A0A0H3HT47, A0A0H3HT48, A0A0H3HTS6, A0A0H3HTT4, A0A0H3HUR4, A0A0H3HV11, A0A0H3HVV9, A0A0H3HW74, A0A0H3HWA2, A0A0H3HWC6, A0A0H3HWL5, A0A0H3HYU5, Q5NEE1, Q5NES2, Q5NET6, Q5NEX3, Q5NF68, Q5NF69, Q5NF78, Q5NFC6, Q5NFG7, Q5NGE4, Q5NGG1, Q5NGQ3, Q5NGV7, Q5NH48, Q5NHA9, Q5NHC8, Q5NHF3, Q5NHR7, Q5NHX9, Q5NI93, Q5NI98, Q5NID9, Q5NIII, Q5NIJ3, or Q5NIK5. In some embodiments, the immunogenic composition further comprises one or more of a pharmaceutically acceptable carrier, a preservative or a stabilizer. In one embodiment, the immunogenic composition further comprises an adjuvant.

One aspect of the present disclosure provides a an immunogenic composition as described herein for use in a method of eliciting an immune response in a subject, the method comprising administering to the subject a therapeutically effective amount of the composition, thereby eliciting an immune response in the subject. In some embodiments, the immunogenic composition elicits an immune response comprising, consisting essentially of, or consisting of a humoral response, and optionally a CD4+ T cell response, a CD8+ T cell response, or both.

The compositions comprise a carrier and one or more of an isolated polypeptide disclosed herein, a fustion peptide as disclosed herein, an isolated polynucleotide disclosed herein, a vector disclosed herein, an isolated host cell disclosed herein. The carriers can be one or more of a solid support or a pharmaceutically acceptable carrier. The compositions can further comprise an adjuvant or other components suitable for administrations as vaccines. In one aspect, the compositions are formulated with one or more pharmaceutically acceptable excipients, diluents, carriers and/or adjuvants. In addition, embodiments of the compositions of the present disclosure include one or more of an isolated polypeptide disclosed herein, an isolated polynucleotide disclosed herein, a vector disclosed herein, an isolated host cell disclosed herein, formulated with one or more pharmaceutically acceptable substances.

For oral preparations, any one or more of an isolated or recombinant polypeptide as described herein, an isolated or recombinant polynucleotide as described herein, a vector as described herein, an isolated host cell as described herein, can be used alone or in pharmaceutical formulations disclosed herein comprising, or consisting essentially of, the compound in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical formulations and unit dose forms suitable for oral administration are particularly useful in the treatment of chronic conditions, infections, and therapies in which the patient self-administers the drug. In one aspect, the formulation is specific for pediatric administration.

The disclosure provides pharmaceutical formulations in which the one or more of an isolated polypeptide disclosed herein, an isolated polynucleotide disclosed herein, a vector disclosed herein, an isolated host cell disclosed herein, can be formulated into preparations for injection in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents. A non-limiting example of such is a antimicrobial agent such as other vaccine components such as surface antigens, e.g., an OMP P5, OMP 26, OMP P2, or Type IV Pilin protein (see Jurcisek and Bakaletz (2007) J. of Bacteriology 189 (10): 3868-3875 and Murphy, T F, Bakaletz, L O and Smeesters, P R (2009) The Pediatric Infectious Disease Journal, 28: S121-S126) and antibacterial agents. For intravenous administration, suitable carriers include physiological bacteriostatic water, Cremophor EL™ (BASF, Parsippany, N.J.), or phosphate buffered saline (PBS). In all cases, a composition for parenteral administration must be sterile and should be fluid to the extent that easy syringability exists.

Aerosol formulations provided by the disclosure can be administered via inhalation and can be propellant or non-propellant based. For example, embodiments of the pharmaceutical formulations disclosed herein comprise a compound disclosed herein formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer. A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself, e.g., by an elastic bladder).

Suppositories disclosed herein can be prepared by mixing a compound disclosed herein with any of a variety of bases such as emulsifying bases or water-soluble bases. Embodiments of this pharmaceutical formulation of a compound disclosed herein can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds disclosed herein. Similarly, unit dosage forms for injection or intravenous administration may comprise a compound disclosed herein in a composition as a solution in sterile water, normal saline or another pharmaceutically acceptable carrier.

Embodiments of the pharmaceutical formulations disclosed herein include those in which one or more of an isolated polypeptide disclosed herein, an isolated polynucleotide disclosed herein, a vector disclosed herein, an isolated host cell disclosed herein, as disclosed herein is formulated in an injectable composition. Injectable pharmaceutical formulations disclosed herein are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations disclosed herein.

In an embodiment, one or more of an isolated polypeptide disclosed herein, an isolated polynucleotide disclosed herein, a vector disclosed herein, or an isolated host cell disclosed herein, is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a compound disclosed herein can be accomplished using any of a variety of refillable, pump systems. Pumps provide consistent, controlled release over time. In some embodiments, a compound disclosed herein is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation, polymers such as for example poly (glycolide-co-lactide) (PGLA) that is commercially available from a number of vendors, e.g., BioDegmer and Sigma-Aldrich. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer (e.g., PGLA) and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852; and the like. In general, a subject treatment method can be accomplished using any of a variety of refillable, non-exchangeable pump systems. Pumps and other convective systems may be utilized due to their generally more consistent, controlled release over time. Osmotic pumps are used in some embodiments due to their combined advantages of more consistent controlled release and relatively small size (see, e.g., PCT International Application Publication No. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. A further exemplary device that can be adapted for the present disclosure is the Synchromed infusion pump (Medtronic).

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

Suitable excipient vehicles for a compound disclosed herein are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly (ortho) esters, polypeptides, hyaluronic acid, collagen, chondroitin sulfate, carboxcylic acids, fatty acids, phospholipids, polysaccharides, nucleic acids, polyamino acids, amino acids such as phenylatanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the polypeptide, antibody or fragment thereof (as well as combination compositions) is delivered in a controlled release system. For example, a compound disclosed herein may be administered using intravenous infusion, an implantable osmotic pump, a transdermal patch, liposomes, or other modes of administration. In one embodiment, a pump may be used (Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990) Science 249:1527-1533.

In another embodiment, the compositions of the present disclosure (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The present disclosure provides methods and compositions for the administration of a one or more of an interfering agent to a host (e.g., a human) for the treatment of a microbial infection. In various embodiments, these methods disclosed herein span almost any available method and route suitable for drug delivery, including in vivo and ex vivo methods, as well as systemic and localized routes of administration.

Therapeutic Methods

The isolated peptides and immunogenic compositions as described herein can be used in a method of eliciting an immune response in a subject, comprising administering to the subject an effective amount of the composition, thereby eliciting an immune response in the subject. An effective vaccine should stimulate either or both cellular and humoral immune responses against the target pathogen or pathogenic agent. The the immune response comprises a humoral response, and optionally a CD4+ T cell response, a CD8+ T cell response, or both. In one aspect, the subject is a mammal, e.g., a canine, a feline or a human patient. The subject is infected with the pathogen or is at risk of exposure, e.g., the peptide serves as a vaccine to raise an immune response.

Thus, routes of administration applicable to the methods disclosed herein include intranasal, intramuscular, urethrally, intratracheal, subcutaneous, intradermal, transdermal, topical application, intravenous, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery include systemic or localized routes. In general, routes of administration suitable for the methods disclosed herein include, but are not limited to, direct injection, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The agents disclosed herein can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods disclosed herein, the interfering agent will be administered by inhalation, injection or orally on a continuous, daily basis, at least once per day (QD), and in various embodiments two (BID), three (TID), or even four times a day. Typically, the therapeutically effective daily dose will be at least about 1 mg, or at least about 10 mg, or at least about 100 mg, or about 200 to about 500 mg, and sometimes, depending on the compound, up to as much as about 1 g to about 2.5 g.

Dosing of can be accomplished in accordance with the methods disclosed herein using capsules, tablets, oral suspension, suspension for intra-muscular injection, suspension for intravenous infusion, get or cream for topical application, or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In certain embodiments, compositions exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies (in certain embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Bioinformatics Methods for Identifying Immunogenic Epitopes

Further provided herein is a method comprising: (a) generating a plurality of control-experiment pairs of datasets, each pair comprising: (i) a control dataset comprising experimental peptides purified based on immunoglobulins from a first subject that is not immunized to a pathogenic agent, and (ii) a corresponding experiment dataset comprising control peptides purified based on immunoglobulins from a second subject that is immunized to the pathogenic agent; (b) applying an epitope model to the pairs of datasets to identify, based on which peptides are more abundant in each experimental dataset than in the corresponding control dataset, a set of one or more candidate epitopes; and (c) formulating a vaccine or a cellular therapy for the pathogenic agent based on the set of candidate epitopes.

In one embodiment of the method, the epitope model comprises generating a frequency for peptides occurring more abundantly in the experiment datasets relative to the corresponding control datasets.

In another embodiment of the method, applying the epitope model comprises generating a matrix that scores each peptide based on whether experimental peptide level was greater than, equal to, or lower than control peptide level in each pair. In one embodiment of the system, the epitope model does not include determining an average log fold change in abundance. In one embodiment of the system, the epitope model does not employ a t-test to identify peptides with a significantly higher average abundance in experimental datasets as compared to control datasets.

In a yet further aspect of the method, the method further comprises randomizing the matrix to determine statistical significance.

In one embodiment, the method further comprises generating a plurality of input datasets corresponding to the plurality of control-experiment pairs of datasets, each input dataset comprising input peptides isolated from the pathogenic agent.

In one embodiment, the method further comprises isolating input peptides from the pathogenic agent without affinity purification.

In another aspect, the method further comprises normalizing input datasets against each other based on median ratios for peptides occurring in every input dataset.

In one embodiment, the method further comprises comprising normalizing the experimental and control datasets against their respective input datasets based on the median ratios.

In another aspect, the method further comprises for each pair, purifying control peptides using antibodies from the first subject, and purifying experimental peptides using antibodies from the second subject.

In one aspect, the method further comprises performing evolutionary conservation analysis on control and experimental peptides to identify the candidate epitopes. In one aspect, the evolutionary conservation analysis comprises generating an average amino acid conservation score.

In a further aspect, the method further comprises formulating the vaccine or the cellular therapy for the pathogenic agent comprises formulating a peptide vaccine that employs multiple synthetic linear epitopes from the disclosed set of candidate epitopes (i.e. SEQ ID NOs: 1-91). In some embodiments, immunogenic peptides are chemically synthesized by standard methods. In some embodiments, immunogenic peptides are chemically synthesized by emerging technologies. One such process is described in W. Lu et al., Federation of European Biochemical Societies Letters. 429: 31-35, 1998. In some embodiments, peptides are produced using molecular genetic techniques, such as by inserting a nucleic acid encoding a peptide into an expression vector, introducing the expression vector into a host cell, and isolating the peptide.

Also provided is a system comprising a processor and a non-transitory storage medium comprising instructions which, when executed by the processor, cause the system to: (a) generate a plurality of control-experiment pairs of datasets, each pair comprising: (i) a control dataset comprising experimental peptides purified based on immunoglobulins from a first subject that is not immunized to a pathogenic agent, and (ii) a corresponding experiment dataset comprising control peptides purified based on immunoglobulins from a second subject that is immunized to the pathogenic agent; and (b) apply an epitope model to the pairs of datasets to identify, based on which peptides are more abundant in each experimental dataset than in the corresponding control dataset, a set of one or more candidate epitopes, wherein applying the epitope model comprises generating a frequency for peptides occurring more abundantly in the experiment datasets relative to the corresponding control datasets.

In one embodiment, the instructions further cause the system to generate a matrix that scores each peptide based on whether experimental peptide level was greater than, equal to, or lower than control peptide level in each pair. In another aspect, the instructions further cause the system to randomize the matrix to determine statistical significance. In one embodiment of the system, the epitope model does not include determining an average log fold change in abundance. In one embodiment of the system, the epitope model does not employ a t-test to identify peptides with a significantly higher average abundance in experimental datasets as compared to control datasets.

In one embodiment, the instructions further cause the system to generate a plurality of input datasets corresponding to the plurality of control-experiment pairs of datasets, each input dataset comprising input peptides isolated from the pathogenic agent.

In one embodiment, the instructions further cause the system to normalize input datasets against each other based on median ratios for peptides occurring in every input dataset. Alternatively, the instructions further cause the system to normalize the experimental and control datasets against their respective input datasets based on the median ratios. Yet further, the instructions further cause the system to perform evolutionary conservation analysis on control and experimental peptides to identify the candidate epitopes.

In one embodiment of the system, the evolutionary conservation analysis comprises generating an average amino acid conservation score. In one aspect, the evolutionary conservation analysis comprises checking for the presence of the peptide in the genome of all sequenced strains of the pathogen.

Further provided herein is a non-transitory computer-readable storage medium comprising instructions which, when executed by a processor of a system, cause the system to: (a) generate a plurality of control-experiment pairs of datasets, each pair comprising: (i) a control dataset comprising experimental peptides purified based on immunoglobulins from a first subject that is not immunized to a pathogenic agent, and (ii) a corresponding experiment dataset comprising control peptides purified based on immunoglobulins from a second subject that is immunized to the pathogenic agent; and (b) apply an epitope model to the pairs of datasets to identify, based on which peptides are more abundant in each experimental dataset than in the corresponding control dataset, a set of one or more candidate epitopes, wherein applying the epitope model comprises generating a frequency for peptides occurring more abundantly in the experiment datasets relative to the corresponding control datasets.

In one aspect, the non-transitory computer-readable storage medium further comprises instructions that cause the system to generate a matrix that scores each peptide based on whether experimental peptide level was greater than, equal to, or lower than control peptide level in each pair. In another aspect, the non-transitory computer-readable storage medium further comprises instructions that cause the system to randomize the matrix to determine statistical significance.

In one embodiment of the non-transitory computer-readable storage medium, the epitope model does not include determining an average log fold change in abundance.

In another aspect of the non-transitory computer-readable storage medium, the epitope model does not employ a t-test to identify peptides with a significantly higher average abundance in experimental datasets as compared to control datasets.

In one aspect, the non-transitory computer-readable storage medium further comprises instructions that cause the system to generate a plurality of input datasets corresponding to the plurality of control-experiment pairs of datasets, each input dataset comprising input peptides isolated from the target pathogenic agent. Alternatively, the instructions cause the system to normalize input datasets against each other based on median ratios for peptides occurring in every input dataset. Yet further, the instructions cause the system to normalize the experimental and control datasets against their respective input datasets based on the median ratios.

In another aspect, the non-transitory computer-readable storage medium, further comprises instructions that cause the system to perform evolutionary conservation analysis on control and experimental peptides to identify the candidate epitopes. In one aspect, the evolutionary conservation analysis comprises generating an average amino acid conservation score.

In a further aspect, the evolutionary conservation analysis comprises checking for the presence of the peptide in the genome of all sequenced strains of the pathogen.

The methods and systems were used to identify epitopes in the proteome of *Francisella tularensis* (Ft), a Select Agent with a well-characterized immunoproteome. Using the methods disclosed herein many peptides were identified that mapped to verified antigens, including verified and predicted outer membrane proteins and extracellular proteins, validating the utility of this novel process of identifying immunogenic peptide. The methods were also used to identify seroreactive peptides in a less characterized immunoproteome of Select Agent *Burkholderia pseudomallei* (Bp), which is described herein.

This screen revealed verified Bp antigens as well as proteins that have not been previously identified as antigens. Although B-cell epitope prediction tools Bepipred 2.0 and iBCE-EL classified many of the seroreactive peptides as epitopes, they did not score them significantly higher than the non-reactive tryptic peptides in the study, nor did they assign higher scores to seroreactive peptides from known Ft or Bp antigens, highlighting the need for experimental data instead of relying on computational epitope predictions alone. In some embodiments, the method of the present is used to detect peptide targets relevant to the immune systems in mice. In some embodiments, the method of the present is used to detect peptide targets relevant to the immune systems in all mammalian species, including but not limited to rats, rabbits, goats, pigs, guinea pigs, camels, horses, llamas, such primates, and non-primates, humans (depending upon the availability of convalescent sera from patients). In some embodiments, the methods of the present disclosure aid in accelerating the discovery of B cell epitopes (antibody) and development of vaccines to counter emerging biological threats.

Peptide-based subunit vaccines are coming to the forefront of current vaccine approaches, with safety and cost-effective production among their top advantages. Peptide vaccine formulations consist of multiple synthetic linear epitopes that together trigger desired immune responses that can result in robust immune memory. The advantages of peptide epitopes are their simple structure, ease of synthesis, and ability to stimulate immune responses by means that do not require complex 3D conformation. Prediction of linear epitopes through use of computational tools is fast and cost-effective, but typically of low accuracy, necessitating extensive experimentation to verify results. On the other hand, identification of linear epitopes through experimental screening has been an inefficient process that requires thorough characterization of previously identified full-length protein antigens, or laborious techniques involving genetic manipulation of organisms.

Utilizing peptide antigens for vaccine development has several advantages over typical vaccine development efforts. First, similar to other types of subunit vaccines, peptide vaccines represent a safer alternative to traditional vaccines because the vaccine formulation is defined and contents are fully synthetic. Second, peptide vaccines have the potential to decrease the cost and production timeline because of lower development risks for this class of vaccines. Third, use of short peptides sufficient for stimulation of immune response favors exclusion of deleterious sequences that may be present in full length antigenic proteins. Fourth, Peptide vaccine formulations are defined and their contents fully synthetic, which simplifies quality control procedures and thereby streamlines the regulatory approval process. Fifth, production of peptide vaccines is expected to be relatively fast and inexpensive, due to ease of synthesis and recent advances in improved peptide stability. Lastly, once antigenic peptides are identified, screening for efficacy could represent a lesser challenge due to the possibility of multiplexing peptides during in vivo trials, rather than a one-at-a-time approach.

In some embodiments, the method disclosed herein for the identification of pathogenic peptides is used as a tool for fast response to emerging biological threats. Their potential of being efficiently identified and screened for efficacy makes peptides ideal candidates for rapid countermeasure development. The present disclosure provides a platform that combines experimental and computational elements to support rapid development of peptide-based vaccines and therapeutic antibodies. In one hand, the present disclosure provides a method that leveraged a screening method that enabled efficient identification of antigenic epitopes in pathogens recently developed by Franco et al.—to downselect protective vaccine candidates. On the other hand, the present disclosure provides a machine learning workflow recently developed for prediction of therapeutic antibodies was re-purposed to predict antibodies using protective peptides as a starting point. Accordingly, in some embodiments, the present disclosure provides a novel process for a timely response to emerging disease outbreaks.

The present disclosures were motivated by the pressing need for rapid countermeasure discovery against emerging biological threats. The present disclosure provides methods for a rapid response capability for identification of protective peptides for design of peptide-based vaccines and peptide-specific therapeutic antibodies. Owing to the recent technological advancements in the field of immunology, there are currently over 500 peptide vaccines in clinical trials (Li, et al., 2014; Skwarczynski and Toth 2016; and Malonis, et al., 2019). Among them are vaccines against pathogens that have eluded conventional vaccine strategies, e.g. Malaria, Influenza, human immunodeficiency virus (HIV), hepatitis C virus (HCV), Cytomegalovirus (CMV), and Hand foot and mouth disease. Linear B cell epitopes are ideal candidates for peptide vaccine because of their ability to induce the immune system without proper folding and complex 3D conformation requirements. Linear epitopes are also ideal because of their efficient identification and in vivo efficacy screening that could support the rapid response time necessary for our preparedness for newly emerging. Because peptides have simple structure, peptides can be easily synthesized, multiplexed into vaccine formulations and efficiently screened for efficacy. Consequently, peptides represent promising candidates for fast response countermeasures. The present disclosure relied on the combination of bioscience experimentation and high-performance computing to provide new potential solutions to emerging disease outbreaks.

In some embodiments, two intracellular bacterial pathogens, *Franciscella tularensis* (Ft) and *Burkholderia pseudomallei* (Bp), organisms which pose a high risk for misuse as bioweapons and therefore are considered Tier 1 Select Agents by the US Centers for Disease Control and Prevention. The mortality rates of both pathogens are high and there is currently no licensed vaccine available for either agent (Dienst 1963, Fulton et al. 2011, Gibney and Cheng 2019).

Humoral immunity plays an important role in developing immune protection to both of these intracellular pathogens making them good model organisms for the purpose of this study. In addition, the immunoproteome of Ft has been thoroughly characterized, such that previously published data could be compared to the datasets generated in this study. We leveraged a merged dataset of 164 previously identified antigens, which makes up ~10% of Ft proteome (with 1667 total proteins in Ft proteome). The Bp immunoproteome is not as well characterized compared to that of Ft, our referenced dataset contained only 67 previously identified seroreactive proteins (Felgner et al 2009) in the Bp proteome of 6203 proteins (~1% of all Bp proteins were identified as antigens). Consequently, the dataset resulting from the Bp screen has revealed many proteins that have not been previously categorized as antigens.

EXAMPLES

The present technology is further illustrated by the following Examples, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology.

Example 1: Experimental Materials and Methods

Bacterial strains and culture conditions. *Franciscella tularensis* SCHU S4ΔclpB ("Ft-ΔclpB") was a generous gift from Dr. Wayne Conlan (National Research Council Canada). Stock cultures were prepared by growing Ft-ΔclpB on Chocolate II Agar plates supplemented with hemoglobin and isovitalex (BD 221169) for 48 hours at 37° C. Bacteria were harvested by scraping confluent lawns into Mueller Hinton (MH) broth containing 20% w/v sucrose and stored at −80° C. at a concentration 108-109 CFU/mL. *Burkholderia pseudomallei* mutant ΔpurM ("Bp82") was obtained from BEI resources (NR-51280). Frozen stocks were prepared by growing the bacteria to log phase in Luria Bertani (LB) broth, adding glycerol to achieve 20% w/v with the bacteria at a final concentration of 108-109 CFU/mL, and storing aliquots at −80° C. For immunizations, the Ft-ΔclpB and Bp82 bacterial stocks were thawed and diluted in sterile phosphate-buffered saline (PBS) to the specified concentrations used for dosing. For protein extraction purposes, Ft-ΔclpB and Bp82 were propagated to log phase in MH and LB broth, respectively. Both bacterial strains used in this study are classified as Risk Group 2 organisms. All biological materials were handled under standard institutional biosafety and biosecurity procedures, as outlined in an approved Institutional Biosafety Committee (IBC) protocol.

Protein extraction and peptide preparation. The Ft-ΔclpB and Bp82 strains were grown to log phase in 300 mL of MH broth or LB broth, respectively, at 37° C. with shaking (250 rpm). Bacteria were harvested by centrifugation at 3200×g for 10 min at 4° C., washed once with 10 mL of PBS, and the pellet flash frozen using dry ice. Bacteria in the pellet were lysed by subjecting them to two freeze-thaw cycles (alternating between room temperature and dry ice). For protein extraction, the lysate was mixed with Bper Complete Bacterial Protein Extraction Reagent (Thermo Fisher Scientific, cat #89822), and the mixture was incubated at room temperature for 15 min with rotational shaking. Following incubation, the mixture was then subjected to two rounds of sonication (1 sec pulses, timed output 10 sec, at 50% power) using a Heat Systems Ultrasonics sonicator (model W-385), and centrifuged at 16,000×g for 10 min. Proteins were precipitated with acetone and washed twice with ethanol. Air-dried protein pellets were solubilized using 8M urea and Protease Max surfactant (Promega, V2071), then digested with trypsin (Promega, V5111) using the in-solution digestion protocol provided by the manufacturer (Promega, TB373). The completion of trypsinization reaction was confirmed with DNA gel assay (data not shown). The trypsin-digested proteins were filtered using 10K MWCO concentrators (Pierce) at 10,000×g for 20 min at 20° C., and the filtrates (purified peptides) was stored at −20° C. These purified peptides preparations were used as inputs in subsequent experiments.

Mice and Immunizations. Mouse immunization studies were carried out in strict accordance with the recommendations in the Guide for the Care and Use of Laboratory Animals and the National Institutes of Health. Standard institutional safety and biosecurity procedures were followed for in vivo experiments. Appropriate efforts were made to minimize suffering of animals. All animals were housed in ABSL2 conditions in an Association for Assessment and Accreditation of Laboratory Animal Care International (AAALAC)-accredited facility, and the protocol (Protocol 270, renumbered 284, approved Oct. 9, 2017) was approved by the Lawrence Livermore National Laboratory (LLNL) Institutional Animal Care and Use Committee (IACUC).

For immunization, 6 week-old female specific-pathogen-free BALB/c-Elite and C57BL/6J-Elite mice (Charles River) were injected subcutaneously with 106 CFU Ft-ΔclpB (BALB/c and C57BL/6J) or intradermally with 107 CFU Bp82 (BALB/c), including PBS-dosed controls for each injection route, and boosted at 2 weeks. No adjuvants were used. The course of infection was monitored by performing daily health scoring and weight measurements. Mice that developed infection wounds (Ft only) were topically treated with Dakin's solution to encourage wound healing, and allowed to remain on test based on their weight loss. Mice with approximately 20% body weight loss or overt signs of morbidity were humanely euthanized. Sera from euthanized mice were excluded from analysis due to lack of immunity to the pathogen. Convalescent sera were harvested from resilient mice at 4 weeks post-infection, via cardiac puncture terminal bleeding under inhaled isoflurane anesthesia followed by blood fractionation by centrifugation at 3800×g for 15 min in microtainer serum separator tubes (BD)]. Sera were stored at −80° C.

SDS-PAGE and Western analysis. Western blot (immunoblot) analysis was performed to confirm the seropositivity of immunized mice. Bacterial lysates were prepared using Bper Complete Bacterial Protein Extraction Reagent (Thermo Fisher Scientific, cat #89822), combined with Laemmli loading buffer (BioRad), and boiled at 95° C. for 5 min. Samples were loaded onto 4-15% acrylamide gels (Mini-Protean TGX, BioRad) and separated by electrophoresis at 120 V for 1 hr. The proteins were transferred from the gels to nitrocellulose membranes (BioRad). Membranes were blocked with Tris-buffered saline plus 0.05% Tween 20 (TBS-T) plus 5% nonfat dry milk, for 1 hr or 16 hrs. The membranes were hybridized with mouse sera at 1:500 dilution in TBS-T plus 5% milk, at room temperature for 2 hrs; washed three times with TBS-T; and then incubated with goat anti-mouse antibodies conjugated to Horseradish peroxidase (HRP) (Pierce, prod #1858413) at 1:5000 dilution in TBS-T plus 5% milk at room temperature for 1 hr. After three TBS-T washes, the membranes were developed using SuperSignal™ West Pico PLUS Chemiluminescent Substrate (Thermo Fisher Scientific).

Enzyme-linked immunosorbent assay (ELISA). ELISA was performed to assess the level of seropositivity of immunized mice. Wells were coated with bacterial lysates and incubated at 4° C. for 16 hrs. After three washes with PBS plus 0.1% Tween-20 (PBS-T), sera from immunized mice diluted to 1:100 with PBS were added to the wells and incubated at room temperature for 1 hr. Following four PBS-T washes, the wells were incubated for 1 hour with Recombinant Protein A/G peroxidase (Pierce, cat #32490) diluted at 1:5000 with PBS. After four PBS-T washes, 1-Step ABTS Substrate Solution (cat #37615) was added, and after 15 min incubation any colorimetric changes in the wells were detected using a microplate reader (Tecan M200 Pro).

Affinity purification of immunoreactive peptides. Magnetic beads coated with protein G (Invitrogen, cat #10007D) or protein A were used to capture antibodies from pools of sera obtained from either infected (experiment) mice or mock-infected (control) mice, following the manufacturer's protocol (MAN0017348). Each pool was comprised of sera recovered from 3-5 mice, with equal volumes used for each experiment-control pair. The antibody-coated beads were then incubated with peptide preparations (inputs) at room temperature for 45 min. Antibody-coated beads from each experiment-control pair were incubated with the same input peptides; in total, 6 input peptide preparations were used with the 8 Ft experiment-control pairs, and 5 with the 9 Bp experiment-control pairs. Following three PBS washes, immunoreactive peptides were eluted from the beads using citrate buffer (pH 3). Input, unbound, and eluted (output) peptides were flash frozen with dry ice and stored at −20° C. As a negative control, antibodies from non immunized (PBS treated) mice were used to detect any background resulting from nonspecific binding of peptides to beads or antibodies.

Mass spectrometry (MS). The input, unbound, and eluted (output) peptides recovered from antibody-coated beads (see preceding section) were desalted using an Empore SD solid phase extraction plate, lyophilized, reconstituted in 0.1% TFA, and analyzed via LC-MS/MS by MS Bioworks (Ann Arbor, Michigan), using a Waters M-Class UPLC system interfaced to a ThermoFisher Fusion Lumos mass spectrometer. Peptides were loaded on a trapping column and eluted over a 75 μm analytical column at 350 nL/min. Both columns were packed with Luna C18 resin (Phenomenex). A 2 hr gradient was employed. The mass spectrometer was operated in a data dependent HCD mode, with MS and MS/MS performed in the Orbitrap at 60,000 FWHM resolution and 15,000 FWHM resolution, respectively. The instrument was run with a 3 sec cycle for MS and MS/MS.

MS data processing. Data were analyzed using Mascot (Matrix Science) with the following parameters: Enzyme: Trypsin/P; Database: UniProt *F. tularensis* SCHU S4 or UniProt *B. pseudomallei* strain 1026b (forward and reverse appended with common contaminants and mouse IgG sequences); Fixed modification: Carbamidomethyl (C); Variable modifications: Oxidation (M), Acetyl (N-term), Pyro-Glu (N-term Q), Deamidation (N/Q); Mass values: Monoisotopic; Peptide Mass Tolerance: 10 ppm; Fragment Mass Tolerance: 0.02 Da; Max Missed Cleavages: 2; Mascot DAT files were parsed into Scaffold Proteome Software for validation, filtering and to create a non-redundant list per sample. Data were filtered using 1% protein and peptide FDR and requiring at least one unique peptide per protein.

Bioinformatic analysis. Each experiment typically consisted of three sets of data: "Input" (total bacterial peptides without affinity purification), "Control" (peptides purified from beads coated with antibodies from non immunized mice), and "Experiment" (peptides purified from beads coated with antibodies from immunized mice). LC-MS/MS data were analyzed at the peptide level based on the Total Ion Current (TIC, total area under the MS2 curve) as a metric for the abundance of the peptide in each sample, rather than rolling up peptide scores into a protein abundance metric as would be done in standard proteomics. Input datasets were first normalized against each other based on median ratios for the peptides occurring in every Input dataset. The more sparse Control and Experiment datasets were then normalized against their respective Input dataset based on median ratios as well.

Since each animal was expected to raise a different set of antibodies, how often specific output peptides occurred more abundantly in the Experiment vs Control was counted, rather than focusing on the average log fold change in abundance. For each peptide and each Experiment sample, an enrichment score of +1, 0, or −1 was assigned depending on whether the normalized peptide abundance was greater than, equal to, or lower in the Experiment than in the corresponding Control sample, creating a score matrix of peptides×Experiments. The total enrichment score for each peptide was then the sum of its enrichment scores across each Experiment. Statistical significance was evaluated by generating a number of randomized score matrices, where each peptide was randomly assigned a +1, 0, or −1 score for each Experiment, with the same probabilities as in the real matrix, and calculating how frequently peptides reach an specific total enrichment score. This gave a background level of how many high-scoring peptides would be expected even if there was no correlation in peptide abundance across the different experiments, which can then be used to calculate the significance level of observing a given number of high scoring peptides in the real data, using a simple binomial test comparing expected vs observed number of peptides exceeding a given score.

This analysis method was novel and not previously used in the art. The standard analytical method used in the art required performing a T-test to find peptides that have a significantly higher average abundance in Experiment vs Control. However, applying this conventional method only yielded a very small number of significant peptides, likely because the response across experimental animals was highly variable. Analytical method of the present disclosure is a novel way of analyzing high throughput data when, as here, a response across experimental animals is highly variable. Thus a novel and unique aspect of the present disclosure was using the analytical process described herein, which provided highly significant results as described herein.

Average Amino Acid Conservation Scores (AAACS) were calculated using the ConSurf web server (Ashkenazy et al. 2016) using default parameter values, using near full-length protein structure homology models from SWISS-MODEL or crystal structures from PDB where available. The AAACS for the peptide is the average conservation score for the residues in the peptides, with negative scores indicating more highly conserved regions (Ren et al., 2014). These scores are normalized position-specific evolutionary rates, with negative scores indicating the most conserved amino acids. The Average Amino Acid Conservation Score (AAACS), proposed by Ren et al as a useful tool to identify conserved epitopes that may be targeted by broadly neutralizing antibodies, is the average of the conservation score for the residues in an epitope, with negative scores indicating more highly conserved regions (32).

In addition to AAACS, peptides were also scored based on how many complete sequenced genomes of pathogenic *B. pseudomallei* and *F. tularensis*. This analysis was similar to the conservation analysis in Epitocore (Fiuza et al., 2020). The proteomes for all 110 *B. pseudomallei* strains with complete genomes sequenced available through NCBI were downloaded. For *F. tularensis*, 36 strains with complete genomes were available through NCBI, but several of these corresponded to the less-pathogenic novicida, holartica and mediasiatica subspecies. Accordingly, the analysis was focused exclusively on the 17 available subsp. *tularensis* complete genomes. Homologs with at least 90% sequence identity to the proteins containing our top scoring peptides in Tables 1 and 2 (FIGS. 7 and 8) were identified, and then each peptide was scored based on how often they had a 100% identical hit in each homolog.

Two state of the art computational B cell epitope prediction tools were used to evaluate all the peptides in our proteomic data matching the proteins in Tables 1 and 2 (FIGS. 7 and 8). Peptides were submitted to the iBCE-EL web server for scoring (Manavalan et al., 2018)]. iBCE-EL is an ensemble-based method based on extremely randomized tree and gradient boosting classifiers, trained on 5,550 experimentally validated B-cell epitopes and 6,893 non-epitopes from the Immune Epitope Database, to identify linear B-cell epitopes. In addition, proteins were submitted to the Bepipred Linear Epitope Prediction 2.0 tool on the IEDB website (Jespersen et al., 2017), and peptides were then scored based on their average predicted residue score. Bepipred 2.0 is a random forest classifier trained on 160 non-redundant antigen-antibody crystal structures, to predict the probability that a given antigen residue is part of an epitope.

Example 2: Overview of Immunoproteome Screen

The feasibility of proteome-wide screening for linear B cell epitopes using peptide extracts from target bacteria and sera from immunized animals was tested. The high-throughput method for proteome-wide screening for linear B cell epitopes using peptide extracts requires of:
(1) isolation of peptides from lysates generated from the target bacteria; (2) immunization of the host (in this case, mouse) with the target bacteria, followed by collection of convalescent serum; (3) admixing the bacterial peptides and convalescent serum, to allow peptide antigens to bind to their cognate antibodies in the serum; and (4) recovery of bound peptides for identification through mass spectrometry (FIG. 1).

This process was applied to two bacterial Select Agent pathogens: *Francisella tularensis* and *Burkholderia pseudomallei*. Infection with attenuated strains of these pathogens (*F. tularensis* SCHU S4ΔclpB and *B. pseudomallei* ΔpurM (strain Bp82) has been shown to stimulate the development of protective immunity against their corresponding fully-virulent parental strains (*F. tularensis* SCHU S4 and *B. pseudomallei* K96245, respectively) (Conlan et al. 2010, Propst et al. 2010). Accordingly, convalescent sera recovered from hosts infected with these attenuated strains of *F. tularensis* SCHU S4ΔclpB and *B. pseudomallei* ΔpurM (strain Bp82) must contain protective antibodies.

Briefly, proteins purified from pathogen lysates, were digested with trypsin to generate a peptide library. Mice were infected with a sublethal dose of Ft ΔclpB or Bp ΔpurM, and immune status assessed through measurement of seroreactivity to pathogen lysate via enzyme-linked immunosorbent assay (ELISA) or Western blot analysis (FIG. 2). Antibodies purified from the convalescent sera of immunized mice were immobilized on magnetic beads and then incubated with pathogen-derived peptides to allow formation of antigen-antibody complexes. Peptides recovered from the immobilized antibodies were identified via liquid chromatography coupled with tandem mass spectrometry.

Example 3: Bioinformatic Analysis of Datasets

The peptides recovered using pooled sera from infected mice (Experiment peptidome) were compared to those recovered from mock-infected mice (Control peptidome). A total of 8 pairs of Control and Experiment peptidomics for *Francisella*, and 9 for *Burkholderia* was collected. For *Francisella*, out of the 1923 peptides that were recovered in at least two Experiment peptidomes, 44 peptides had an enrichment score of 6 or greater (Table 1 in FIG. 7; e.g., scored at least 6 out of 8); whereas only 20.1+/−6.1 peptide such high scoring peptides would have been expected at random ($p=1\times10^{-5}$; Table 1 in FIG. 7). Out of these 44 peptides, 5 peptides were derived from proteins that have never been shown to have antigenic properties. In particular, the five peptides were derived from an aminotransferase, encoded by the aspC1 gene, a trigger factor encoded by the tig gene, an outer membrane protein 26 encoded by the omp26 gene, a 3-oxoacyl-(Acyl-carrier-protein) reductase encoded by the fabG gene, and an enoyl-[Acyl-carrier-protein] reductase [NADH] encoded by the fabI gene. Moreover, the analysis identified multiple epitope within a single gene. In particular, the 60 kDA chaperonin was hit four times; the chaperone protein Dnak was hit 8 times; elongation factor Ts was hit three times.

For *Burkholderia*, out of 2902 peptides that were recovered in at least two Experiment peptidomes, 46 peptides had an enrichment score of least 6 or greater, (Table 2 in FIG. 8); whereas only 17.8+/−4.3 would have been expected at random ($p=1.9\times10^{-9}$). If a more stringent enrichment cutoff is desired, we found 16 Ft peptides with an enrichment score of 7 or greater, versus 3.5+/−1.6 expected at random ($p=1.8\times10^{-7}$), and 20 Bp peptides with an enrichment score of 7 or greater, versus 4.1+/−2.1 expected at random ($p=3.9\times10^{-9}$).

The enriched peptides included those some that were derived from a number of protective antigens identified in previous studies, as well as predicted outer membrane and extracellular proteins (Table 1 (FIG. 7), Table 2 (FIG. 8), Tables 5 and 6). There were many examples of multiple enriched peptides originating from the same protein (highlighted in bold in the tables), a further indication that enrichment was not random but rather due to immune response to a discrete set of bacterial proteins.

C57BL/6J mice were used for two of the eight Ft experimental samples, because of previously reported differences in protection and antibody response after immunization of C57BL/6J and BALB/c mice with Ft-ΔclpB by Twine et al, Vaccine 30 (24): 3634-45 (2012). Analyzing the BALB/c Ft samples separately yielded a very similar set of results as shown in Table 1 in FIG. 7, but with lower p-value for the enrichment due to the smaller number of samples (results data not shown). Therefore, the data was combined and the analysis was focused on antibody responses in common between both strains of mice. Twine et al. only reported an antibody response against chaperonin protein GroL only in BALB/c mice. However, data of the present disclosure showed that there were several GroL epitopes that were enriched in samples from both mouse strains (Table 1 in FIG. 7, Table 5 and FIG. 6).

Prior immunoproteomics analysis of the antibody response to *F. tularensis* using human or mouse sera identified 164 antibody targets out of a total of 1667 proteins screened (~10% of the entire Ft proteome) (19,27,28). In constrats, the present inventors found that out of the 1923 peptides that have hits in at least two Ft datasets, 876 peptides matched known antigenic proteins. Given those numbers, only 20 such peptides would have been expected to show up at random in the disclosed list of 44 shown in Table 1 in FIG. 7. Instead, the present inventors found that 38/44 peptides in the list correspond to known antigens, which is an almost two-fold enrichment ($p=2.79\times10^{-9}$). Moreover, despite the extensive literature on antigens in Ft, only five B-cell epitopes have been experimentally determined (FIG. 6, panel B), justifying the need for a simple experimental epitope screening method. The immune response to *B. pseudomallei* has not been studied in as much depth as for *Francisella*. So even though Bp with 6203 protein coding genes has a genome that is more than three times as large as that of Ft, only 61 known antigens identified in previous studies (29,30) (~1% of the entire proteome) were found using the methods disclosed herein. The list of 46 top Bp peptides disclosed in Table 1 in FIG. 7 includes one known antigen, which does not qualify as a statistically significant enrichment primarily because of the much smaller total number of known antigens for Bp.

FIG. 5 shows all 46 Ft Dnak peptides that were detected in at least two Experiment samples, regardless of their degree of enrichment. Eight of these DnaK peptides were included in the list of 44 enriched Ft peptides (Table 1 in FIG. 7; FIG. 5, panel A, everything above the the x-axis), including two that are enriched in all 8 Experiments (FIG. 5, panel A, everything above the the x-axis). Note the lack of correlation between the experimental enrichment scores and the iBCE-EL and Bepipred scores (FIG. 5 panels B and C). All but one of the 8 enriched peptides were conserved in all 17 fully sequenced Ft strains (FIG. 5, panel E), but some of the peptides towards the C-terminal show a greater evolutionary rate as measured by their Average Amino Acid conservation Score (AAACS, FIG. 5, panel D) and thus may be more prone to immune escape mutants.

FIG. 6 shows all 32 Ft GroL peptides that were detected in at least two Experiment samples, regardless of the degree of their enrichment. Four of these GroL peptides were included in the list of 44 enriched Ft peptides (Table 1 in FIG. 7 and red line segments in FIG. 6, panel A, everything above the the x-axis), including three that are enriched in all eight Experiments. Lu et al., PLOS One 9 (6): e99847 (2014) used hydrogen/deuterium exchange-mass spectrometry (DXMS) to experimentally identify one discontinuous and four linear B-cell epitopes for a selection of mouse monoclonal antibodies against GroL (FIG. 6, panel B). Note that one of the four enriched peptides in FIG. 6, panel A (DNTTIIDGAGEK; SEQ ID NO: 7) overlaps with a linear epitope (NTTIIDGAGEKEAIAKRINVIK; SEQ ID NO: 97) and a discontinuous epitope (SEDLSMKLEETNM (SEQ ID NO: 98)—NTTIIDGAGEKEAIA; SEQ ID NO: 99) identified by DXMS in FIG. 6, panel B, while a second enriched peptide (EGVITVEEGK; SEQ ID NO: 8) is directly adjacent to another of the linear DXMS epitopes (FEDEL; SEQ ID NO: 100). According to the Immune Epitope Database (IEDB; Vita et al., Nucleic Acids Res. 47 (D1): D339-43 (2019)), these are the only experimentally validated B-cell epitopes for Ft. The IEDB also lists four *B. pseudomallei* antigens that have been assayed for B-cell epitopes, none of which overlap with the novel proteins and epitopes disclosed herein (e.g., Table 1; FIG. 7).

The top scoring lists included multiple protective antigens identified in previous studies, predicted outer membrane or extracellular proteins (based on prediction of subcellular localisation by psortb), and proteins with multiple high scoring peptides, providing independent validation of our results (highlighted below in bold, Tables 1 and 2, FIGS. 7 and 8). Prioritizing highly conserved epitopes is a critical consideration as highly conserved epitopes can induce broadly protective immunity, thereby emergence of pathogen variants will not render the vaccine ineffective (see pubmed.ncbi.nlm.nih.gov/31331771/). 90% of the top scoring peptides were found to be present in 90% or more of the fully sequenced pathogenic *B. pseudomallei* and *F. tularensis* strains (Tables 3 and 4 (FIGS. 9A-9C and 10A-10C)). In addition, target peptides that show even deeper evolutionary conservation based on their Average Amino Acid Conservation Score were detected. These peptides reflect parts of the protein that may be important for protein function (Ashkenazy et al., 2016) (Tables 3 and 4 (FIGS. 9A-9C and 10A-10C)).

This immunoproteomic methods identified numbers peptide candidates that map to previously identified antigens and subunit vaccine targets, predicted membrane-associated proteins as well as uncharacterized proteins. *Francisella* datasets revealed a significant enrichment of peptides belonging to previously identified antigenic proteins in experimental samples compared to controls, providing validation to this approach. Additional validation was achieved by the observation of several antigens containing multiple significant peptide hits.

The present disclosure provides a widely applicable shotgun immunoproteomic method that enables efficient identification of B cell epitopes in the proteomes of pathogens. The results disclosed herein revealed a significant enrichment of peptides derived from previously identified antigens and vaccine candidates, validating the method's efficacy. This novel method was designed to identify linear epitopes efficiently without the need of genetic manipulation or other experimental techniques that can be costly and labor intensive. Attenuated strains made the optimization of this process more efficient. However the availability of an attenuated strain for the target organism does not represent a limitation to the present disclosure as this strategy could be applied to fully virulent strains of pathogens. Although an embodiments of the present disclosure was performed in a mouse model, the method of the present disclosure could be easily adapted to detecting targets relevant to the human immune system using convalescent sera from patients.

Among *Francisella tularensis* proteins described in the present disclosure are two well-characterized antigens, 60 kDa chaperonin GroL and chaperone protein DnaK. Both chaperones have been previously implicated in virulence of *Francisella* (Noah et al. 2010, Pechous, McCarthy, and Zahrt 2009, Weiss et al. 2007); and are known to induce antibody production in mice and humans (Havlasova et al. 2005, Huntley et al. 2007, Kilmury and Twine 2010). These chaperonin proteins are important for folding nascent translating proteins and post-translational modification. They are also known as heat-shock proteins. Heat-shock proteins protect cellular proteins from environmental stresses such as high temperature or induced by low Ph or increased temperatures (Ericsson et al. 1994, Huntley et al. 2007). Although their cellular localization is predicted to be cytoplasmic, they also associate with membrane proteins and are released into host cells during infection (Henderson, Allan, and Coates 2006, Hickey et al. 2009, Huntley et al. 2007, Lee, Horwitz, and Clemens 2006). The release into host cell is one mechanism that contributes to heat shock proteins ability to stimulate various immune functions, including innate immunity, humoral immunity and cell-mediated immunity (Ashtekar et al. 2008, Huntley et al. 2007, Kol et al. 1999, Noah et al. 2010, Wallin et al. 2002, Valentino et al. 2011). However, the role of host immune processes, such as post phagocytes pathogen cell lysis cannot be discounted. Therefore, Heat-shock proteins represent good candidates for subunit vaccine design due to their ability to stimulate various immune responses without the need of adjuvant. Both GroL and DnaK have been exploited for vaccine development efforts targeting *Francisella* and other pathogens (Ashtekar et al. 2012, Huntley et al. 2007, Khan et al. 2009, Lu et al. 2014).

Among Ft proteins, the present screen identified multiple peptides for two well-characterized antigens, 60 kDa chaperonin GroL (Q5NEE1) and chaperone protein DnaK (Q5NFG7). Both chaperonins have been previously implicated in virulence of *Francisella* and are known to induce antibody production in mice and humans. These chaperonin proteins are important for facilitating folding of nascent proteins as well as post-translational modifications. They are also known as heat-shock proteins, as they protect cellular proteins from environmental stresses such as high temperature and low Ph. Although their cellular localization is predicted to be cytoplasmic, they reportedly also associate with membrane proteins and are released into host cells during infection perhaps contributing to their ability to stimulate various immune functions, including innate immunity, humoral immunity and cell-mediated immunity. Heatshock proteins are good candidates for subunit vaccine design due to their ability to stimulate various immune responses without the need of adjuvant; in fact, both GroL and Dnak have been exploited for vaccine development efforts targeting *Francisella* and other pathogens.

Highly virulent Type A *Francisella* strains such as SCHU S4 can bind host plasminogen to the bacterial cell surface where it can be converted to plasmin, a serine protease that degrades opsonizing antibodies, inhibiting antibody-mediated uptake by macrophages. Among the 25 Ft proteins listed in Table 1 in FIG. 7, at least 3 are known to be involved in plasminogen binding in *Francisella* or other pathogens, including conserved hypothetical lipoprotein LpnA (Q5NGE4), fructose-1,6-bisphosphate aldolase (Q5NF78), and elongation factor Tu (Q5NID9). These proteins could make for particularly attractive vaccine targets, because interfering with their function before the pathogen has activated its plasmin-mediated antibody evasion, would make it more susceptible to other antibodies as well.

Among antigenic peptides identified in the Bp proteome are those belonging to Type VI secretion system component, Hhcp-1, and previously identified antigen, 10 kDa chaperonin GroES (Varga et al. 2012). Hcp-1 was previously found to be a major virulence determinant in *Burkholderia pseudomallei* and recognized by sera from infected human patients and animals (Burtnick et al. 2011, Schell et al. 2007, Whitlock et al. 2010). Due to this, Hcp-1 has been interrogated as a potential candidate for *Burkholderia* vaccine development (Burtnick et al. 2011, Schell et al. 2007, Whitlock et al. 2010). A peptide from an ankyrin repeat-containing protein (A0A0H3HJC) came up as one of the highest scoring results. Ankyrin repeats are typically eukaryotic protein domains involved in protein-protein interactions (Li et al. 2006), but have been co opted by many bacterial pathogens as type IV secreted effector proteins to mimic or manipulate various host functions (Pan et al. 2008). Notably, a genomic island containing four ankyrin repeat-containing proteins along with several other putative pathogenicity-related genes has been found in some clinical *B. cenocepacia* and *B. pseudomallei* strains.

Recovery of peptides derived from several supposedly cytosolic enzymes may seem puzzling. However several "housekeeping" enzymes are known to be displayed on the surface of pathogens where they play a role in virulence. For example, the top scoring peptides from *B. pseudomallei* include two derived from enolase (A0A0H3HLA6). While enolase is primarily thought of as a key glycolytic enzyme, it is also expressed on the surface of a wide variety of bacterial and fungal pathogens, where it interacts with host plasminogen and is associated with invasion and virulence. Antibodies against enolase have been detected in a large variety of infectious and autoimmune diseases. It is as yet unknown whether enolase plays the same role in *Burkholderia*, but the protein is predicted to be present both in the cytoplasm and on the cell surface, and its production was found to be upregulated upon exposure to human lung epithelial cells. Other housekeeping proteins in the top scoring results whose homologs in other pathogens are known to play a role in adhesion, invasion, or virulence include elongation factor Tu (Q5NID9), malic enzyme/ malate dehydrogenase (A0A0H3HP28, Q5NHC8), and fructose-1,6-bisphosphate aldolase (Q5NF78).

Overall, this immunoproteomic workflow has identified numerous peptides mapping to previously identified antigens and subunit vaccine targets, predicted membrane-associated proteins as well as uncharacterized proteins. *Francisella* datasets revealed a significant enrichment of peptides belonging to previously identified antigenic proteins in Experiment samples relative to their respective Control samples, providing validation to this approach. Interestingly, several of these known antigens also yielded multiple top scoring peptides in our analysis. Despite the large amount of prior immunoproteomic analysis on Ft, covering ~10% of the genome, experimentally validated B-cell epitopes are available for only a single protein, and our analysis captures two out of its five known epitopes. Due to the much smaller number of previously identified antigens for *Burkholderia*, we were not able to tell whether the enrichment in the Bp datasets was significant. Improved proteome coverage and more comprehensive immunogenic profiles could be achieved with the use of alternative enzymes with different specificities since there is a risk of ablating epitopes that contain cut sites recognized by specific enzymes such as trypsin. Alternatively, performing incomplete digestion with one enzyme, or a cocktail of enzymes with different specificities, could increase the number of overlapping peptides and thereby improve the yield and diversity of identified epitopes. In addition, since the methods disclosed herein are dependent upon extraction of proteins from whole cell lysates, it is conceivable that the proteome coverage could be biased toward highly abundant proteins or those proteins that are easier to extract. Despite this potential disadvantage, several low abundant protein, such as membrane-bound antigens were detected using the methods disclosed herein.

A variety of computational B-cell epitope prediction tools to identify epitopes in antigens are known in the art. However accurate computational prediction of B-cell epitopes still poses a major challenge, with sensitivity or specificity typically below 60%, leading some recent in-silico multi-epitope vaccine design efforts to look at the consensus of up to 8 or 9 B-cell epitope prediction tools simultaneously. The recent development of prediction tools using state-of-the-art machine learning models that claim significantly higher performance on large benchmarking datasets seems promising. The present inventors compared the performance of Bepipred 2.0 (35), one of the most widely used B-cell prediction tools, and Ibce-EL; and found no significant correlation between the peptides experimentally identified using the method described herein and computationally predicted linear B-cell epitope scores generated by Bepipred 2.0 and Ibce-EL, even for those antibody-binding peptides belonging to known Ft or Bp antigens, nor do they find any significant correlation between the Bepipred 2.0 and Ibce-EL scores themselves. The methods disclosed herein and the exemplified embodiments shown in Examples 1-9 highlight the value and novelty of the unbiased experimental methods for screening for antibody targets disclosed herein.

At their default score thresholds, Ibce-EL correctly predicts 34/44 of the Ft peptides, and 39/46 of the Bp peptides, while Bepipred 2.0 correctly predicts 21/44 Ft peptides and 13/46 Bp peptides, but that is not actually significantly more than would be expected at random given their hit rates on other un-enriched tryptic peptides in our dataset. Part of the discrepancy between the computational Bepipred 2.0 predictions and our experimental results may be due to the fact that Bepipred 2.0 is trained on antigen-antibody 3D structures, which likely contain a mix of conformational and linear epitopes. In addition, Bepipred 2.0 has a relatively low self-reported 58.6% sensitivity and 57.2% specificity at the default score threshold of 0.5, and thus is expected to exhibit a large number of false positives and false negative predictions. Ibce-EL is reported to have better sensitivity and specificity (73.2% and 72.4%), but explicitly takes into account sequence features at the beginning and end of the epitope that may be missing in the tryptic peptides generated here, affecting their score. In cases where the tryptic peptide is too short to be used directly as a vaccine candidate (some are as short as 6 residues), these computational tools may be used to guide those skilled in the art with how to extend the boundaries of the peptide beyond its flanking trypsin cleavage sites.

Computational B cell prediction tools such as these are trained to distinguish epitopes from non-epitopes in known antigens, but are not an effective alternative to experimentally screening for epitopes across an entire bacterial proteome. For example, on a random selection of 100 Ft and Bp proteins, Bepipred-2.0 using its default epitope threshold of 0.5 classified 40% of all amino acids as being part of an epitope, including an average of 5.5 peptides of length 9 or longer per protein (data not shown). Likewise, on a random selection of 1000 tryptic peptides from all our proteomics data, Ibce-EL classified 81% as B-cell epitopes using its default score threshold of 0.35 (data not shown). Applied across the entire proteome, the computational approach would predict tens of thousands of putative B-cell epitopes, likely with a high false-positive rate and, regardless, providing little guidance in winnowing the possibilities for experimental verification.

If so desired, peptides can be downselected for vaccine development by focusing only on those with the most stringent enrichment scores, or based on consensus with computational epitope prediction tools. Further downselection may include prioritizing highly conserved epitopes that can induce broadly protective immunity, and reduce the risk that emergence of pathogen variants will render the vaccine ineffective. ~ 90% of the top scoring peptides were found to be present in 90% or more of the fully sequenced pathogenic *F. tularensis* and *B. pseudomallei* strains. In addition, target peptides that show even deeper evolutionary conservation based on their Average Amino Acid Conservation Score (AAACS) can be targeted, reflecting parts of the protein that may be important for its function. Peptides that are only one or two amino acids different from human or mouse versions are likely less suitable as vaccine candidates and are marked with a subscript 1 or 2 respectively in Tables 1 and 2 (FIGS. 7 and 8). Note that while some of the proteins in Tables 1 and 2 (FIGS. 7 and 8) have homologs in human and mouse (e.g. mitochondrial DnaK), the peptides recovered here are unique to the bacterial versions. For vaccine design, peptides which do not tend to occur in healthy human microbiomes may be prioritized, by comparing them against some of the large human metaproteomics datasets recently generated.

Further confirmation that the identified sequences are B cell epitopes could be achieved through additional in vitro and in vivo experimentation (e.g., testing the reactivity of immune sera with synthesized candidate epitopes via ELISA or immunization studies). High throughput screening of peptides for efficacy is feasible due to recent advancements in solid phase peptide synthesis (SPPS), which enables efficient and cost-effective production of peptide candidates (3). For immunization studies, pools of multiple peptides could be incorporated into vaccine delivery systems containing adjuvants and T-helper epitopes known to stimulate the induction of adaptive immune response against peptide antigens, as reviewed in Skwarczynski et al (3).

Further confirmation that identified sequences are B cell epitopes could be achieved through additional in vitro and in vivo experimentation (e.g. testing the reactivity of immune sera with synthesized candidate epitopes via ELISA or through immunization studies). High throughput screening of peptides for efficacy is feasible due to recent advancements in solid phase peptide synthesis (SPPS) that allows efficient and cost-effective production of peptide candidates (Skwarczynski et al, 2016). For immunization studies, multiple peptides can be incorporated through various synthetic techniques into vaccine delivery systems containing adjuvants and T-helper epitopes known to stimulate the induction of adaptive immune response against peptide antigens (Skwarczynski et al, 2016).

This immunoproteomic method represents a new tool for precise mapping of linear B cell and T cell epitopes. Generation of such immunogenic profiles for pathogens could provide an ample pool of candidates for further experimental validation and efficient vaccine development. The methods disclosed herein provide an accelerating method for discovering of B cell epitopes in the proteomes of pathogens that will help fuel the development of peptide-based vaccines. These peptide-based vaccines will provide rapid solutions to biothreat agents and emerging pathogens.

Example 4: Developing a Screening Platform for Peptides that Contribute to Protective Immunity Against Pathogens Examples 1-3 above disclose a method that enables efficient identification of B cell epitopes (antibody epitopes) in the proteomes of pathogens using convalescent sera from immunized animals. This method was designed to identify linear epitopes without the need of proteome library construction, proteomic arrays, phage displays or other currently employed techniques that are costly and cumbersome. Examples 1-3 show that enrichment of peptides that map to verified antigens and outer membrane proteins (a class of proteins that are generally antigenic), thereby validating the efficacy of the novel method of the present disclosure. Indeed, this novel method was successfully applied in two distinct pathogens-*Burkholderia pseudomallei* and *Francsisella tularensis*, which are classified as Tier 1 Select Agent pathogens to which no effective vaccines currently exist. To our knowledge, the present disclosure is the first high-throughput proteome-wide screening approach for the identification of linear B cell epitopes (antibody epitope).

Datasets generated in example 1-3 will be leveraged to build an in vivo platform for discovery of peptides that induce protective immune response or lead to partial protectivity to a pathogen. The pathogen contemplated by the present disclosure include, but are not limited to Abrin, *Bacillus cereus* Biovar *anthracis*, Botulinum neurotoxins, Botulinum neurotoxin producing species of *Clostridium*, Conotoxins (Short, paralytic alpha conotoxins containing the following amino acid sequence X1CCX2PACGX3X4X5X6CX7 (SEQ ID NO: 101)), *Coxiella burnetii*, Crimean-Congo haemorrhagic fever virus, Diacetoxyscirpenol, Eastern Equine Encephalitis virus, Ebola virus, Lassa fever virus, Lujo virus, Marburg virus, Monkeypox virus, influenza virus, Ricin, *Rickettsia prowazekii*, SARS-associated coronavirus (SARS-CoV1 and 2), Saxitoxin, South American Haemorrhagic Fever viruses such as Chapare Guanarito, Junin, Machupo, Sabia Staphylococcal enterotoxins (subtypes A,B,C,D,E), T-2 toxin, Tetrodotoxin, Tick-borne encephalitis complex (flavi) viruses, such as Far Eastern subtype, Siberian subtype, Kyasanur Forest disease virus, Omsk hemorrhagic fever virus, *Variola major* virus (Smallpox virus), *Variola minor* virus (Alastrim), *Yersinia pestis, Bacillus anthracis, Bacillus anthracis* Pasteur strain, *Brucella abortus, Brucella melitensis, Brucella suis, Burkholderia mallei*, Hendra virus, Nipah virus, Rift Valley fever virus, or Venezuelan equine encephalitis virus.

Figure 3:
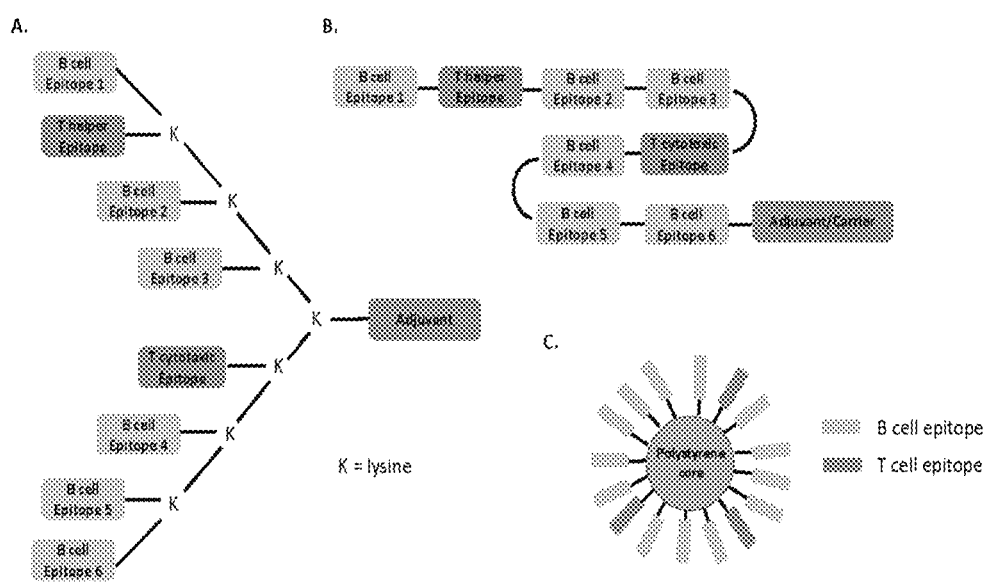
FIG. 3 shows schematics illustrating three synthetic methods for high-throughput peptide presentation and delivery, which will employ solid phase peptide synthetic approach (SPPS) to multiplex epitopes in vaccine formulations. Method A involves a long peptide made of epitopes subsequently conjugated to adjuvant/carrier. Method B incorporates epitopes via stepwise SPPS and lysine-based branching. Method C involves conjugation of peptides to polysterene beads. (Figure adapted from Skwarczynski et al, 2016).
Figure 4A:
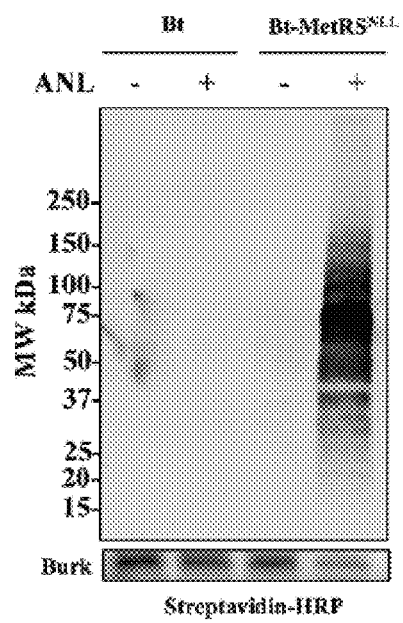
FIGS. 4A-E show the expression of a variant (RNA methionine synthase (MetRS$^{NLL}$) in *B. thailandensis* (Bt), which led to incorporation of azidonorleucine (Anl) into Bt proteins, and Anl-labeling of Bt-MetRS$^{NLL}$ during infection is bacteria-specific and allows for in-situ fluorescent detection of host-associated bacteria.
Figure 4B:
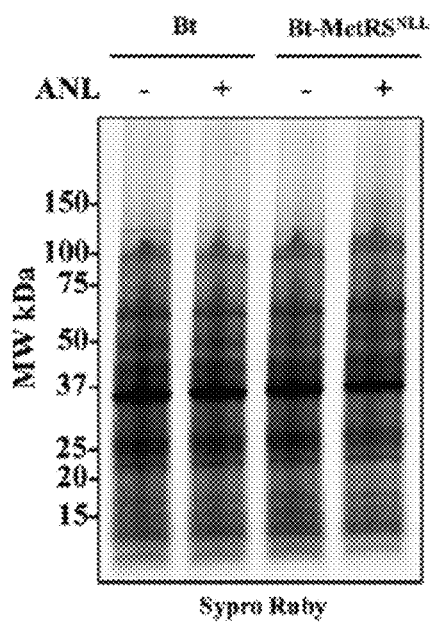
Figure 4C:
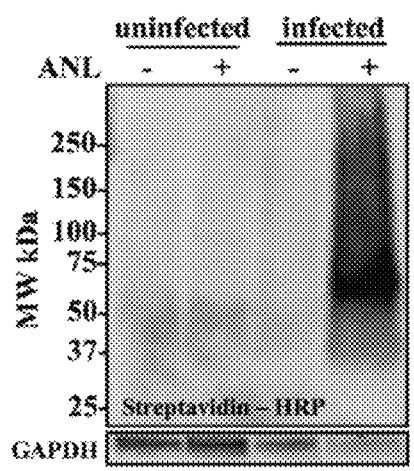
Figure 4D:
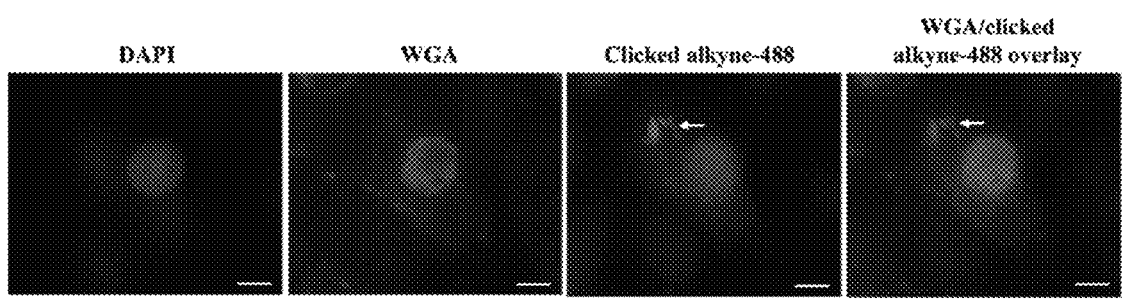
Figure 4E:
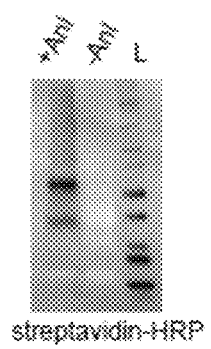
Figure 5:
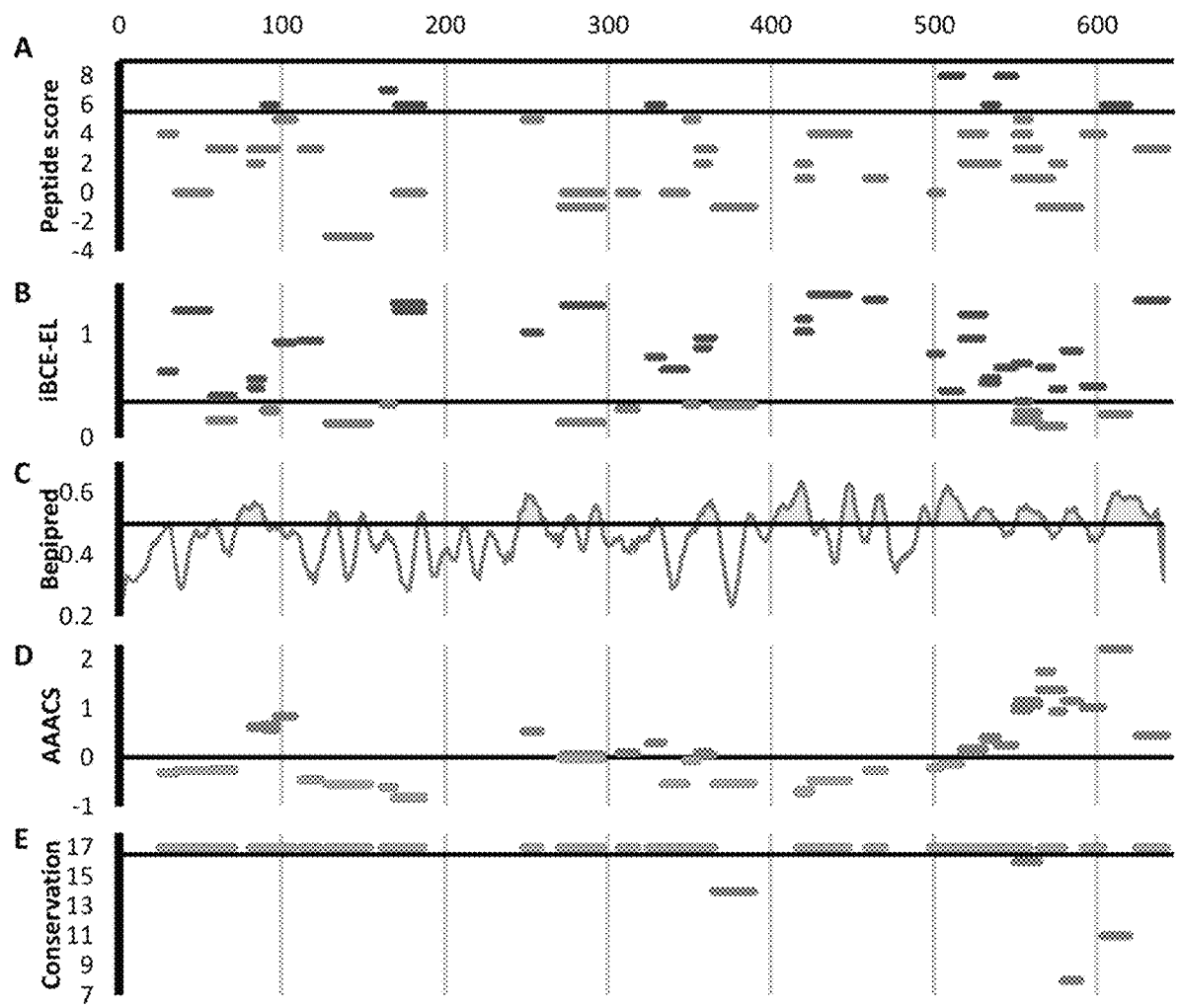
FIG. 5 shows a schematic representations of the scoring for the 46 *F. tularensis* (FT) DnaK peptides detected in at least two Experiment samples. The short horizontal line segments in panels A, B, E and F indicate the position of a peptide along the length of the 642 amino acids of the DnaK protein, and the vertical position within each figure panel indicates its score for the metric indicated. The default score threshold for each tool is shown with a horizontal line, and the peptides or per-amino acid scores exceeding that threshold are shown in color. Panel A shows a peptide enrichment score based on proteomics results. An enrichment score of 8 indicates that the peptide was detected in greater abundance in all 8 experiment samples relative to their respective Control samples. The threshold for inclusion in Table 1 (FIG. 7) was an enrichment score of ≥6 (everything above the the x-axis). Panel B shows B-cell epitope prediction score generated using iBCE-EL. At the default iBCE-EL score threshold of 0.35, nearly three quarter of all peptides were predicted to be likely B-cell epitopes (everything above the the x-axis). Panel C shows B-cell epitope prediction score generated using Bepipred 2.0. The per-amino acid scores are indicated by the line graph. At the default iBCE-EL score threshold of 0.35, 37% of all amino acids were predicted to be in B-cell epitopes (regions of the graph shown in a shade; everything above the x-axis). Panel D shows average Amino Acid Conservation Score (AAACS) based on Consurf analysis. Negative scores indicate greater degrees of evolutionary conservation (everything below the x-axis). Panel E shows number of fully sequenced *F. tularensis* subsp. *tularensis* genomes (17 analyzed) in which each peptide occurs. Almost all of the DnaK peptides considered were conserved in all 17 *F. tularensis* (Ft) genomes (shown above the x-axis).
Figure 6:
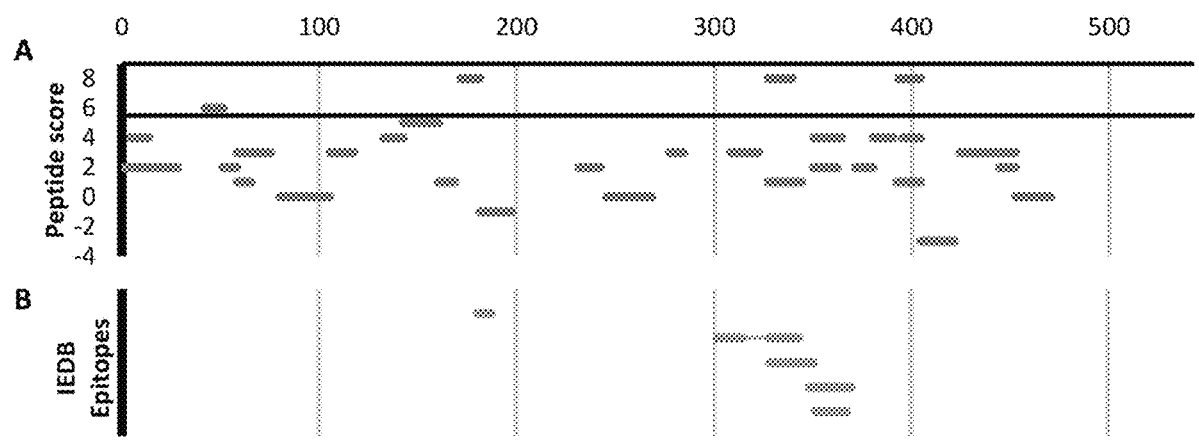
FIG. 6 shows a schematic representations of the 32 *F. tularensis* GroL peptides detected in at least two Experiment samples. Horizontal line segments indicate the position of each peptide along the length of the 544 amino acids of the GroL protein sequence. Panel A shows a peptide enrichment score based on proteomics results, with a score of 8 indicating that the peptide was found in greater abundance in all 8 Experiment samples relative to their respective Control samples. The threshold for inclusion in Table 1 (FIG. 7) was a score of ≥6 or better (everything above the x-axis). Panel B shows five B-cell epitopes identified by DXMS by Lu et al. PLOS One 9 (6): e99847 (2014), including one discontinuous epitope.

High throughput screening of peptides for efficacy is feasible due to recent advancements in solid phase peptide synthesis (SPPS) that allows fully automated, fast and cost-effective production of large pool of peptide candidates (Skwarczynski and Toth, 2016). The effectiveness of at least three synthetic approaches will be compared to test ~6-10 epitopes at a time (FIG. 3). In addition, the capacity of this system will be determined. For example, the maximum amount of B cell epitopes that can be screened at a time will be assessed. Each formulation will contain a diverse set of epitopes, including CD4 helper T cell and CD8 cytotoxic T cell epitopes to ensure proper stimulation of adaptive immune response. The technological field's current knowledge and existing epitope prediction tools including Immune Epitope Database (IEDB) (Fleri, et al., 2017) and EigenBio platform (Bremel and Homan a, 2010 (a); Bremel and Homan, 2010 (b)) will be used to identify T cell epitopes that will be included in peptide vaccines. Commonly used adjuvants, carrier proteins and/or other previously described vaccine components (e.g. antigen-presenting cell homing peptides) to enhance the immune response will be employed. Peptide combinations that achieve increased protection will inform the optimization of subsequent experimental formulations.

The method is highly versatile and will allow the screening of multiple distinct peptides at a time (including B cell epitopes, T cell epitopes, APC homing peptides, etc. to target specific immune responses). This platform will enable rapid de novo design of vaccine formulations that stimulate robust and diverse immune response and help exclude epitopes that have immunosuppressive properties.

Example 5: In-Silico Prediction of Therapeutic Antibodies Specific to Protective Peptides Unlike vaccines that provide delayed but long-term protection to a pathogen, therapeutic antibodies offer immediate short-term protection to uninfected individuals and can decrease mortality and morbidity of infected patients. Having access to both types of countermeasures is imperative during pandemic scenario. To date, several therapeutic antibodies have been developed as a countermeasure to pathogenic organisms and proved useful in containing recent deadly outbreaks of Ebola virus (Pelfrene et al., 2019).

Accordingly, a recently developed computational platform (Desautels et al.) for computational prediction and editing of monoclonal antibodies based on the knowledge of antigen structure will be used for data analysis. A major application of this platform is the rapid-response design of antibodies against emerging pathogens. In contrast to standard methods in the art, which are critically reliant on known, neutralizing antibodies against closely homologous pathogens, targeting linear epitopes as described herein is more general and is essentially independent of a previous body of literature.

Designing antibodies against linear epitopes will be approached as a machine learning problem, in which applicant will predict the structure of antibodies that will bind to a linear peptide (epitope) identified using the methods described in Example 4. Data generated in example 4 will be used as training and validation data for performing this prediction. Additional data will be obtained using a recently developed commercial system (Younger et al., 2017) that harnesses yeast mating to measure the all vs. all affinities of two collections of sequences. Here the two collections of sequences will be those of antibodies and peptide antigens. The tools used in the computational design platform described herein will be used to characterize potential antibody/peptide antigen interfaces and make binding/no-binding classification predictions from these using deep Gaussian process classification. This classification problem gives a starting point for design of antibodies against specific peptide targets. Initial antibody designs will be generated by iteratively submitting different antibodies with the target peptide to the classifier and keep those with the highest binding probability. These initial designs will then be refined with the rest of the machinery of the platform for structure-based antibody design.

The novel approach will generate large antibody-peptide binder and nonbinder datasets that will provide valuable insights on patterns involved in peptide-antibody binding. This data will be used for in silico design of antibodies purely based on known amino acid sequence of a protective linear epitope and have the potential to generate therapeutic antibody candidates in days. The data will have a great impact on the nation's ability to deploy therapeutics to emerging biothreats in a rapid manner.

The delivery of vaccine formulations for in vivo validation of the proposed method could prove to be a challenge, as vaccine delivery in itself is a challenging task that often requires optimization. To mitigate this risk, standard methods will be used that maximize stimulation of the immune system (e.g. optimal dosing and booster shots, use of adjuvants to enhance the recruitment of immune cells to the site of injection, conjugation of carrier proteins to peptides to improve antigen presentation to immune cells).

Example 6: Generate a Peptide Library by Purifying Proteins Produced by Intracellularly Growing Bacteria A rapid screening method that enables efficient identification of protective epitopes for use in peptide vaccines against biothreat agents to which no successful vaccines currently exist will be developed. The method will combine the reliability of in vivo experimentation with the high throughput nature of mass spectrometry and bioinformatics for identification of candidate immunogenic epitopes for development of effective and safe vaccine formulations. As in Examples 1-3 above, the method will be used to identify protective epitopes produced by *Francisella tularensis*. However, the method will be designed to enable identification of protective immunogens produced by any intracellular bacterial pathogen, including other biothreat agents such as *Burkholderia pseudomallei* and *Yersinia pestis*. Since non-protective immunodominant epitopes tend to be highly variable across related species, candidate immunogenic peptides that are highly conserved will be prioritized. This analysis will generate a comprehensive set of highly conserved immunogenic epitopes for use in development of effective broad-spectrum vaccine against *F. tularensis*.

Accordingly, a widely applicable approach for rapid detection of highly conserved immunogenic epitopes in *F. tularensis* will be developed. *F. tularensis* is a biothreat agent for which no effective vaccine currently exists. The identification will be achieved through affinity purification of pathogen-specific peptide-antibody complexes followed by peptide identification via mass spectrometry followed by bioinformatics analyses to focus on highly conserved peptides.

There are several innovative aspects to this work. First, peptide libraries will be generated from bacteria growing within host cells, rather than in conventional culture. Better approximation of the infection context should provide access to epitopes that are not otherwise expressed by the bacteria. Second, the unique methodology described herein will enrich for bacterial proteins over those originating from the host, thereby minimizing contamination of peptide preparations with host material prior to screening. Third, the use of mass spectrometry to identify bound peptides will enable rapid generation of profiles of immunogenic peptides, such that through comparison of results obtained from different sera it will be possible to assess hostspecific variations. Fourth, the use of bioinformatics tools to focus on highly conserved peptides within the candidate epitope library will aid in eliminating hypervariable regions (which represent the common cause that renders vaccines ineffective), and will potentially aid in discovering peptides that confer protection against pathogen variants. The combination of in vivo obtained sera with mass spectrometry analyses makes this a powerful high-throughput strategy that can drive development of vaccines effective against a variety of pathogenic organisms.

To better recapitulate infection conditions, applicant will extract proteins from intracellular bacteria, rather than from conventionally cultured bacteria. One key advantage of this approach is the potential for detecting novel immunogenic epitopes, as many virulence-related proteins are produced only during infection (Casey and McClean 2015; Wiersinga et al., 2012). The method described below offers a powerful strategy for isolating bacteria-specific peptides from intracellularly grown bacteria.

This effort will take advantage of an orthogonal amino acid labeling methodology that enables selective purification of proteins expressed by bacteria growing within eukaryotic host cells (Mahdavi et al., 2014; Wier et al., 2015). A mutant variant of methionyl Trna-synthetase (MetRSNLL), which preferentially incorporates the methionine (Met) surrogate azidonorleucine (Anl) into bacterial proteins, will be stably expressed in the *Francisella tularensis* SCHU S4ΔclpB strain, which is a well characterized non-select agent model for fully virulent *Francisella tularensis* (Ft) (Golovliov et al., 2013; Conlan et al., 2010; and Meibom et al., 2008). Briefly, the *E. coli* MetRSNLL gene will be codon optimized for efficient expression in *Francisella* spp., synthesized commercially, and ectopically expressed in Ft SCHU S4ΔclpB strain using a shuttle vector that has been widely used for expression of genes in Ft, including SCHU S4 strains (Maier et al., 2004; Peng et al., 2011; Lindgren et al., 2014). The resulting strain will express Anl-labeled proteins (upon addition of Anl into the media), which will allow for selective purification of bacterial proteins via alkyne-labeling of azide groups present on Anl and subsequent affinity purification of labeled proteins (Mahdavi et al., 2014; Wier et al., 2015).

To generate a peptide library, bacteria will be grown in human primary monocytes cultured in media supplied with 1 Mm Anl for 24 hrs. Any extracellular bacteria will be washed off and their further growth prevented using antibiotics at 2 hrs post-infection (hpi). Infected cells will be lysed at 24 hpi, and Anl-labeled bacterial proteins purified as previously described using alkyne-functionalized biotin (Mahdavi et al., 2014; Wier et al., 2015). Biotinylated proteins will then be affinity purified using streptavidin columns, and peptides eluted through trypsin digestion. FIG. 4A-E show successful labeling and purification of AnI-tagged proteins within bacterial lysates from *B. thailandensis* strain (Bt) E264 (FIG. 4A-D; Franco et al., 2018) and *Escherichia coli* (FIG. 4E) ectopically expressing a variant *E. coli* methionyl-Trna synthetase (MetRS$^{NLL}$). In addition, expression of MetRS$^{NLL}$ within Ft will be accomplished using by targeted gene integration into the genome of Ft with a MiniTn7 expression system (Su et al., 2014; Norris et al., 2010; Choi et al., 2005).

Collection of peptides from proteins expressed by intracellularly grown bacteria will be generated, and will be screened for immunogenic epitopes in the next steps of this study.

Example 7: Isolate Polyclonal IgG Antibodies from Mice Infected with Live Bacteria The newly identified peptide library of Example 6 will be screened for pathogen epitopes that are able to stimulate protective immunity in mice. Female BALB/c mice will be infected intradermally (ID) with sublethal doses of Ft SCHU S4ΔclpB as previously described by (Conlan et al., 2010). Immunization of mice using Ft SCHU S4 ΔclpB increase pathogen-specific IgG and IgM antibodies in the mice sera and stimulate protective immunity of mice to subsequent challenges by wild-type Ft SCHU S4 (Conlan et al., 2010).

Sera will be collected from 20 mice at 28 days post-exposure, which corresponds to the time at which the concentration of protective antibodies in the sera should be at its peak. Crude sera from each animal will be tested for antigen-specific reactivity to whole bacterial lysates via Western blotting, and the most reactive sera selected for further analysis. Total IgG antibodies from selected sera will be affinity purified using protein A magnetic beads, and the beads (still coated with antigen-specific IgG antibodies) used to purify immunogenic peptides in the next task.

Since more relevant results for vaccine purposes should be generated from clinically obtained human sera, screening for peptides using human sera will also be assessed. However, analysis using mouse sera will be advantageous because of the minimal inter-individual variation with regard to host physiology as well as infection parameters (pathogen strain, dose, delivery route and timing, etc.), making it easier to obtain reliable results for this proof-of-concept study.

A polyclonal IgG antibodies from immunized mice will be obtained and will be used in the next step to purify *F. tularensis* peptides that have the ability to elicit protective immunity in mice.

Example 8: Purify Antibody-Peptide Complexes and Identify Bound Pathogen-Derived Immunogenic Peptides by Mass Spectrometry To identify pathogen-derived immunogenic peptides, peptides from the library prepared in Example 6 will be affinity purified using the IgG-bearing magnetic beads prepared in Example 7. Antibody-peptide complexes will be allowed to form before washing the beads thoroughly to eliminate nonspecific interactions. Bound peptides will be eluted by proteolytic cleavage and identified by liquid chromatography coupled to mass spectrometry (LC-MS/MS), as described by (Cheung et al., 2012). Mass spectrometry will be carried out in-house or subcontracted commercially. Epitope profiles containing sero-reactive peptides for each independent mouse infection will be generated. The comparison of results obtained from different sera will be used to assess host-specific variations.

Example 9: Bioinformatics Methodologies to Identify Highly Conserved Epitopes To identify peptides that generate protective immunity against a broad spectrum of *Francisella tularensis* variants, peptides that are conserved across previously sequenced clinical strains will be searched. Immunodominant epitopes often consist of highly variable and nonprotective decoy epitopes (Novotny et al., 2003; Guo et al., 2008; Murphy T F and Yi K (1997)). Conversely, genes that are essential for the fitness of a pathogen are typically conserved across the naturally occurring *Francisella* serovars, and tend to encode peptides that are under strong purifying selection. A search will be conducted to identify candidate epitopes that appear to be under negative evolutionary selection, by estimating the ratio of nonsynonymous versus synonymous mutations within the gene's coding region. This method has been previously shown to be successful in epitope prediction (Suzuki Y (2004); Moise et al., 2015).

The candidate list will further be narrowed by searching for peptides that exhibit reactivity with multiple sera obtained in the study. Epitopes that provoked immune response in only one animal will be eliminated from the candidate list. In this way, epitopes that exhibit host-specific variations with respect to inducing protective immunity will be avoided because they could render the peptide vaccine ineffective.

A rapid screening method that enables efficient identification of protective epitopes for use in peptide vaccines against biothreat agents to which no successful vaccines currently exist will be developed.

The approach described herein combines the reliability of in vivo experimentation with the high throughput nature of mass spectrometry and bioinformatics for identification of candidate immunogenic epitopes for development of effective and safe vaccine formulations. In some embodiments, the method will be used to identify protective epitopes produced by *F. tularensis*. In some embodiments, the method will enable identification of protective immunogens produced by any intracellular bacterial pathogen.

In some embodiments, the intracellular bacterial pathogen is selected from Abrin, *Bacillus cereus* Biovar *anthracis*, Botulinum neurotoxins, Botulinum neurotoxin producing species of *Clostridium*, Conotoxins (Short, paralytic alpha conotoxins containing the following amino acid sequence X1CCX2PACGX3X4X5X6CX7 (SEQ ID NO: 101)), *Coxiella burnetii*, Crimean-Congo haemorrhagic fever virus, Diacetoxyscirpenol, Eastern Equine Encephalitis virus, Ebola virus, Lassa fever virus, Lujo virus, Marburg virus, Monkeypox virus, influenza virus, Ricin, *Rickettsia prowazekii*, SARS-associated coronavirus (SARS-CoV1 and 2), Saxitoxin, South American Haemorrhagic Fever viruses such as Chapare Guanarito, Junin, Machupo, Sabia Staphylococcal enterotoxins (subtypes A,B,C,D,E), T-2 toxin, Tetrodotoxin, Tick-borne encephalitis complex (flavi) viruses, such as Far Eastern subtype, Siberian subtype, Kyasanur Forest disease virus, Omsk hemorrhagic fever virus, *Variola major* virus (Smallpox virus), *Variola minor* virus (Alastrim), *Yersinia pestis, Bacillus anthracis, Bacillus anthracis* Pasteur strain, *Brucella abortus, Brucella melitensis, Brucella suis, Burkholderia mallei*, Hendra virus, Nipah virus, Rift Valley fever virus, or Venezuelan equine encephalitis virus. In some embodiments, the intracellular bacterial pathogen is a biothreat agent. In some embodiments, the intracellular bacterial pathogen is a biothreat agent such as *Burkholderia pseudomallei* and *Yersinia pestis*. Since non-protective immunodominant epitopes tend to be highly variable across related species, candidate immunogenic peptides that are highly conserved will be prioritized.

In one aspect, the present disclosure provides a comprehensive set of highly conserved immunogenic epitopes for use in the development of effective broad-spectrum vaccine against *F. tularensis* or any a biothreat agent.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

REFERENCES

Ashtekar, A. R., J. Katz, Q. Xu, and S. M. Michalek. 2012. "A mucosal subunit vaccine protects against lethal respiratory infection with *Francisella tularensis* LVS." PLOS One 7 (11): e50460. doi: 10.1371/journal.pone.0050460.

Ashtekar, A. R., P. Zhang, J. Katz, C. C. Deivanayagam, P. Rallabhandi, S. N. Vogel, and S. M. Michalek. 2008. "TLR4-mediated activation of dendritic cells by the heat shock protein DnaK from *Francisella tularensis*." J Leukoc Biol 84 (6): 1434-46. doi: 10.1189/jlb.0308215.

Bi, Y., Z. Jin, Y. Wang, S. Mou, W. Wang, Q. Wei, N. Huo, S. Liu, X. Wang, Z. Yang, H. Chen, and S. Xiao. 2019. "Identification of Two Distinct Linear B Cell Epitopes of the Matrix Protein of the Newcastle Disease Virus Vaccine Strain LaSota." Viral Immunol 32 (5): 221-229. doi: 10.1089/vim.2019.0007.

Burtnick, M. N., P. J. Brett, S. V. Harding, S. A. Ngugi, W. J. Ribot, N. Chantratita, A. Scorpio, T. S. Milne, R. E. Dean, D. L. Fritz, S. J. Peacock, J. L. Prior, T. P. Atkins, and D. Deshazer. 2011. "The cluster 1 type VI secretion system is a major virulence determinant in *Burkholderia pseudomallei*." Infect Immun 79 (4): 1512-25. doi: 10.1128/IAI.01218-10.

Conlan, J. W., H. Shen, I. Golovliov, C. Zingmark, P. C. Oyston, W. Chen, R. V. House, and A. Sjostedt. 2010. "Differential ability of novel attenuated targeted deletion mutants of *Francisella tularensis* subspecies *tularensis* strain SCHU S4 to protect mice against aerosol challenge with virulent bacteria: effects of host background and route of immunization." Vaccine 28 (7): 1824-31. doi: 10.1016/j.vaccine.2009.12.001.

Dienst, F. T., Jr. 1963. "Tularemia: a perusal of three hundred thirty-nine cases." J La State Med Soc 115:114-27.

Dudek, N. L., P. Perlmutter, M. I. Aguilar, N. P. Croft, and A. W. Purcell. 2010. "Epitope Discovery and Their Use in Peptide Based Vaccines." Current Pharmaceutical Design 16 (28): 3149-3157.

Ericsson, M., A. Tarnvik, K. Kuoppa, G. Sandstrom, and A. Sjostedt. 1994. "Increased synthesis of DnaK, GroEL, and GroES homologs by *Francisella tularensis* LVS in response to heat and hydrogen peroxide." Infect Immun 62 (1): 178-83. doi: 10.1128/IAI.62.1.178-183.1994.

Fulton, K. M., X. Zhao, M. D. Petit, S. L. Kilmury, L. A. Wolfraim, R. V. House, A. Sjostedt, and S. M. Twine. 2011. "Immunoproteomic analysis of the human antibody response to natural tularemia infection with Type A or Type B strains or LVS vaccination." Int J Med Microbiol 301 (7): 591-601. doi: 10.1016/j.ijmm.2011.07.002.

Gibney, K. B., and A. C. Cheng. 2019. "Reducing the melioidosis burden: public health, chronic disease prevention, or improved case management?" Lancet Infectious Diseases 19 (8): 800-802. doi: 10.1016/S1473-3099 (19) 30303-2.

Havlasova, J., L. Hernychova, M. Brychta, M. Hubalek, J. Lenco, P. Larsson, M. Lundqvist, M. Forsman, Z. Krocova, J. Stulik, and A. Macela. 2005. "Proteomic analysis of anti-*Francisella tularensis* LVS antibody response in murine model of tularemia." Proteomics 5 (8): 2090-103. doi: 10.1002/pmic.200401123.

Henderson, B., E. Allan, and A. R. Coates. 2006. "Stress wars: the direct role of host and bacterial molecular chaperones in bacterial infection." Infect Immun 74 (7): 3693-706. doi: 10.1128/IAI.01882-05.

Hickey, T. B., L. M. Thorson, D. P. Speert, M. Daffe, and R. W. Stokes. 2009. "*Mycobacterium tuberculosis* Cpn60.2 and DnaK are located on the bacterial surface, where Cpn60.2 facilitates efficient bacterial association with macrophages." Infect Immun 77 (8): 3389-401. doi: 10.1128/IAI.00143-09.

Huntley, J. F., P. G. Conley, K. E. Hagman, and M. V. Norgard. 2007. "Characterization of *Francisella tularensis* outer membrane proteins." J Bacteriol 189 (2): 561-74. doi: 10.1128/JB.01505-06.

Jaenisch, T., K. Heiss, N. Fischer, C. Geiger, F. R. Bischoff, G. Moldenhauer, L. Rychlewski, A. Sie, B. Coulibaly, P. H. Seeberger, L. S. Wyrwicz, F. Breitling, and F. F. Loeffler. 2019. "High-density Peptide Arrays Help to Identify Linear Immunogenic B-cell Epitopes in Individuals Naturally Exposed to Malaria Infection." Mol Cell Proteomics 18 (4): 642-656. doi: 10.1074/mcp.RA118.000992.

Khan, M. N., D. Shukla, A. Bansal, S. Mustoori, and G. Ilavazhagan. 2009. "Immunogenicity and protective efficacy of GroEL (hsp60) of *Streptococcus pneumoniae* against lethal infection in mice." FEMS Immunol Med Microbiol 56 (1): 56-62. doi: 10.1111/j.1574-695X.2009.00548.x.

Kilmury, S. L., and S. M. Twine. 2010. "The *Francisella tularensis* proteome and its recognition by antibodies." Front Microbiol 1:143. doi: 10.3389/fmicb.2010.00143.

Kol, A., T. Bourcier, A. H. Lichtman, and P. Libby. 1999. "Chlamydial and human heat shock protein 60s activate human vascular endothelium, smooth muscle cells, and macrophages." J Clin Invest 103 (4): 571-7. doi: 10.1172/JCI5310.

Lee, B. Y., M. A. Horwitz, and D. L. Clemens. 2006. "Identification, recombinant expression, immunolocalization in macrophages, and T-cell responsiveness of the major extracellular proteins of *Francisella tularensis*." Infect Immun 74 (7): 4002-13. doi: 10.1128/IAI.00257-06.

Li, W., M. D. Joshi, S. Singhania, K. H. Ramsey, and A. K. Murthy. 2014. "Peptide Vaccine: Progress and Challenges." Vaccines (Basel) 2 (3): 515-36. doi: 10.3390/vaccines2030515.

Lu, Z., M. J. Rynkiewicz, G. Madico, S. Li, C. Y. Yang, H. M. Perkins, S. R. Sompuram, V. Kodela, T. Liu, T. Morris, D. Wang, M. I. Roche, B. A. Scaton, and J. Sharon. 2014. "B-cell epitopes in GroEL of *Francisella tularensis*." PLOS One 9 (6): e99847. doi: 10.1371/journal.pone.0099847.

Malonis, R. J., J. R. Lai, and O. Vergnolle. 2020. "Peptide-Based Vaccines: Current Progress and Future Challenges." Chem Rev 120 (6): 3210-3229. doi: 10.1021/acs.chemrev.9b00472.

Noah, C. E., M. Malik, D. C. Bublitz, D. Camenares, T. J. Sellati, J. L. Benach, and M. B. Furie. 2010. "GroEL and lipopolysaccharide from *Francisella tularensis* live vaccine strain synergistically activate human macrophages." Infect Immun 78 (4): 1797-806. doi: 10.1128/IAI.01135-09.

Pechous, R. D., T. R. McCarthy, and T. C. Zahrt. 2009. "Working toward the future: insights into *Francisella tularensis* pathogenesis and vaccine development." Microbiol Mol Biol Rev 73 (4): 684-711. doi: 10.1128/MMBR.00028-09.

Propst, K. L., T. Mima, K. H. Choi, S. W. Dow, and H. P. Schweizer. 2010. "A *Burkholderia pseudomallei* deltapurM mutant is avirulent in immunocompetent and immunodeficient animals: candidate strain for exclusion from select-agent lists." Infect Immun 78 (7): 3136-43. doi: 10.1128/IAI.01313-09.

Schell, M. A., R. L. Ulrich, W. J. Ribot, E. E. Brueggemann, H. B. Hines, D. Chen, L. Lipscomb, H. S. Kim, J. Mrazek, W. C. Nierman, and D. Deshazer. 2007. "Type VI secretion is a major virulence determinant in *Burkholderia mallei*." Mol Microbiol 64 (6): 1466-85. doi: 10.1111/j.1365-2958.2007.05734.x.

Skwarczynski, M., and I. Toth. 2016. "Peptide-based synthetic vaccines." Chem Sci 7 (2): 842-854. doi: 10.1039/c5sc03892h.

Valentino, M. D., Z. J. Maben, L. L. Hensley, M. D. Woolard, T. H. Kawula, J. A. Frelinger, and J. G. Frelinger. 2011. "Identification of T-cell epitopes in *Francisella tularensis* using an ordered protein array of serological targets." Immunology 132 (3): 348-60. doi: 10.1111/j.1365-2567.2010.03387.x.

Varga, J. J., A. Vigil, D. DeShazer, D. M. Waag, P. Felgner, and J. B. Goldberg. 2012. "Distinct human antibody response to the biological warfare agent *Burkholderia mallei*." Virulence 3 (6): 510-4. doi: 10.4161/viru.22056.

Wallin, R. P., A. Lundqvist, S. H. More, A. von Bonin, R. Kiessling, and H. G. Ljunggren. 2002. "Heat-shock proteins as activators of the innate immune system." Trends Immunol 23 (3): 130-5. doi: 10.1016/s1471-4906 (01) 02168-8.

Wang, A. P., N. Li, J. M. Zhou, Y. M. Chen, M. Jiang, Y. H. Qi, H. L. Liu, Y. K. Liu, D. M. Liu, J. G. Zhao, Y. W. Wang, and G. P. Zhang. 2018. "Mapping the B cell epitopes within the major capsid protein L1 of human papillomavirus type 16." International Journal of Biological Macromolecules 118:1354-1361. doi: 10.1016/j.ijbiomac.2018.06.094.

Weiss, D. S., A. Brotcke, T. Henry, J. J. Margolis, K. Chan, and D. M. Monack. 2007. "In vivo negative selection screen identifies genes required for *Francisella* virulence." Proc Natl Acad Sci USA 104 (14): 6037-42. doi: 10.1073/pnas.0609675104.

Whitlock, G. C., A. Deeraksa, O. Qazi, B. M. Judy, K. Taylor, K. L. Propst, A. J. Duffy, K. Johnson, G. B. Kitto, K. A. Brown, S. W. Dow, A. G. Torres, and D. M. Estes. 2010. "Protective response to subunit vaccination against intranasal *Burkholderia mallei* and *B. pseudomallei* challenge." Procedia Vaccinol 2 (1). doi: 10.1016/j.provac.2010.03.013.

Zhao, D. M., K. K. Han, X. M. Huang, L. J. Zhang, H. L. Wang, N. Liu, Y. J. Tian, Q. T. Liu, J. Yang, Y. Z. Liu, and Y. Li. 2018. "Screening and identification of B-cell epitopes within envelope protein of tembusu virus." Virology Journal 15. doi: ARTN 14210.1186/s12985-018-1052-1.

Li, et al., 2014. Peptide vaccine: progress and challenges.

Malonis, et al., 2019. Peptide-Based Vaccines: Current Progress and Future Challenges.

Fleri, et al., 2017. The Immune Epitope Database and Analysis Resource in Epitope Discovery and Synthetic Vaccine Design.

Bremel and Homan, 2010 (a), An integrated approach to epitope analysis I: Dimensional reduction, visualization and prediction of MHC binding using amino acid principal components and regression approaches.

Bremel and Homan, 2010 (b), An integrated approach to epitope analysis II: A system for proteomic-scale prediction of immunological characteristics.

Pelfrene, et al., 2019. Monoclonal antibodies as anti-infective products: a promising future?

Younger, et al., 2017. High-throughput characterization of protein-protein interactions by reprogramming yeast mating.

Li W, Joshi M D, Singhania S, Ramsey K H, Murthy A K (2014) Peptide Vaccine: Progress and Challenges. Vaccines (Basel) 2:515-536. Novotny L A, Bakaletz L O (2003) The fourth surface-exposed region of the outer membrane protein P5-homologous adhesin of nontypable *Haemophilus influenzae* is an immunodominant but non-protective decoying epitope. J Immunol 171:1978-1983.

Guo H, Zhou E M, Sun Z F, Meng X J (2008) Immunodominant epitopes mapped by synthetic peptides on the capsid protein of avian hepatitis E virus are non-protective. Viral Immunol 21:61-67.

Sesardic D (1993) Synthetic peptide vaccines. J Med Microbiol 39:241-242.

WHO (2014) In: vaccines Sp, editor.

Casey W T, McClean S (2015) Exploiting molecular virulence determinants in *Burkholderia* to develop vaccine antigens. Curr Med Chem 22:1719-1733.

Wiersinga W J, Currie B J, Peacock S J (2012) Melioidosis. N Engl J Med 367:1035-1044.

Mahdavi A, Szychowski J, Ngo J T, Sweredoski M J, Graham R L, et al. (2014) Identification of secreted bacterial proteins by noncanonical amino acid tagging. Proc Natl Acad Sci USA 111:433-438.

Wier G M, McGreevy E M, Brown M J, Boyle J P (2015) New method for the orthogonal labeling and purification of *Toxoplasma gondii* proteins while inside the host cell. MBio 6: e01628.

Golovliov I, Twine S M, Shen H, Sjostedt A, Conlan W (2013) A DeltaclpB mutant of *Francisella tularensis* subspecies holarctica strain, FSC200, is a more effective live vaccine than *F. tularensis* LVS in a mouse respiratory challenge model of tularemia. PLOS One 8: e78671.

Meibom K L, Dubail I, Dupuis M, Barel M, Lenco J, et al. (2008) The heat-shock protein ClpB of *Francisella tularensis* is involved in stress tolerance and is required for multiplication in target organs of infected mice. Mol Microbiol 67:1384-1401.

Maier T M, Havig A, Casey M, Nano F E, Frank D W, et al. (2004) Construction and characterization of a highly efficient *Francisella* shuttle plasmid. Appl Environ Microbiol 70:7511-7519.

Peng K, Broz P, Jones J, Joubert L M, Monack D (2011) Elevated AIM2-mediated pyroptosis triggered by hypercytotoxic *Francisella* mutant strains is attributed to increased intracellular bacteriolysis. Cell Microbiol 13:1586-1600.

Lindgren M, Tancred L, Golovliov I, Conlan W, Twine S M, et al. (2014) Identification of mechanisms for attenuation of the FSC043 mutant of *Francisella tularensis* SCHU S4. Infect Immun 82:3622-3635.

Su S, Saldanha R, Pemberton A, Bangar H, Kawamoto S A, et al. (2013) Characterization of stable, constitutively expressed, chromosomal green and red fluorescent transcriptional fusions in the select agent bacterium, *Francisella tularensis* Schu S4 and the surrogate type B live vaccine strain (LVS). Appl Microbiol Biotechnol 97:9029-9041.

Norris M H, Kang Y, Wilcox B, Hoang T T (2010) Stable, site-specific fluorescent tagging constructs optimized for *burkholderia* species. Appl Environ Microbiol 76:7635-7640.

Choi K H, Gaynor J B, White K G, Lopez C, Bosio C M, et al. (2005) A Tn7-based broadrange bacterial cloning and expression system. Nature Methods 2:443-448.

Cheung W C, Beausoleil S A, Zhang X, Sato S, Schieferl S M, et al. (2012) A proteomics approach for the identification and cloning of monoclonal antibodies from serum. Nat Biotechnol 30:447-452.

Murphy T F, Yi K (1997) Mechanisms of recurrent otitis media: importance of the immune response to bacterial surface antigens. Ann N Y Acad Sci 830:353-360.

Suzuki Y (2004) Negative selection on neutralization epitopes of poliovirus surface proteins: implications for prediction of candidate epitopes for immunization. Gene 328:127-133.

Moise L, Gutierrez A, Kibria F, Martin R, Tassonc R, et al. (2015) iVAX: An integrated toolkit for the selection and optimization of antigens and the design of epitope-driven vaccines. Hum Vaccin Immunother 11:2312-2321.

Chaudhury S, Abdulhameed M D M, Singh N, Tawa G J, D'haeseleer P M, et al. (2013) Rapid Countermeasure Discovery against *Francisella tularensis* Based on a Metabolic Network Reconstruction. Plos One 8.

Khushal Khambhati, Gargi Bhattacharjee, Nisarg Gohil, Darren Braddick, Vishwesh Kulkarni and Vijai Singh, (2019) Exploring the Potential of Cell-Free Protein Synthesis for Extending the Abilities of Biological Systems. Front. Bioeng. Biotechnol., 7:248. doi.org/10.3389/fbioc.2019.00248.

Li, J., Mahajan, A., and Tsai, M.-D. (2006). Ankyrin repeat: a unique motif mediating protein-protein interactions. Biochemistry 45, 15168-15178. doi: 10.1021/bi062188q Pan, X. et al. (2008) Ankyrin repeat proteins comprise a diverse family of bacterial type IV effectors. Science 320, 1651-1654.

Magdalena Franco, Patrik M. D'haeseleer, Steven S. Branda, Megan J. Liou, Yasmeen Haider, Brent W. Segelke, and Sahar H. El-Etr (2018). Proteomic Profiling of *Burkholderia thailandensis* During Host Infection Using Bio-Orthogonal Noncanonical Amino Acid Tagging (BONCAT). Front Cell Infect Microbiol. 8:370. doi: 10.3389/fcimb.2018.00370

Sun P, Ju H, Liu Z, Ning Q, Zhang J, Zhao X, et al. Bioinformatics Resources and Tools for Conformational B-Cell Epitope Prediction. Comput Math Methods Med. 2013; 2013:943636.

Wang A P, Li N, Zhou J M, Chen Y M, Jiang M, Qi Y H, et al. Mapping the B cell epitopes within the major capsid protein L I of human papillomavirus type 16. Int J Biol Macromol. 2018 Oct. 15; 118:1354-61.

Bi Y, Jin Z, Wang Y, Mou S, Wang W, Wei Q, et al. Identification of Two Distinct Linear B Cell Epitopes of the Matrix Protein of the Newcastle Disease Virus Vaccine Strain LaSota. Viral Immunol. 2019 June; 32 (5): 221-9.

Yang W-J, Lai J-F, Peng K-C, Chiang H-J, Weng C-N, Shiuan D. Epitope mapping of *Mycoplasma* hyopneumoniae using phage displayed peptide libraries and the immune responses of the selected phagotopes. J Immunol Methods. 2005 September; 304 (1-2): 15-29.

Mullen L M, Nair S P, Ward J M, Rycroft A N, Henderson B. Phage display in the study of infectious diseases. Trends Microbiol. 2006 March; 14 (3): 141-7.

Ndam N T, Denoeud-Ndam L, Doritchamou J, Viwami F, Salanti A, Nielsen M A, et al. Protective Antibodies against Placental Malaria and Poor Outcomes during Pregnancy, Benin. Emerg Infect Dis. 2015 May; 21 (5): 813-23.

Gonzales S J, Reyes R A, Braddom A E, Batugedara G, Bol S, Bunnik E M. Naturally Acquired Humoral Immunity Against *Plasmodium falciparum* Malaria. Front Immunol. 2020; 11:594653.

Li H, Wang X-X, Wang B, Fu L, Liu G, Lu Y, et al. Latently and uninfected healthcare workers exposed to T B make protective antibodies against *Mycobacterium tuberculosis*. Proc Natl Acad Sci USA. 2017 May 9; 114 (19): 5023-8.

Sharma G, Holt R A. T-cell epitope discovery technologies. Hum Immunol. 2014 Jun. 1; 75 (6): 514-9.

Sharma G, Rive C M, Holt R A. Rapid selection and identification of functional CD8+ T cell epitopes from large peptide-coding libraries. Nat Commun. 2019 Oct. 7; 10:4553.

Caron E, Kowalewski D J, Chiek Koh C, Sturm T, Schuster H, Aebersold R. Analysis of Major Histocompatibility Complex (MHC) Immunopeptidomes Using Mass Spectrometry. Mol Cell Proteomics MCP. 2015 December; 14 (12): 3105-17.

Mara-Koosham G, Hutt J A, Lyons C R, Wu T H. Antibodies Contribute to Effective Vaccination against Respiratory Infection by Type A *Francisella tularensis* Strains. Infect Immun. 2011 Apr. 1; 79 (4): 1770-8.

Ray H J, Cong Y, Murthy A K, Selby D M, Klose K E, Barker J R, et al. Oral Live Vaccine Strain-Induced Protective Immunity against Pulmonary *Francisella tularensis* Challenge Is Mediated by CD4+ T Cells and Antibodies, Including Immunoglobulin A. Clin Vaccine Immunol CVI. 2009 April; 16 (4): 444-52.

Rhinehart-Jones T R, Fortier A H, Elkins K L. Transfer of immunity against lethal murine *Francisella* infection by specific antibody depends on host gamma interferon and T cells. Infect Immun. 1994 August; 62 (8): 3129-37.

Hogan R J, Lafontaine E R. Antibodies Are Major Drivers of Protection against Lethal Aerosol Infection with Highly Pathogenic *Burkholderia* spp. mSphere [Internet]. 2019 Jan. 2 [cited 2021 Mar. 15]; 4 (1). Available from: https://www.ncbi.nlm.nih.gov/pmc/articles/PMC6315082/

Jones S M, Ellis J F, Russell P, Griffin K F, Oyston P C F. Passive protection against *Burkholderia pseudomallei* infection in mice by monoclonal antibodies against capsular polysaccharide, lipopolysaccharide or proteins. J Med Microbiol. 2002; 51 (12): 1055-62.

Khakhum N, Bharaj P, Myers J N, Tapia D, Kilgore P B, Ross B N, et al. *Burkholderia pseudomallei* AtonB Ahcp1 Live Attenuated Vaccine Strain Elicits Full Protective Immunity against Aerosolized Melioidosis Infection. mSphere [Internet]. 2019 Jan. 2 [cited 2021 Mar. 15]; 4 (1). Available from: https://www.ncbi.nlm.nih.gov/pmc/articles/PMC6315081/

Nakajima R, Escudero R, Molina D M, Rodríguez-Vargas M, Randall A, Jasinskas A, et al. Towards Development of Improved Serodiagnostics for Tularemia by Use of *Francisella tularensis* Proteome Microarrays. J Clin Microbiol. 2016 July; 54 (7): 1755-65.

Felgner P L, Kayala M A, Vigil A, Burk C, Nakajima-Sasaki R, Pablo J, et al. A *Burkholderia pseudomallei* protein microarray reveals serodiagnostic and cross-reactive antigens. Proc Natl Acad Sci USA. 2009 Aug. 11; 106 (32): 13499-504.

Yi J, Simpanya M F, Settles E W, Shannon A B, Hernandez K, Pristo L, et al. Caprine humoral response to *Burkholderia pseudomallei* antigens during acute melioidosis from aerosol exposure. PLOS Negl Trop Dis. 2019 February; 13 (2): e0006851.

Ashkenazy H, Abadi S, Martz E, Chay O, Mayrose I, Pupko T, et al. ConSurf 2016: an improved methodology to estimate and visualize evolutionary conservation in macromolecules. Nucleic Acids Res. 2016 Jul. 8; 44 (W1): W344-350.

Ren J, Ellis J, Li J. Influenza A HA's conserved epitopes and broadly neutralizing antibodies: a prediction method. J Bioinform Comput Biol. 2014 October; 12 (5): 1450023.

Fiuza T S, Lima J P M S, de Souza G A. EpitoCore: Mining Conserved Epitope Vaccine Candidates in the Core Proteome of Multiple Bacteria Strains. Front Immunol. 2020; 11:816.

Manavalan B, Govindaraj R G, Shin T H, Kim M O, Lee G. iBCE-E L: A New Ensemble Learning Framework for Improved Linear B-Cell Epitope Prediction. Front Immunol. 2018; 9:1695.

Jespersen M C, Peters B, Nielsen M, Marcatili P. BepiPred-2.0: improving sequence-based B-cell epitope prediction using conformational epitopes. Nucleic Acids Res. 2017 Jul. 3; 45 (W1): W24-9.

Twine S, Shen H, Harris G, Chen W, Sjostedt A, Ryden P, et al. BALB/c mice, but not C57B L/6 mice immunized with a ΔclpB mutant of *Francisella tularensis* subspecies *tularensis* are protected against respiratory challenge with wild-type bacteria: association of protection with post-vaccination and post-challenge immune responses. Vaccine. 2012 May 21; 30 (24): 3634-45.

Lu Z, Rynkiewicz M J, Madico G, Li S, Yang C Y, Perkins H M, et al. B-cell epitopes in GroEL of *Francisella tularensis*. PLOS One. 2014; 9 (6): e99847.

Vita R, Mahajan S, Overton J A, Dhanda S K, Martini S, Cantrell J R, et al. The Immune Epitope Database (IEDB): 2018 update. Nucleic Acids Res. 2019 Jan. 8; 47 (D1): D339-43.

Purcell A W, Mccluskey J, Rossjohn J. More than one reason to rethink the use of peptides in vaccine design. Nat Rev Drug Discov. 2007 May; 6 (5): 404-14.

Sun T, Han H, Hudalla G A, Wen Y, Pompano R R, Collier J H. Thermal stability of self-assembled peptide vaccine materials. Acta Biomater. 2016 Jan. 15; 30:62-71.

Crane D D, Warner S L, Bosio C M. A novel role for plasmin mediated degradation of opsonizing antibody in the evasion of host immunity by virulent, but not attenuated, *Francisella tularensis*. J Immunol Baltim Md 1950. 2009 Oct. 1; 183 (7): 4593-600.

Clinton S R, Bina J E, Hatch T P, Whitt M A, Miller M A. Binding and activation of host plasminogen on the surface of *Francisella tularensis*. BMC Microbiol. 2010 Mar. 12; 10:76.

Shams F, Oldfield N J, Wooldridge K G, Turner D P J. Fructose-1,6-bisphosphate aldolase (FBA)-a conserved glycolytic enzyme with virulence functions in bacteria: "µl met by moonlight." Biochem Soc Trans. 2014 December; 42 (6): 1792-5.

Kunert A, Losse J, Gruszin C, Hühn M, Kaendler K, Mikkat S, et al. Immune evasion of the human pathogen *Pseudomonas aeruginosa*: elongation factor Tuf is a factor H and plasminogen binding protein. J Immunol Baltim Md 1950. 2007 Sep. 1; 179 (5): 2979-88.

Pancholi V, Chhatwal G S. Housekeeping enzymes as virulence factors for pathogens. Int J Med Microbiol IJMM. 2003 December; 293 (6): 391-401.

Lottenberg R, Minning-Wenz D, Boyle M D. Capturing host plasmin (ogen): a common mechanism for invasive pathogens? Trends Microbiol. 1994 January; 2 (1): 20-4.

Terrier B, Degand N, Guilpain P, Servettaz A, Guillevin L, Mouthon L. Alpha-enolase: a target of antibodies in infectious and autoimmune diseases. Autoimmun Rev. 2007 January; 6 (3): 176-82.

Al-Maleki A R, Mariappan V, Vellasamy K M, Tay S T, Vadivelu J. Altered Protcome of *Burkholderia pseudo-*

*mallei* Colony Variants Induced by Exposure to Human Lung Epithelial Cells. PloS One. 2015; 10 (5): e0127398.

Sun P, Guo S, Sun J, Tan L, Lu C, Ma Z. Advances in In-silico B-cell Epitope Prediction. Curr Top Med Chem. 2019; 19 (2): 105-15.

Larsen J E P, Lund O, Nielsen M. Improved method for predicting linear B-cell epitopes. Immunome Res. 2006 Apr. 24; 2:2.

Ponomarenko J, Bui H-H, Li W, Fusseder N, Bourne P E, Sette A, et al. ElliPro: a new structure-based tool for the prediction of antibody epitopes. BMC Bioinformatics. 2008 Dec. 2; 9:514.

Kringelum J V, Lundegaard C, Lund O, Nielsen M. Reliable B cell epitope predictions: impacts of method development and improved benchmarking. PLOS Comput Biol. 2012; 8 (12): e1002829.

Singh H, Ansari H R, Raghava G P S. Improved Method for Linear B-Cell Epitope Prediction Using Antigen's Primary Sequence. PLOS ONE. 2013 May 7; 8 (5): e62216.

Safavi A, Kefayat A, Mahdevar E, Abiri A, Ghahremani F. Exploring the out of sight antigens of SARS-COV-2 to design a candidate multi-epitope vaccine by utilizing immunoinformatics approaches. Vaccine. 2020 Nov. 10; 38 (48): 7612-28.

Devi Y D, Devi A, Gogoi H, Dehingia B, Doley R, Buragohain A K, et al. Exploring rotavirus proteome to identify potential B- and T-cell epitope using computational immunoinformatics. Heliyon. 2020 Dec. 29; 6 (12): e05760.

Liu T, Shi K, Li W. Deep learning methods improve linear B-cell epitope prediction. BioData Min. 2020 Apr. 17; 13:1.

B Cell Help [Internet]. [cited 2021 Aug. 5]. Available from: http://tools.iedb.org/bcell/help/ #Bepipred-2.0

Eickhoff C S, Terry F E, Peng L, Meza K A, Sakala I G, Van Aartsen D, et al. Highly Conserved Influenza T cell epitopes Induce Broadly Protective Immunity. Vaccine. 2019 Aug. 23; 37 (36): 5371-81.

Grassl N, Kulak N A, Pichler G, Geyer P E, Jung J, Schubert S, et al. Ultra-deep and quantitative saliva proteome reveals dynamics of the oral microbiome. Genome Med. 2016 Apr. 21; 8:44.

Zhang X, Chen W, Ning Z, Mayne J, Mack D, Stintzi A, et al. Deep Metaproteomics Approach for the Study of Human Microbiomes. Anal Chem. 2017 Sep. 5; 89 (17): 9407-15.

Blakeley-Ruiz J A, Erickson A R, Cantarel B L, Xiong W, Adams R, Jansson J K, et al. Metaproteomics reveals persistent and phylum-redundant metabolic functional stability in adult human gut microbiomes of Crohn's remission patients despite temporal variations in microbial taxa, genomes, and proteomes. Microbiome. 2019 Feb. 11; 7:18.

Long S, Yang Y, Shen C, Wang Y, Deng A, Qin Q, et al. Metaproteomics characterizes human gut microbiome function in colorectal cancer. NPJ Biofilms Microbiomes. 2020 Mar. 24; 6:14.

Park S K (Robin), Jung T, Thuy-Boun P S, Wang A Y, Yates J R, Wolan D W. ComPIL 2.0: An Updated Comprehensive Metaproteomics Database. J Proteome Res. 2019 Feb. 1; 18 (2): 616-22.

Perez-Riverol Y, Csordas A, Bai J, Bernal-Llinares M, Hewapathirana S, Kundu D J, et al. The PRIDE database and related tools and resources in 2019: improving support for quantification data. Nucleic Acids Res. 2019 Jan. 8; 47 (Database issue): D442-50.

TABLE 5

Amino acid sequences of immunoreactive peptides identified in *Francisella tularensis*.

| SEQ ID NO: | Protein Name | Gene Name | Immunoreactive peptide amino acid sequence |
|---|---|---|---|
| 1 | Aminotransferase | aspC1 | LPIDDAEK |
| 2 | Glutamate dehydrogenase | gdh | FHPSVYSGIIK |
| 3 | Pyruvate dehydrogenase acetyltransferase unit | aceF | VSQGSLILK |
| 4 | 60 kDa chaperonin | groL | DRVDDALHATR |
| 5 | Chaperone protein DnaK | dnaK | NTADNLIHSSR |
| 6 | Chaperone protein DnaK | dnaK | SSSGLSEEDIEK |
| 7 | 60 kDa chaperonin | groL | DNTTIIDGAGEK |
| 8 | 60 kDa chaperonin | groL | EGVITVEEGK |
| 9 | Catalase-peroxidase | katG | AVAQVYAENGNEQK |
| 10 | Malate dehydrogenase | mdh | FSGVPDNK |
| 11 | Outer membrane protein 26 | omp26 | EIPADQLGTIK |
| 12 | Succinate dehydrogenase flavoprotein subunit | sdhA | ITILATGGAGR |
| 13 | ATP synthase subunit alpha | atpA | GEVATDLTSPIEK |
| 14 | Elongation factor Ts | tsf | ESGKPAEIIEK |
| 15 | Elongation factor Ts | tsf | TVEAETLGAYIHGSK |
| 16 | Chaperone protein DnaK | dnaK | IAGLEVK |
| 17 | Cell division protein FtsZ | ftsZ | KETEVVTGASNAPK |
| 18 | Trigger factor | tig | GGVDTFENEIK |
| 19 | ATP synthase subunit alpha | atpA | SVDQALQTGIK |
| 20 | Catalase-peroxidase | katG | NDNLSPQSVDLSPLR |
| 21 | Isocitrate dehydrogenase [NADP] | idh | VADIELETK |
| 22 | Fructose-1,6-bisphosphate aldolase | fbaB | KINIDTDLR |
| 23 | Glutamate dehydrogenase | gdh | GFVHDPEGITTDEK |
| 24 | SuccinateCoA ligase [ADP-forming] subunit beta | sucC | PANFLDVGGGATK |
| 25 | Chaperone protein DnaK | dnaK | KVPYAVIK |
| 26 | Malonyl CoA-acyl carrier protein transacylase | | EPTTAVVQNFDAK |
| 27 | Peroxiredoxin | | KVPNVTFK |
| 28 | Chaperone protein DnaK | dnaK | IINEPTAAA-LAYGVDSK |
| 29 | Conserved hypothetical lipoprotein | lpnA | ATVYTTYNNNPQGSVR |
| 30 | Elongation factor Tu | tuf | TTVTGVEMFR |

TABLE 5-continued

Amino acid sequences of immunoreactive peptides identified in *Francisella tularensis*.

| SEQ ID NO: | Protein Name | Gene Name | Immunoreactive peptide amino acid sequence |
|---|---|---|---|
| 31 | SuccinateCoA ligase [ADP-forming] subunit beta | sucC | EVAESLIGK |
| 32 | 30S ribosomal protein S1 | rpsA | KIELWDR |
| 33 | Elongation factor Tu | tuf | HYAHVDCPGHADYVK |
| 34 | Transcription elongation factor GreA | greA | IVGEDEADIDNQK |
| 35 | 60 kDa chaperonin | groL | SFGTPTITK |
| 36 | Aconitate hydratase | acnA | GIPLVILAGK |
| 37 | Chaperone protein DnaK | dnaK | AYAEQAQAAVAQGGAK |
| 38 | Chaperone protein DnaK | dnaK | FHDLVTAR |
| 39 | Outer membrane protein 26 | omp26 | DGSVGWVK |
| 40 | 3-oxoacyl-(Acyl-carrier-protein) reductase | fabG | VALVTGASR |
| 41 | Chaperone protein DnaK | dnaK | ALEDAGLSK |
| 42 | Enoyl-[acyl-carrier-protein] reductase [NADH] | fabI | TLAASGISNFK |
| 43 | Aconitate hydratase | acnA | TAHTTTFEALAR |
| 44 | Elongation factor Ts | tsf | LDVGEGIEK |

TABLE 6 amino acid sequences of immunoreactive peptides identified in *Burkholderia pseudomallei*

| SEQ ID NO: | Protein Name | Gene Name | Immunoreactive peptide amino acid sequence |
|---|---|---|---|
| 45 | AspartateTrna (Asp/Asn) ligase | aspS | TGAQDGDIIFFAADR |
| 46 | Adenylosuccinate synthetase | purA | QDQIGITLANVGK |
| 47 | Dihydrolipoyl dehydrogenase | odhL | FPFSINGR |
| 48 | Ankyrin repeat-containing protein |  | IGDAPAPNAQK |
| 49 | Phosphoribosyl-formylglycinami-dinesynthase | purL | GATETFVVLPR |
| 50 | DNA-directed RNA polymerase subunit beta | rpoB | STGPYSLVTQQPLGGK |
| 51 | 50S ribosomal protein L6 | rplF | GYRPPEPYK |
| 52 | DNA-directed RNA polymerase subunit beta | rpoC | ISLYATTVGR |
| 53 | Enolase | eno | GIANSILIK |
| 54 | Uncharacterized protein |  | IDCLTNAYTAR |
| 55 | DNA gyrase subunit A | gyrA | INVVLPVR |
| 56 | Aspartate-semialdehyde dehydrogenase | asd | VTGTLSVPVGR |
| 57 | Malic enzyme |  | AALLSNSNFGSAPSASSR |
| 58 | 50S ribosomal protein L10 | rplJ | AQTVVLAEYR |
| 59 | 50S ribosomal protein L6 | rplF | AIIANAVHGVTK |
| 60 | Glutamine synthetase | glnA | ALNAITNPTTNSYK |
| 61 | Nucleoside diphosphate kinase | ndk | NVIGQIYSR |
| 62 | Antioxidant protein LsfA |  | LIITYPASTGR |
| 63 | UDP-glucose 4-epimerase |  | GYSVLEVVR |
| 64 | Enolase | eno | SAIVDIIGR |
| 65 | Acetyl-CoA acetyltransferase |  | LPLSVGCTTINK |
| 66 | Adenosylhomo-cysteinase | ahcY | SKFDNLYGCR |
| 67 | KHG/KDPG aldolase | eda | FGVSPGLTR |
| 68 | 10 kDa chaperonin | groES | TASGIVIPDAAAEKPDQGEVLAIGPGKR |
| 69 | Saccharopine dehydrogenase |  | HGQLVQDVFTR |
| 70 | Citrate synthase | gltA | YSIGQPFVYPR |
| 71 | AspartateTrna (Asp/Asn) ligase | aspS | YVAAHHPFTSPK |
| 72 | Gamma-aminobutyraldehyde dehydrogenase |  | SVLAAAAGNLK |
| 73 | Peptide chain release factor 2 | prfB | SYVLDQSR |
| 74 | Polyketide non-ribosomal peptide synthase |  | AWFIPLSAR |

TABLE 6-continued amino acid sequences of immunoreactive peptides identified in *Burkholderia pseudomallei*

| SEQ ID NO: | Protein Name | Gene Name | Immunoreactive peptide amino acid sequence |
|---|---|---|---|
| 75 | Transcription termination/antitermination protein | nusG | VTGFVGGAR |
| 76 | Beta sliding clamp | dnaN | FTFGQVELVSK |
| 77 | Malate synthase | aceB | IATLIVRPR |
| 78 | PTS system, EIIA component | | ISGHHLEVTPAIR |
| 79 | Phosphoenolpyruvate synthase | ppsA | IFILQARPETVK |
| 80 | Thiol:disulfide interchange protein | dsbA | NYNIDGVPTIVVQGK |
| 81 | RND family efflux transporter MFP subunit | bpeA | AQANLATQNALVAR |
| 82 | Inosine-5-monophosphate dehydrogenase | guaB | LVGIVTNR |
| 83 | Periplasmic maltose-binding protein | malE | VNWLYINK |
| 84 | Putative extracellular ligand binding protein | | VVATDAQQGPALADYAK |
| 85 | Acid phosphatase | acpA | NIVVIYAENR |
| 86 | NADH-quinone oxidoreductase subunit F | nuoF | EGTGWLYR |
| 87 | Type VI secretion system | hcp-1 | IGGNQGGNTQGAWSLTK |
| 88 | 50S ribosomal protein L23 | rplW | AAVELLFK |
| 89 | 50S ribosomal protein L6 | rplF | LTLVGVGYR |
| 90 | 50S ribosomal protein L17 | rplQ | LFDVLGPR |
| 91 | Aconitate hydratase | | IVLESVLR |

What is claimed is:

1. A method of identifying an immunogenic peptide comprising:
   a) identifying an interactive peptide by contacting a peptide library generated from a pathogenic agent with purified peptide-specific immunoglobulins under conditions to form peptide-immunoglobulin complexes between the interactive peptides and the specific immunoglobulins and identifying one or more interactive peptides bound to the peptide-immunoglobulin complexes; and
   b) comparing the identified interactive peptides of step (a) to peptides bound to control immunoglobulins, and selecting at least one identified peptide of step (a) that does not bind to the control immunoglobulins or is enriched in the interactive peptides of step (a) as compared to the peptide bound to control immunoglobulins, thereby identifying an immunogenic peptide.

2. The method of claim 1, wherein the interactive peptides of step a) are obtained from one or more of convalescent sera or from sera or plasma collected from a subject who was immunized with or exposed to the pathogenic agent or the control immunoglobulins are obtained from sera or plasma from a subject who was not exposed to or immunized with the pathogenic agent.

3. The method of claim 1, wherein the contacting step a) comprises a method of contacting host cells transfected with the pathogenic agent and cultured in a media supplied with an azide-bearing methionine analog that labels pathogenic agent peptides, with the peptide library of step (a).

4. The method of claim 1, wherein selecting the peptide library comprises a bioinformatics analysis to include peptides that are predicted to be B-cell epitopes, deeply evolutionary conserved, conserved across the majority of sequenced pathogenic strains, surface exposed, part of membrane proteins, or any combination thereof.

5. The method of claim 1, further comprising assaying the peptide for a broad spectrum immunity against all variants of the same pathogenic agent.

6. The method of claim 1, wherein the pathogenic agent is genetically engineered to express a modified (RNA methionine synthase (metRS).

7. The method of claim 1, wherein the immunogenic peptide identified by the method comprises an amino acid sequence set forth in SEQ ID NOs: 1-91.

8. The method of claim 1, wherein the selecting the peptide further comprises:
   a) generating a plurality of control and identified pairs of datasets, each pair comprising (i) an identified dataset comprising the identified peptides, and (ii) a corresponding control dataset comprising control peptides purified based on immunoglobulins; and
   b) identifying the peptides that are more abundant in each identified dataset as compared to the corresponding control dataset, wherein identifying the peptides that are more abundant comprises generating a frequency for peptides occurring more abundantly in the identified dataset relative to the corresponding control dataset.

9. The method of claim 8, wherein selecting the at least one peptide (i) does not include determining an average log fold change in abundance, and (ii) does not employ a t-test to identify peptides with a significantly higher average abundance in experimental datasets as compared to control datasets.

10. The method of claim 8, further comprising:
   generating a plurality of input datasets corresponding to the plurality of control and identified pairs of datasets, each input dataset comprising the peptides in the peptide library;
   normalizing input datasets against each other based on median ratios for peptides occurring in every input dataset; and
   normalizing the identified and control datasets against their respective input datasets based on the median ratios.

11. The method of claim 8, further comprising identifying candidate epitopes, wherein identifying candidate epitopes comprises performing evolutionary conservation analysis on the identified and control peptides, and wherein the evolutionary conservation analysis comprises at least one of (i) generating an average amino acid conservation score, or (ii) checking for the presence of the peptide in the genome of all sequenced strains of the pathogen.

* * * * *

UNITED STATES PATENT AND TRADEMARK OFFICE
CERTIFICATE OF CORRECTION

| | | |
|---|---|---|
| PATENT NO. | : 12,139,815 B2 | Page 1 of 1 |
| APPLICATION NO. | : 17/586687 | |
| DATED | : November 12, 2024 | |
| INVENTOR(S) | : Franco et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 46 days.

Signed and Sealed this
Eighth Day of July, 2025

Coke Morgan Stewart
*Acting Director of the United States Patent and Trademark Office*